United States Patent
Bukhman

(10) Patent No.: US 8,827,912 B2
(45) Date of Patent: Sep. 9, 2014

(54) METHODS AND SYSTEMS FOR DETECTING EPILEPTIC EVENTS USING NNXX, OPTIONALLY WITH NONLINEAR ANALYSIS PARAMETERS

(75) Inventor: Vladislav Bukhman, East Northport, NY (US)

(73) Assignee: Cyberonics, Inc., Houston, TX (US)

( * ) Notice: Subject to any disclaimer, the term of this patent is extended or adjusted under 35 U.S.C. 154(b) by 1082 days.

(21) Appl. No.: 12/768,472

(22) Filed: Apr. 27, 2010

(65) Prior Publication Data

US 2011/0270095 A1    Nov. 3, 2011

Related U.S. Application Data

(63) Continuation-in-part of application No. 12/429,746, filed on Apr. 24, 2009, now Pat. No. 8,172,759.

(51) Int. Cl.
*A61N 1/36*        (2006.01)
*A61B 5/0205*    (2006.01)

(52) U.S. Cl.
USPC ........................... 600/483; 600/509; 600/516

(58) Field of Classification Search
USPC .............................. 600/483, 509; 607/2, 3, 45
See application file for complete search history.

(56) References Cited

U.S. PATENT DOCUMENTS

| | | |
|---|---|---|
| 4,172,459 A | 10/1979 | Hepp |
| 4,291,699 A | 9/1981 | Geddes et al. |
| 4,541,432 A | 9/1985 | Molina-Negro et al. |
| 4,573,481 A | 3/1986 | Bullara |
| 4,702,254 A | 10/1987 | Zabara |
| 4,867,164 A | 9/1989 | Zabara |
| 4,920,979 A | 5/1990 | Bullara |
| 4,949,721 A | 8/1990 | Toriu et al. |
| 4,979,511 A | 12/1990 | Terry, Jr. |
| 5,025,807 A | 6/1991 | Zabara |
| 5,113,869 A | 5/1992 | Nappholz et al. |
| 5,137,020 A | 8/1992 | Wayne et al. |
| 5,154,172 A | 10/1992 | Terry, Jr. et al. |
| 5,179,950 A | 1/1993 | Stanislaw |

(Continued)

FOREIGN PATENT DOCUMENTS

| | | |
|---|---|---|
| EP | 1145736 | 10/2001 |
| EP | 1486232 | 12/2004 |

(Continued)

OTHER PUBLICATIONS

Bachman, D.,S. et al.; "*Effects of Vagal Volleys and Serotonin on Units of Cingulate Cortex in Monkeys*;" Brain Research, vol. 130 (1977). pp. 253-269.

(Continued)

*Primary Examiner* — Jacqueline Cheng
*Assistant Examiner* — Michael Catina
(74) *Attorney, Agent, or Firm* — Cyberonics, Inc.

(57) ABSTRACT

Disclosed herein are methods, systems, and apparatus for detecting an epilepsy event in a patient using a medical device. The medical device is capable of determining an occurring epilepsy event, for example a seizure or an increased risk of a seizure. The determination is performed by determining at least one NNXX value from the beat sequence of the patient's heart. The medical device may then take a responsive action, such as warning, logging the time of the seizure, computing and storing one or more seizure severity indices, and treating the epilepsy event.

21 Claims, 21 Drawing Sheets

(56) References Cited

U.S. PATENT DOCUMENTS

| | | |
|---|---|---|
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,243,980 A | 9/1993 | Mehra |
| 5,251,634 A | 10/1993 | Weinberg |
| 5,263,480 A | 11/1993 | Wernicke et al. |
| 5,269,302 A | 12/1993 | Swartz et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,311,876 A | 5/1994 | Olsen et al. |
| 5,313,953 A | 5/1994 | Yomtov et al. |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. |
| 5,404,877 A | 4/1995 | Nolan et al. |
| 5,425,373 A | 6/1995 | Causey, III |
| 5,522,862 A | 6/1996 | Testerman et al. |
| 5,540,730 A | 7/1996 | Terry, Jr. et al. |
| 5,540,734 A | 7/1996 | Zabara |
| 5,571,150 A | 11/1996 | Wernicke et al. |
| 5,611,350 A | 3/1997 | John |
| 5,645,570 A | 7/1997 | Corbucci |
| 5,651,378 A | 7/1997 | Matheny et al. |
| 5,658,318 A | 8/1997 | Stroetmann et al. |
| 5,683,422 A | 11/1997 | Rise |
| 5,690,681 A | 11/1997 | Geddes et al. |
| 5,690,688 A | 11/1997 | Noren et al. |
| 5,700,282 A | 12/1997 | Zabara |
| 5,707,400 A | 1/1998 | Terry, Jr. et al. |
| 5,716,377 A | 2/1998 | Rise et al. |
| 5,720,771 A | 2/1998 | Snell |
| 5,743,860 A | 4/1998 | Hively et al. |
| 5,792,186 A | 8/1998 | Rise |
| 5,800,474 A | 9/1998 | Benabid et al. |
| 5,833,709 A | 11/1998 | Rise et al. |
| 5,913,876 A | 6/1999 | Taylor et al. |
| 5,916,239 A | 6/1999 | Geddes et al. |
| 5,928,272 A | 7/1999 | Adkins et al. |
| 5,941,906 A | 8/1999 | Barreras, Sr. et al. |
| 5,942,979 A | 8/1999 | Luppino |
| 5,978,702 A | 11/1999 | Ward et al. |
| 5,987,352 A | 11/1999 | Klein et al. |
| 5,995,868 A | 11/1999 | Osorio et al. |
| 6,016,449 A | 1/2000 | Fischell et al. |
| 6,018,682 A | 1/2000 | Rise |
| 6,061,593 A | 5/2000 | Fischell et al. |
| 6,073,048 A | 6/2000 | Kieval et al. |
| 6,083,249 A | 7/2000 | Familoni |
| 6,091,992 A | 7/2000 | Bourgeois et al. |
| 6,104,956 A | 8/2000 | Naritoku et al. |
| 6,115,628 A | 9/2000 | Stadler et al. |
| 6,115,630 A | 9/2000 | Stadler et al. |
| 6,128,538 A | 10/2000 | Fischell et al. |
| 6,134,474 A | 10/2000 | Fischell et al. |
| 6,167,311 A | 12/2000 | Rezai |
| 6,171,239 B1 | 1/2001 | Humphrey |
| 6,175,764 B1 | 1/2001 | Loeb et al. |
| 6,205,359 B1 | 3/2001 | Boveja |
| 6,208,894 B1 | 3/2001 | Schulman et al. |
| 6,208,902 B1 | 3/2001 | Boveja |
| 6,221,908 B1 | 4/2001 | Kilgard et al. |
| 6,248,080 B1 | 6/2001 | Miesel et al. |
| 6,253,109 B1 | 6/2001 | Gielen |
| 6,269,270 B1 | 7/2001 | Boveja |
| 6,272,379 B1 | 8/2001 | Fischell et al. |
| 6,304,775 B1 | 10/2001 | Iasemidis et al. |
| 6,324,421 B1 | 11/2001 | Stadler et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,784 B1 | 3/2002 | Lozano et al. |
| 6,356,788 B2 | 3/2002 | Boveja |
| 6,366,813 B1 | 4/2002 | DiLorenzo |
| 6,366,814 B1 | 4/2002 | Boveja |
| 6,374,140 B1 | 4/2002 | Rise |
| 6,397,100 B2 | 5/2002 | Stadler et al. |
| 6,427,086 B1 | 7/2002 | Fischell et al. |
| 6,429,217 B1 | 8/2002 | Puskas |
| 6,449,512 B1 | 9/2002 | Boveja |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,477,418 B2 | 11/2002 | Plicchi et al. |
| 6,480,743 B1 | 11/2002 | Kirkpatrick et al. |
| 6,484,132 B1 | 11/2002 | Hively et al. |
| 6,501,983 B1 | 12/2002 | Natarajan et al. |
| 6,505,074 B2 | 1/2003 | Boveja et al. |
| 6,532,388 B1 | 3/2003 | Hill et al. |
| 6,542,774 B2 | 4/2003 | Hill et al. |
| 6,549,804 B1 | 4/2003 | Osorio et al. |
| 6,556,868 B2 | 4/2003 | Naritoku et al. |
| 6,560,486 B1 | 5/2003 | Osorio et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,594,524 B2 | 7/2003 | Esteller et al. |
| 6,599,250 B2 | 7/2003 | Webb et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,985 B2 | 9/2003 | Sweeney et al. |
| 6,628,987 B1 | 9/2003 | Hill et al. |
| 6,647,296 B2 | 11/2003 | Fischell et al. |
| 6,656,125 B2 | 12/2003 | Misczynski et al. |
| 6,656,960 B2 | 12/2003 | Puskas |
| 6,668,191 B1 | 12/2003 | Boveja |
| 6,671,555 B2 | 12/2003 | Gielen et al. |
| 6,671,556 B2 | 12/2003 | Osorio et al. |
| 6,684,105 B2 | 1/2004 | Cohen et al. |
| 6,721,603 B2 | 4/2004 | Zabara et al. |
| 6,735,474 B1 | 5/2004 | Loeb et al. |
| 6,738,671 B2 | 5/2004 | Christophersom et al. |
| 6,760,626 B1 | 7/2004 | Boveja |
| 6,768,969 B1 | 7/2004 | Nikitin et al. |
| 6,788,975 B1 | 9/2004 | Whitehurst et al. |
| 6,793,670 B2 | 9/2004 | Osorio et al. |
| 6,819,953 B2 | 11/2004 | Yonce et al. |
| 6,819,956 B2 | 11/2004 | DiLorenzo |
| 6,832,114 B1 | 12/2004 | Whitehurst et al. |
| 6,836,685 B1 | 12/2004 | Fitz |
| 6,885,888 B2 | 4/2005 | Rezai |
| 6,904,390 B2 | 6/2005 | Nikitin et al. |
| 6,920,357 B2 | 7/2005 | Osorio et al. |
| 6,934,580 B1 | 8/2005 | Osorio et al. |
| 6,934,585 B1 | 8/2005 | Schloss |
| 6,944,501 B1 | 9/2005 | Pless |
| 6,957,107 B2 | 10/2005 | Rogers |
| 6,961,618 B2 | 11/2005 | Osorio et al. |
| 6,985,771 B2 | 1/2006 | Fischell et al. |
| 6,990,377 B2 | 1/2006 | Gliner et al. |
| 7,006,859 B1 | 2/2006 | Osorio et al. |
| 7,006,872 B2 | 2/2006 | Gielen et al. |
| 7,010,351 B2 | 3/2006 | Firlik et al. |
| 7,024,247 B2 | 4/2006 | Gliner et al. |
| 7,054,792 B2 | 5/2006 | Frei et al. |
| 7,058,453 B2 | 6/2006 | Nelson et al. |
| 7,076,288 B2 | 7/2006 | Skinner |
| 7,079,977 B2 | 7/2006 | Osorio et al. |

(56) References Cited

U.S. PATENT DOCUMENTS

| | | |
|---|---|---|
| 7,134,996 B2 | 11/2006 | Bardy |
| 7,139,677 B2 | 11/2006 | Hively et al. |
| 7,146,211 B2 | 12/2006 | Frei et al. |
| 7,146,217 B2 | 12/2006 | Firlik et al. |
| 7,146,218 B2 | 12/2006 | Esteller et al. |
| 7,149,572 B2 | 12/2006 | Frei et al. |
| 7,164,941 B2 | 1/2007 | Misczynski et al. |
| 7,167,750 B2 | 1/2007 | Knudson et al. |
| 7,174,206 B2 | 2/2007 | Frei et al. |
| 7,177,678 B1 | 2/2007 | Osorio et al. |
| 7,188,053 B2 | 3/2007 | Nikitin et al. |
| 7,204,833 B1 | 4/2007 | Osorio et al. |
| 7,209,786 B2 | 4/2007 | Brockway |
| 7,209,787 B2 | 4/2007 | DiLorenzo |
| 7,221,981 B2 | 5/2007 | Gliner |
| 7,225,013 B2 | 5/2007 | Geva et al. |
| 7,228,167 B2 | 6/2007 | Kara |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,254,439 B2 | 8/2007 | Misczynski et al. |
| 7,263,467 B2 | 8/2007 | Sackellares et al. |
| 7,276,026 B2 | 10/2007 | Skinner |
| 7,277,758 B2 | 10/2007 | DiLorenzo |
| 7,280,867 B2 | 10/2007 | Frei et al. |
| 7,282,030 B2 | 10/2007 | Frei et al. |
| 7,289,844 B2 | 10/2007 | Misczynski et al. |
| 7,292,890 B2 | 11/2007 | Whitehurst et al. |
| 7,295,881 B2 | 11/2007 | Cohen et al. |
| 7,299,096 B2 | 11/2007 | Balzer et al. |
| 7,302,298 B2 | 11/2007 | Lowry et al. |
| 7,305,268 B2 | 12/2007 | Gliner et al. |
| 7,321,837 B2 | 1/2008 | Osorio et al. |
| 7,324,850 B2 | 1/2008 | Persen et al. |
| 7,324,851 B1 | 1/2008 | DiLorenzo |
| 7,346,391 B1 | 3/2008 | Osorio et al. |
| 7,353,063 B2 | 4/2008 | Simms, Jr. |
| 7,353,064 B2 | 4/2008 | Gliner et al. |
| 7,373,199 B2 | 5/2008 | Sackellares et al. |
| 7,389,144 B1 | 6/2008 | Osorio et al. |
| 7,401,008 B2 | 7/2008 | Frei et al. |
| 7,403,820 B2 | 7/2008 | DiLorenzo |
| 7,433,732 B1 | 10/2008 | Carney et al. |
| 7,570,999 B2 | 8/2009 | Libbus et al. |
| 2002/0072782 A1 | 6/2002 | Osorio et al. |
| 2002/0099417 A1 | 7/2002 | Naritoku et al. |
| 2002/0116030 A1 | 8/2002 | Rezai |
| 2002/0151939 A1 | 10/2002 | Rezai |
| 2002/0188214 A1 | 12/2002 | Misczynski et al. |
| 2003/0074032 A1 | 4/2003 | Gliner |
| 2003/0083716 A1 | 5/2003 | Nicolelis et al. |
| 2003/0083726 A1 | 5/2003 | Zeijlemaker et al. |
| 2003/0125786 A1 | 7/2003 | Gliner et al. |
| 2003/0130706 A1 | 7/2003 | Sheffield et al. |
| 2003/0144829 A1 | 7/2003 | Geatz et al. |
| 2003/0181954 A1 | 9/2003 | Rezai |
| 2003/0181958 A1 | 9/2003 | Dobak |
| 2003/0208212 A1 | 11/2003 | Cigaina |
| 2003/0210147 A1 | 11/2003 | Humbard |
| 2003/0212440 A1 | 11/2003 | Boveja |
| 2003/0236558 A1 | 12/2003 | Whitehurst et al. |
| 2004/0006278 A1 | 1/2004 | Webb et al. |
| 2004/0088024 A1 | 5/2004 | Firlik et al. |
| 2004/0122484 A1 | 6/2004 | Hatlestad et al. |
| 2004/0122485 A1 | 6/2004 | Stahmann et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138647 A1 | 7/2004 | Osorio et al. |
| 2004/0138711 A1 | 7/2004 | Osorio et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0172085 A1 | 9/2004 | Knudson et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0199212 A1 | 10/2004 | Fischell et al. |
| 2004/0249302 A1 | 12/2004 | Donoghue et al. |
| 2004/0249416 A1 | 12/2004 | Yun et al. |
| 2005/0004621 A1 | 1/2005 | Boveja et al. |
| 2005/0020887 A1 | 1/2005 | Goldberg |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0027284 A1 | 2/2005 | Lozano et al. |
| 2005/0033378 A1 | 2/2005 | Sheffield et al. |
| 2005/0033379 A1 | 2/2005 | Lozano et al. |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075701 A1 | 4/2005 | Shafer |
| 2005/0075702 A1 | 4/2005 | Shafer |
| 2005/0101873 A1 | 5/2005 | Misczynski et al. |
| 2005/0119703 A1 | 6/2005 | DiLorenzo |
| 2005/0124901 A1 | 6/2005 | Misczynski et al. |
| 2005/0131467 A1 | 6/2005 | Boveja et al. |
| 2005/0131485 A1 | 6/2005 | Knudson et al. |
| 2005/0131486 A1 | 6/2005 | Boveja et al. |
| 2005/0131493 A1 | 6/2005 | Boveja et al. |
| 2005/0143786 A1 | 6/2005 | Boveja et al. |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0149157 A1 | 7/2005 | Hunter et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0187590 A1 | 8/2005 | Boveja et al. |
| 2005/0192644 A1 | 9/2005 | Boveja et al. |
| 2005/0197590 A1 | 9/2005 | Osorio et al. |
| 2005/0234307 A1 | 10/2005 | Heinonen et al. |
| 2005/0245971 A1 | 11/2005 | Brockway et al. |
| 2005/0261542 A1 | 11/2005 | Riehl |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0288600 A1 | 12/2005 | Zhang et al. |
| 2005/0288760 A1 | 12/2005 | Machado et al. |
| 2006/0009815 A1 | 1/2006 | Boveja |
| 2006/0074450 A1 | 4/2006 | Boveja |
| 2006/0079936 A1 | 4/2006 | Boveja |
| 2006/0094971 A1 | 5/2006 | Drew |
| 2006/0095081 A1 | 5/2006 | Zhou et al. |
| 2006/0106430 A1 | 5/2006 | Fowler et al. |
| 2006/0135877 A1 | 6/2006 | Giftakis et al. |
| 2006/0135881 A1 | 6/2006 | Giftakis et al. |
| 2006/0155495 A1 | 7/2006 | Osorio et al. |
| 2006/0167497 A1 | 7/2006 | Armstrong et al. |
| 2006/0173493 A1 | 8/2006 | Armstrong et al. |
| 2006/0173522 A1 | 8/2006 | Osorio |
| 2006/0190056 A1 | 8/2006 | Fowler et al. |
| 2006/0195163 A1 | 8/2006 | KenKnight et al. |
| 2006/0200206 A1 | 9/2006 | Firlik et al. |
| 2006/0212091 A1 | 9/2006 | Lozano et al. |
| 2006/0224067 A1 | 10/2006 | Giftakis et al. |
| 2006/0224191 A1 | 10/2006 | Dilorenzo |
| 2006/0241697 A1 | 10/2006 | Libbus et al. |
| 2006/0241725 A1 | 10/2006 | Libbus et al. |
| 2006/0293720 A1 | 12/2006 | DiLorenzo |
| 2007/0027486 A1 | 2/2007 | Armstrong et al. |

(56) References Cited

U.S. PATENT DOCUMENTS

| | | |
|---|---|---|
| 2007/0027497 A1 | 2/2007 | Parnis et al. |
| 2007/0027498 A1 | 2/2007 | Maschino et al. |
| 2007/0027500 A1 | 2/2007 | Maschino et al. |
| 2007/0032834 A1 | 2/2007 | Gliner et al. |
| 2007/0043392 A1 | 2/2007 | Gliner et al. |
| 2007/0055320 A1 | 3/2007 | Weinand et al. |
| 2007/0066906 A1* | 3/2007 | Goldberger et al. ......... 600/509 |
| 2007/0073150 A1 | 3/2007 | Gopalsami et al. |
| 2007/0073355 A1 | 3/2007 | Dilorenzo |
| 2007/0088403 A1 | 4/2007 | Wyler et al. |
| 2007/0100278 A1 | 5/2007 | Frei et al. |
| 2007/0100392 A1 | 5/2007 | Maschino et al. |
| 2007/0142862 A1 | 6/2007 | Dilorenzo |
| 2007/0142873 A1 | 6/2007 | Esteller et al. |
| 2007/0150024 A1 | 6/2007 | Leyde et al. |
| 2007/0150025 A1 | 6/2007 | Dilorenzo et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173901 A1 | 7/2007 | Reeve |
| 2007/0173902 A1 | 7/2007 | Maschino et al. |
| 2007/0179534 A1 | 8/2007 | Firlik et al. |
| 2007/0179557 A1 | 8/2007 | Maschino et al. |
| 2007/0179558 A1 | 8/2007 | Gliner et al. |
| 2007/0208212 A1 | 9/2007 | DiLorenzo |
| 2007/0213785 A1 | 9/2007 | Osorio et al. |
| 2007/0219455 A1 | 9/2007 | Wong et al. |
| 2007/0233192 A1 | 10/2007 | Craig |
| 2007/0239210 A1 | 10/2007 | Libbus et al. |
| 2007/0244407 A1 | 10/2007 | Osorio |
| 2007/0249953 A1 | 10/2007 | Osorio et al. |
| 2007/0249954 A1 | 10/2007 | Virag et al. |
| 2007/0255147 A1 | 11/2007 | Drew et al. |
| 2007/0255155 A1 | 11/2007 | Drew et al. |
| 2007/0260147 A1* | 11/2007 | Giftakis et al. ............... 600/483 |
| 2007/0260289 A1 | 11/2007 | Giftakis et al. |
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2008/0033503 A1 | 2/2008 | Fowler et al. |
| 2008/0033508 A1 | 2/2008 | Frei et al. |
| 2008/0046035 A1 | 2/2008 | Fowler et al. |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |
| 2008/0234780 A1 | 9/2008 | Smith et al. |
| 2008/0319281 A1 | 12/2008 | Aarts |
| 2009/0124870 A1* | 5/2009 | Arends et al. ................ 600/301 |

FOREIGN PATENT DOCUMENTS

| | | |
|---|---|---|
| GB | 2026870 | 2/1980 |
| GB | 2079610 | 1/1982 |
| WO | 00/64336 | 11/2000 |
| WO | 2004/036377 | 4/2004 |
| WO | 2005/007120 | 1/2005 |
| WO | 2005/053788 | 6/2005 |
| WO | 2005/067599 | 7/2005 |
| WO | 2006/050144 | 5/2006 |
| WO | 2006/122148 | 11/2006 |
| WO | 2007/066343 | 6/2007 |
| WO | 2007/072425 | 6/2007 |
| WO | 2007/124190 | 11/2007 |
| WO | 2007/124192 | 11/2007 |
| WO | 2007124126 | 11/2007 |
| WO | 2007/7142523 | 12/2007 |
| WO | 2008/045597 | 4/2008 |

OTHER PUBLICATIONS

Baevskii, R.M. "*Analysis of Heart Rate Variability in Space Medicine*;" Human Physiology, vol. 28, No. 2, (2002); pp. 202-213.

Baevsky, R.M., et al.; "*Autonomic Cardiovascular and Respiratory Control During Prolonged Spaceflights Aboard the International Space Station*;" J. Applied Physiological, vol. 103, (2007) pp. 156-161.

Boon, P., et al.; "*Vagus Nerve Stimulation for Epilepsy, Clinical Efficacy of Programmed and Magnet Stimulation;*" (2001); pp. 93-98.

Boon, Paul, et al.; "*Programmed and Magnet-Induced Vagus Nerve Stimulation for Refractory Epilepsy;*" Journal of Clinical Neurophysiology vol. 18 No. 5; (2001); pp. 402-407.

Borovikova, L.V., et al.; "*Vagus Nerve Stimulation Attenuates the Systemic Inflammatory Response to Endotoxin*;" Letters to Nature; vol. 405; (May 2000); pp. 458-462.

Brack, Kieran E., et al.; "*Interaction Between Direct Sympathetic and Vagus Nerve Stimulation on Heart Rate in the Isolated Rabbit Heart;*" Experimental Physiology vol. 89, No. 1; pp. 128-139.

Chakravarthy, N., et al.; "*Controlling Synchronization in a Neuron-Level Population Model;*" International Journal of Neural Systems, vol. 17, No. 2 (2007) pp. 123-138.

Clark, K.B., et al.; "*Posttraining Electrical Stimulation of Vagal Afferents with Concomitant Vagal Efferent Inactivation Enhances Memory Storage Processes in the Rat;*" Neurobiology of Learning and Memory, vol. 70, 364-373 (1998) Art. No. NL983863.

Elmpt, W.J.C., et al.; "*A Model of Heart Rate Changes to Detect Seizures in Severe Epilepsy*" Seizure vol. 15, (2006) pp. 366-375.

Frei, M.G., et al.; "*Left Vagus Nerve Stimulation with the Neurocybernetic Prosthesis Has Complex Effects on Heart Rate and on Its Variability in Humans:*" Epilepsia, vol. 42, No. 8 (2001); pp. 1007-1016.

George, M.S., et al.; "*Vagus Nerve Stimulation: A New Tool for Brain Research and Therapy;*"Society of Biological Psychiatry vol. 47 (2000) pp. 287-295.

"*Heart Rate Variability-Standards of Measurement, Physiological Interpretation, and Clinical Use*" Circulation-Electrophysiology vol. 93, No. 5; http://circ.ahajournals.org/cgi/content-nw/full/93/5/1043/F3.

Henry, Thomas R.; "*Therapeutic Mechanisms of Vague Name Stimulation;*". Neurology, vol. 59 (Supp 4) (Sep. 2002), pp. S3-S14.

Hallowitz et al., "*Effects of Vagal Volleys on Units of Intralaminar and Juxtalaminar Thalamic Nuclei in Monkeys;*" Brain Research, vol. 130 (1977), pp. 271-286.

Iasemidis; L.D., et al.; "*Dynamical Resetting of the Human Brain at Epilepctic Seizures: Application of Nonlinear Dynamics and Global Optimization Techniques;*" IEEE Transactions on Biomedical Engineering, vol. 51, No. 3 (Mar. 2004); pp. 493-506.

Iasemidis; L.D., et al.; "*Spatiotemporal Transition to Epileptic Seizures: A Nonlinear Dynamical Analysis of Scalp and Intracranial EEG Recordings;*" Spatiotemporal Models in Biological and Artificial Systems; F.L. Silva et al. (Eds.) IOS Press, 1997; pp. 81-88.

Iasemidis, L.D.; "*Epileptic Seizure Prediction and Control*" IEEE Transactions on Biomedical Engineering, vol. 50, No. 5 (May 2003); pp. 549-558.

Kautzner, J., et al.; "*Utility of Short-Term Heart Rate Variability for Prediction of Sudden Cardiac Death After Acute Myocardial Infarction*" Acta Univ. Palacki. Olomuc., Fac. Med., vol. 141 (1998) pp. 69-73.

Koenig, S.A., et al.; "*Vagus Nerve Stimulation Improves Severely Impaired Heart Rate Variability in a Patient with Lennox-Gastaut-Syndrome*" Seizure (2007) Article in Press-Yseiz-1305; pp. 1-4.

Koo, B., "*EEG Changes With Vagus Nerve Stimulation*" Journal of Clinical Neurophysiology, vol. 18 No. 5 (Sep. 2001); pp. 434-441.

(56) References Cited

OTHER PUBLICATIONS

Krittayaphong, M.D., et al.; "Heart Rate Variability in Patients with Coronary Artery Disease: Differences in Patients with Higher and Lower Depression Scores" Psychosomatic Medicine vol. 59 (1997) pp. 231-235.
Leutmezer, F., et al.; "Electrocardiographic Changes at the Onset of Epileptic Seizures;" Epilepsia, vol. 44, No. 3; (2003); pp. 348-354.
Lewis, M.E., et al.; "Vagus Nerve Stimulation Decreases Left Ventricular Contractility in Vivo in the Human and Pig Heart" The Journal of Physiology vol. 534, No. 2, (2001) pp. 547-552.
Li, M., et al.; "Vagal Nerve Stimulation Markedly Improves Long-Term Survival After Chronic Heart Failure in Rats:" Circulation (Jan. 2004) pp. 120-124.
Licht, C.M.M.; Association Between Major Depressive Disorder and Heart Rate Variability in the Netherlands Study of Depression and Anxiety (NESDA); Arch. Gen Psychiatry, vol. 65, No. 12 (Dec. 2008); pp. 1358-1367.
Lockard et al., "Feasibility and Safety of Vagal Stimulation in Monkey Model;" Epilepsia, vol. 31 (Supp. 2) (1990), pp. S20-S26.
McClintock, P., "Can Noise Actually Boost Brain Power" Physics World Jul. 2002; pp. 20-21.
Mori, T., et al.; "Noise-Induced Entrainment and Stochastic Resonance in Human Brain Waves" Physical Review Letters vol. 88, No. 21 (2002); pp. 218101-1-218101-4.
Mormann, F., "Seizure prediction: the long and winding road," Brain 130 (2007), 314-333.
Nouri, M.D.; "Epilepsy and the Autonomic Nervous System" emedicine (updated May 5, 2006); pp. 1-14; http://www.emedicine.com/neuro/topic658.htm.
O'Regan, M.E., et al.; "Abnormalities in Cardiac and Respiratory Function Observed During Seizures in Childhood" Developmental Medicine & Child Neurlogy, vol. 47 (2005) pp. 4-9.
Pathwardhan, R.V., et al., Control of Refractory status epilepticus precipitated by anticonvulasnt withdrawal using left vagal nerve stimulation: a case report, Surgical Neurology 64 (2005) 170-73.
Poddubnaya, E.P., "Complex Estimation of Adaptation Abilities of the Organism in Children Using the Indices of Responsiveness of the Cardiovascular System and Characteristics of EEG" Neurophysiology vol. 38, No. 1 (2006); pp. 63-74.
Rugg-Gunn, F.J., et al.; "Cardiac Arrhythmias in Focal Epilepsy: a Prospective Long-Term Study" www.thelancet.com vol. 364 (2004) pp. 2212-2219.
Sajadieh, A., et al.; "Increased Heart Rate and Reduced Heart-Rte Variability are Associated with Subclinical Inflammation in Middle-Aged and Elderly Subjects with No Apparent Heart Disease" European Heart Journal vol. 25, (2004); pp. 363-370.
Schernthaner, C., et al.; "Autonomic Epilepsy-The Influence of Epileptic Discharges on Heart Rate and Rhythm" The Middle European Joural of Medicine vol. 111, No. 10 (1999) pp. 392-401.
Terry et al.; "The Implantable Neurocybernetic Prosthesis System", Pacing and Clinical Electrophysiology, vol. 14, No. 1 (Jan. 1991), pp. 86-93.
Tubbs, R.S., et al.; "Left-Sided Vagus Nerve Stimulation Decreases Intracranial Pressure Without Resultant Bradycardia in the Pig: A Potential Therapeutic Modality for Humans" Child's Nervous System Original Paper; Springer-Verlag 2004.
Umetani, M.D., et al.; "Twenty-Four Hour Time Domain Heart Rate Variability and Heart Rate: Relations to Age and Gender Over Nince Decades"JACC vol. 31, No. 3; (Mar. 1998); pp. 593-601.
Vonck, K., et al. "The Mechanism of Action of Vagus Nerve Stimulation for Refractory Epilepsy-The Current Status", Journal of Neurophysiology, vol. 18 No. 5 (2001), pp. 394-401.
Woodbury, et al., "Vagal Stimulation Reduces the Severity of Maximal Electroshock Seizures in Intact Rats. Use of a Cuff Electrode for Stimulating and Recording"; Pacing and Clinical Electrophysiology, vol. 14 (Jan. 1991), pp. 94-107.
Zabara, J.; "Neuroinhibition of Xylaine Induced Emesis" Pharmacology & Toxicology, vol. 63 (1988) pp. 70-74.
Zabara, J. "Inhibition of Experimental Seizures in Canines by Repetivie Vagal Stimulation" Epilepsia vol. 33, No. 6 (1992); pp. 1005-1012.
Zabara, J., et al.; "Neural Control of Circulation I"The Physiologist, vol. 28 No. 4 (1985); 1 page.
Zabara, J., et al.; "Neuroinhibition in the Regulation of Emesis" Space Life Sciences, vol. 3 (1972) pp. 282-292.
Osorio, Ivan et al., "An Introduction to Contingent (Closed-Loop) Brain Electrical Stimulation for Seizure Blockage, To Ultra-Short-Term Clinical Trials, and to Multidimensional Statistical Analysis of Therapeutic Efficacy," Journal of Clinical Neurophysiology, vol. 18, No. 6, pp. 533-544, 2001.
Osorio, Ivan et al., "Automated Seizure Abaatement in Humans Using Electrical Stimulation," Annals of Neurology, vol. 57, No. 2, pp. 258-268, 2005.
Sunderam, Sridhar et al., "Vagal and Sciatic Nerve Stimulation Have Complex, Time-Dependent Effects on Chemically-Induced Seizures: A Controlled Study," Brain Research, vol. 918, pp. 60-66, 2001.
Weil, Sabine et al, "Heart Rate Increase in Otherwise Sublinical Seizures Is Different in Temporal Versus Extratemporal Seizure Onset: Support for Temporal Lobe Automatic Influence," Epileptic Disord., vol. 7, No. 3, Sep. 2005, pp. 199-204.
Digenarro, Giancarlo et al., "Ictal Heart Rate Increase Precedes EEG Discharge in Drug-Resistant Mesial Temporal Lobe Seizures," Clinical Neurophysiology, No. 115, 2004, pp. 1169-1177.
Zijlmans, Maeike et al., "Heart Rate Changes and ECG Abnormalities During Epileptic Seizures: Prevalence and Definition of an Objective Clinical Sign," Epilepsia, vol. 43, No. 8, 2002, pp. 847-854.
O'Donovan, Cormac A. et al., "Computerized Seizure Detection Based on Heart Rate Changes," abstract of AES Proceedings, Epilepsia, vol. 36, Suppl. 4, 1995, p. 7.
Robinson, Stephen E et al., "Heart Rate Variability Changes As Predictor of Response to Vagal Nerve Stimulation Therapy for Epilepsy," abstract of AES Proceedings,Epilepsia, vol. 40, Suppl. 7, 1999, p. 147.
Long, Teresa J. et al., "Effectiveness of Heart Rate Seizure Detection Compared to EEG in an Epilepsy MoitoringUnit (EMU)," abstract of AES Proceedings, Epilepsia, vol. 40, Suppl. 7, 1999, p. 174.
Zochowski et al., "Autocorrelations of R-R Distributions As a Measure of Heart Rate Variability," Physical Review E, 56: 3725-3727, 1997.
Loncar-Turukalo et al., "Measures of Deterministic Dynamics of Heart Rate and Blood Pressure Signals in Rats," Acta Polytechnica hungarica, 5 (1): 121-133, 2008.

* cited by examiner

METHODS AND SYSTEMS FOR DETECTING EPILEPTIC EVENTS USING NNXX, OPTIONALLY WITH NONLINEAR ANALYSIS PARAMETERS

This application is a continuation-in-part of application Ser. No. 12/429,746, filed Apr. 24, 2009, now U.S. Pat. No. 8,172,759.

FIELD OF THE INVENTION

This invention relates generally to medical device systems and, more particularly, to medical device systems and methods capable of determining and, in some embodiments, treating an occurring or impending epilepsy event, for example an epileptic seizure or an increased risk of a seizure.

DESCRIPTION OF THE RELATED ART

In recent decades, many advancements have been made in treating diseases involving the human brain, such as epilepsy and depression. Epilepsy involves sporadic episodes of hypersynchronous electrical activity in one or more areas of the brain, which may result in seizures characterized by a loss of cognitive function and/or impaired motor condition. While some disorders involving the brain, such as depression, do not typically involve such acute episodes, it has been observed in many such conditions and disorders that one or more aspects of autonomic function may be impaired.

From research over the last 50 years, it has been discovered that the autonomic status of a patient may be characterized by one or more cardiac system parameters. In particular, researchers have developed a number of parameters based upon measurements of heart activity that may be used to assess not only heart condition but also the general health of the patient. A primary measure of both heart function and general health is heart rate, most commonly resting heart rate derived from the time series of successive R-R intervals measured by electrodes capable of detecting R-waves in the patient's cardiac cycle. Other cardiac parameters, including a large number of parameters for measuring heart rate variability (HRV), have been developed to assess, among other factors, the sympathetic and parasympathetic neural influences on cardiac function and overall health. In general, the activity of the sympathetic nervous system increases heart rate, and parasympathetic activity reduces heart rate.

Many different types of mathematical analysis have been proposed for deriving heart rate and HRV parameters. In particular, periodic and non-periodic parameters may be evaluated using statistical, geometrical, spectral, and fractal analysis, as well as linear dynamic methods, among others. It has been appreciated by numerous researchers that for many epilepsy patients, increases (or, less commonly, decreases) in heart rate may occur in close proximity to epileptic events such as seizures. Thus, it has been proposed to detect seizures based upon detecting sudden changes in heart rate or other heart beat or HRV parameters. Such cardiac-based seizure detection methods may be used to provide a warning to a patient or caregiver, or to initiate a therapy to treat the seizure. See, e.g., U.S. Pat. No. 6,341,236; U.S. Pat. No. 6,671,556.

However, in spite of promising results in the detection of seizures with cardiac parameters, the same parameters that may demonstrate a seizure may also occur in many non-pathologic states. In other words, many proposed methods have extremely high rates of "false positive" event detections, in which an algorithm indicates that an epileptic event such as a seizure has occurred when no such event has taken place. This is referred to frequently as a lack of specificity because detection of the cardiac parameter may not specifically identify the epilepsy event, and may simply result from normal physiological activity of the patient, such as exercise.

While algorithms incorporating a number of cardiac parameters have been proposed to detect epilepsy events, the present invention involves one or more nonlinear parameters that may be used to detect seizures with greater specificity (i.e., fewer false positive detection events) than previous algorithms.

In recent decades, new therapies using electrical signals for treating brain diseases have been found to be effective. In particular, implantable medical devices have been effectively used to deliver therapeutic electrical stimulation to various portions of the human body (e.g., the vagus nerve) for treating these diseases.

As used herein, "stimulation," "neurostimulation," "stimulation signal," or "neurostimulation signal" refers to the application of an electrical, mechanical, magnetic, electro-magnetic, photonic, audio, and/or chemical signal to a neural structure in the patient's body. The signal is an exogenous signal that is distinct from the endogenous electrical, mechanical, and chemical activity (e.g., afferent and/or efferent electrical action potentials) generated by the patient's body and environment. In other words, the stimulation signal (whether electrical, mechanical, magnetic, electro-magnetic, photonic, audio or chemical in nature) applied to the nerve in the present invention is a signal applied from an artificial source, e.g., a neurostimulator.

A "therapeutic signal" refers to a stimulation signal delivered to a patient's body with the intent of treating a medical condition by providing a modulating effect to neural tissue. The effect of a stimulation signal on neuronal activity is termed "modulation"; however, for simplicity, the terms "stimulating" and "modulating", and variants thereof, are sometimes used interchangeably herein. In general, however, the delivery of an exogenous signal itself refers to "stimulation" of the neural structure, while the effects of that signal, if any, on the electrical activity of the neural structure are properly referred to as "modulation." The modulating effect of the stimulation signal upon the neural tissue may be excitatory or inhibitory, and may potentiate acute and/or long-term changes in neuronal activity. For example, the "modulating" effect of the stimulation signal to the neural tissue may comprise one more of the following effects: (a) initiation of an action potential (afferent and/or efferent action potentials); (b) inhibition or blocking of the conduction of action potentials, whether endogenous or exogenously induced, including hyperpolarizing and/or collision blocking, (c) affecting changes in neurotransmitter/neuromodulator release or uptake, and (d) changes in plasticity or neurogenesis of brain tissue.

In some embodiments, electrical neurostimulation may be provided by implanting an electrical device, i.e., an implantable medical device (IMD), underneath the skin of a patient and delivering an electrical signal to a nerve such as a cranial nerve. Generally, electrical neurostimulation signals that perform neuromodulation are delivered by the IMD via one or more leads, although leadless neurostimulators have also been developed. The leads generally terminate at their distal ends in one or more electrodes, and the electrodes, in turn, are electrically coupled to tissue in the patient's body. For example, a number of electrodes may be attached to various points of a nerve or other tissue inside a human body for delivery of a neurostimulation signal.

While feedback stimulation (i.e., an electrical signal applied in response to a sensed body parameter such as heart rate) schemes have been proposed, conventional vagus nerve stimulation (VNS) usually involves non-feedback stimulation characterized by a number of parameters. Specifically, conventional vagus nerve stimulation usually involves a series of grouped electrical pulses defined by an "on-time" and an "off-time." Each sequence of pulses during an on-time may be referred to as a "pulse burst." The burst is followed by the off-time period in which no signals are applied to the nerve. During the on-time, electrical pulses of a defined electrical current (e.g., 0.5-2.0 milliamps) and pulse width (e.g., 0.25-1.0 milliseconds) are delivered at a defined frequency (e.g., 20-30 Hz) for the on-time duration, usually a specific number of seconds, e.g., 10-60 seconds. The pulse bursts are separated from one another by the off-time, (e.g., 30 seconds-5 minutes) in which no electrical signal is applied to the nerve. The on-time and off-time parameters together define a duty cycle, which is the ratio of the on-time to the combination of the on-time and off-time, and which describes the percentage of time that the pulsed electrical signal is applied to the nerve.

In conventional VNS, the on-time and off-time may be programmed to define an intermittent pattern in which a repeating series of electrical pulse bursts are generated and applied to a cranial nerve such as the vagus nerve. The off-time is provided to allow the nerve to recover from the stimulation of the pulse burst, and to conserve power. If the off-time is set at zero, the electrical signal in conventional VNS may provide continuous stimulation to the vagus nerve. Alternatively, the off time may be as long as one day or more, in which case the pulse bursts are provided only once per day or at even longer intervals. Typically, however, the ratio of "off-time" to "on-time" may range from about 0.5 to about 10. It should be noted that "on-time" defines the entire time interval during which pulses are applied to the nerve, and is not limited to the time that electrical charge is actually applied to the nerve. For example, even if off-time is zero (i.e., "continuous" stimulation), if signal parameters include a pulse width of 0.5 milliseconds, and a frequency of 30 Hz, electrical charge is actually applied to the nerve only 30 times per second for ½ millisecond, and thus only 15 milliseconds of every second of "continuous" stimulation would involve electrical charge being applied to the nerve.

In addition to the on-time and off-time, the other parameters defining the electrical signal in conventional VNS may be programmed over a range of values. The pulse width for the pulses in a pulse burst of conventional VNS may be set to a value not greater than about 1 msec, such as about 250-500 μsec, and the number of pulses in a pulse burst is typically set by programming a frequency in a range of about 20-150 Hz (i.e., 20 pulses per second to 150 pulses per second). A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

Although neurostimulation has proven effective in the treatment of a number of medical conditions, it would be desirable to further enhance and optimize neurostimulation for this purpose. For example, it may be desirable to detect an occurring or impending epilepsy event. Such detection may be useful in monitoring the course of a patient's disease or the progress of his or her treatment thereof. Alternatively or in addition, such detection may be useful in warning the patient of an impending epilepsy event or alerting the patient, a physician, a caregiver, or a suitably programmed computer in order for that person or computer program to take action intended to reduce the likelihood, duration, or severity of the epilepsy event or impending epilepsy event, or to facilitate further medical treatment or intervention for the patient. Conventional VNS stimulation as described above does not detect occurring or impending epilepsy events.

SUMMARY OF THE INVENTION

In one aspect of the present invention, a method of detecting an epilepsy event in a patient is provided. The method comprises receiving data relating to a beat sequence of the patient's heart; determining at least one NNXX value from the beat sequence of the patient's heart; comparing the at least one NNXX value to an NNXX threshold; and providing an output indicative of the occurrence of said epilepsy event based on said comparing. In one embodiment, the epilepsy event comprises at least one of an unstable brain state, a brain state indicative of an elevated probability of a seizure, a brain state indicative of an impending seizure, an aura, or a seizure.

In another aspect of the present invention, a computer readable program storage device is provided that is encoded with instructions that, when executed by a computer, perform the method described above.

In another aspect of the present invention, a medical device for detecting an epilepsy event is provided. In one embodiment, the medical device comprises a sensing module adapted to receiving data relating to a beat sequence of the patient's heart; an NNXX processing module adapted to determine at least one NNXX value from the beat sequence of the patient's heart, and adapted to compare the at least one NNXX value to an NNXX threshold; and a communication unit adapted to provide an output indicative of the occurrence of said epilepsy event based on the comparison. The epilepsy event may comprise an unstable brain state, a brain state indicative of an elevated probability of a seizure, a brain state indicative of an impending seizure, an aura, or a seizure. In one embodiment, the medical device comprises an implantable medical device. In another embodiment, the medical device is external to the patient's body.

In a further aspect of the present invention, a method of detecting an epilepsy event in a patient is provided. In one embodiment, the method comprises receiving data relating to a beat sequence of the patient's heart; determining, based on the beat sequence, A) at least one regularity nonlinear analysis parameter, B) at least one predictability nonlinear analysis parameter, and C) at least one NNXX parameter; determining a risk factor for an epilepsy event based upon at least one of A) said at least one regularity nonlinear analysis parameter, B) said at least one predictability nonlinear analysis parameter, and C) said at least one NNXX parameter; comparing said risk factor to a risk factor threshold, and providing an output indicative of the occurrence of the epilepsy event based on said comparing. In one embodiment, the epilepsy event comprises at least one of an unstable brain state, a brain state indicative of an elevated probability of a seizure, a brain state indicative of an impending seizure, an aura, or a seizure.

In a still further aspect of the present invention, a method of detecting an epilepsy event in a patient is provided. In one embodiment, the method comprises receiving data relating to a beat sequence of the patient's heart; determining from said beat sequence at least one of: A) at least one regularity nonlinear analysis parameter, B) at least one predictability nonlinear analysis parameter, and C) at least one NNXX parameter; providing at least one comparison selected from the group consisting of: comparing the at least one regularity nonlinear analysis parameter to a first threshold, comparing the at least one predictability nonlinear analysis parameter to a second threshold, and comparing the at least one NNXX parameter to a third threshold; and providing an output indicative of the occurrence of the epilepsy event based on said at least one comparison.

In a further aspect of the present invention, a method of detecting an epilepsy event in a patient is provided. In one embodiment, the method comprises receiving data relating to a beat sequence of the patient's heart; determining, based on the beat sequence, at least a first cardiac parameter and a second cardiac parameter; adjusting said first cardiac parameter based on said second cardiac parameter; comparing said first cardiac parameter to a first cardiac parameter threshold; and providing an output indicative of the occurrence of the epilepsy event based on said comparing. In one embodiment, the epilepsy event comprises at least one of an unstable brain state, a brain state indicative of an elevated probability of a seizure, a brain state indicative of an impending seizure, an aura, or a seizure. In one embodiment, said adjusting comprises adjusting said first cardiac parameter based upon a nonlinear mathematical function.

BRIEF DESCRIPTION OF THE DRAWINGS

The invention may be understood by reference to the following description taken in conjunction with the accompanying drawings, in which like reference numerals identify like elements, and in which.

Figure 1A:
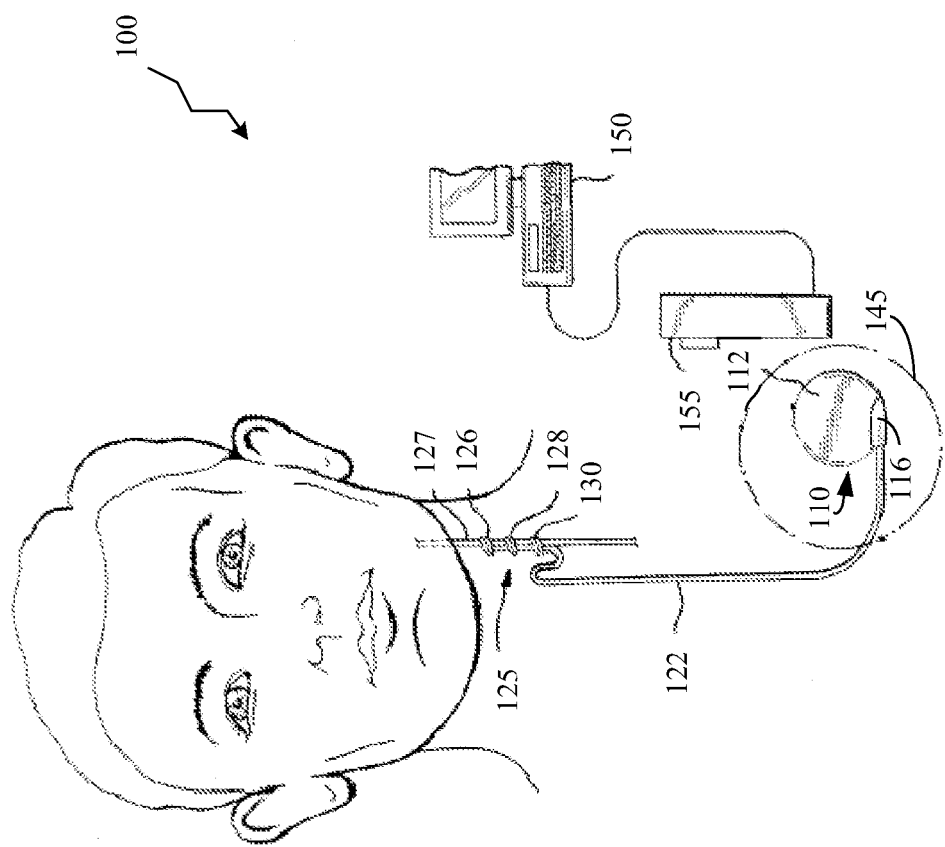
FIG. 1A provides a stylized diagram of an implantable medical device implanted into a patient's body for providing a therapeutic electrical signal to a neural structure of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to."

Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering an electrical signal generated by an IMD to a tissue), sensing electrodes (i.e., electrodes for sensing a physiological indication of a patient's body), and/or electrodes that are capable of delivering a stimulation signal, as well as performing a sensing function.

In one embodiment, the present invention provides a method of detecting an epilepsy event. The epilepsy event can be any one or more of a number of events from a patient's epilepsy condition. Epilepsy events may include, for example, at least one of an unstable brain state, a brain state indicative of an elevated probability of a seizure, a brain state indicative of an impending seizure, an aura, or a seizure, among others.

In one embodiment, the method comprises receiving data relating to a beat sequence of the patient's heart; determining at least one nonlinear analysis parameter from the beat sequence of the patient's heart; comparing the nonlinear analysis parameter to at least one threshold; and providing an output indicative of at least one of an unstable brain state, a brain state indicative of an elevated probability of a seizure, a brain state indicative of an impending seizure, or a seizure, based upon the comparing of the nonlinear analysis parameter to the at least one threshold.

In one embodiment, the present invention provides a method of taking action responsive to an epilepsy event in a patient, comprising receiving data relating to a beat sequence of the patient's heart; determining at least one nonlinear analysis parameter from the beat sequence of the patient's heart; comparing the nonlinear analysis parameter to at least one threshold; and taking a responsive action selected from warning, logging the time of the event, computing and storing one or more seizure event indices, and treating the epilepsy event based upon the comparing of the nonlinear analysis parameter to the at least one threshold.

In one embodiment, treating the epilepsy event comprises cranial nerve stimulation. Cranial nerve stimulation has been proposed to treat a number of medical conditions pertaining to or mediated by one or more structures of the nervous system of the body, including epilepsy and other movement disorders, depression, anxiety disorders and other neuropsychiatric disorders, dementia, traumatic brain injury, coma, migraine headache, obesity, eating disorders, sleep disorders, cardiac disorders (such as congestive heart failure and atrial fibrillation), hypertension, endocrine disorders (such as diabetes and hypoglycemia), and pain (including neuropathic pain and fibromyalgia), among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the numerous disorders for which cranial nerve stimulation has been proposed or suggested as a treatment option, the fact that detailed neural pathways for many (if not all) cranial nerves remain relatively unknown, makes predictions of efficacy for any given disorder difficult or impossible. Moreover, even if such pathways were known, the precise stimulation parameters that would modulate particular pathways relevant to a particular disorder generally cannot be predicted.

In some embodiments, electrical neurostimulation may be provided by implanting an electrical device underneath the skin of a patient and delivering an electrical signal to a nerve such as a cranial nerve. In another alternative embodiment, the signal may be generated by an external pulse generator outside the patient's body, coupled by an RF or wireless link to an implanted electrode.

The data relating to a beat sequence of the patient's heart can be gathered by any of a number of techniques. For example, data relating to a beat sequence may be gathered by an electrocardiogram (ECG) device, such as the CardioBelt ECG acquisition system (offered by Monebo Technologies, Inc., Austin, Tex.). In one embodiment, the data relating to the beat sequence may be related to the R-waves of the beat sequence, such as a time series of R-waves or a series of R-R intervals. Those skilled in the art having benefit of the present disclosure would appreciate that other time series of cardiac waves and/or their fiducial points (e.g., P wave peaks, T wave peaks, etc.) may be used and still remain within the spirit and scope of the present invention.

Data relating to R-waves may be gathered by an ECG device or, in one embodiment, by a vagus nerve stimulator, such as described in U.S. patent application Ser. No. 12/258, 019, filed Oct. 24, 2008, which is hereby incorporated by reference herein.

Receiving the data relating to the beat sequence of the patient's heart may comprise sensing a time of beat sequence of a patient's heart and generating a time series data stream from said time of beat sequence. In a further embodiment, receiving the data relating to the beat sequence of the patient's heart may comprise receiving a series of R-R intervals, and generating the time series data stream may comprise sensing a plurality of R peaks from the R-R intervals and using the R peaks for providing a time stamp to generate the time series data stream based upon the time stamp.

Based upon the R-R intervals time series, many periodic and non-periodic parameters may be evaluated using statistical, geometrical, spectral analysis and linear dynamic methods. However, in spite of promising results in the detection of seizures, the methods referred to in the previous sentence lack specificity. In other words, they yield an unacceptably high rate of falsely detected seizure events.

For example, it is known that heart rate (HR) increases in a significant majority of seizure events and may serve as a reliable indicator of a seizure. However, HR also increases during normal neurological activity completely unrelated to seizures (e.g., a heart rate change induced by exercise or intense emotion, among others). Consequently, the HR increase is a good indicator of a seizure in terms of sensitivity (i.e., a low rate of false negative seizure detections) but a poor indicator in terms of specificity (i.e., rate of false positives).

Figure 12:
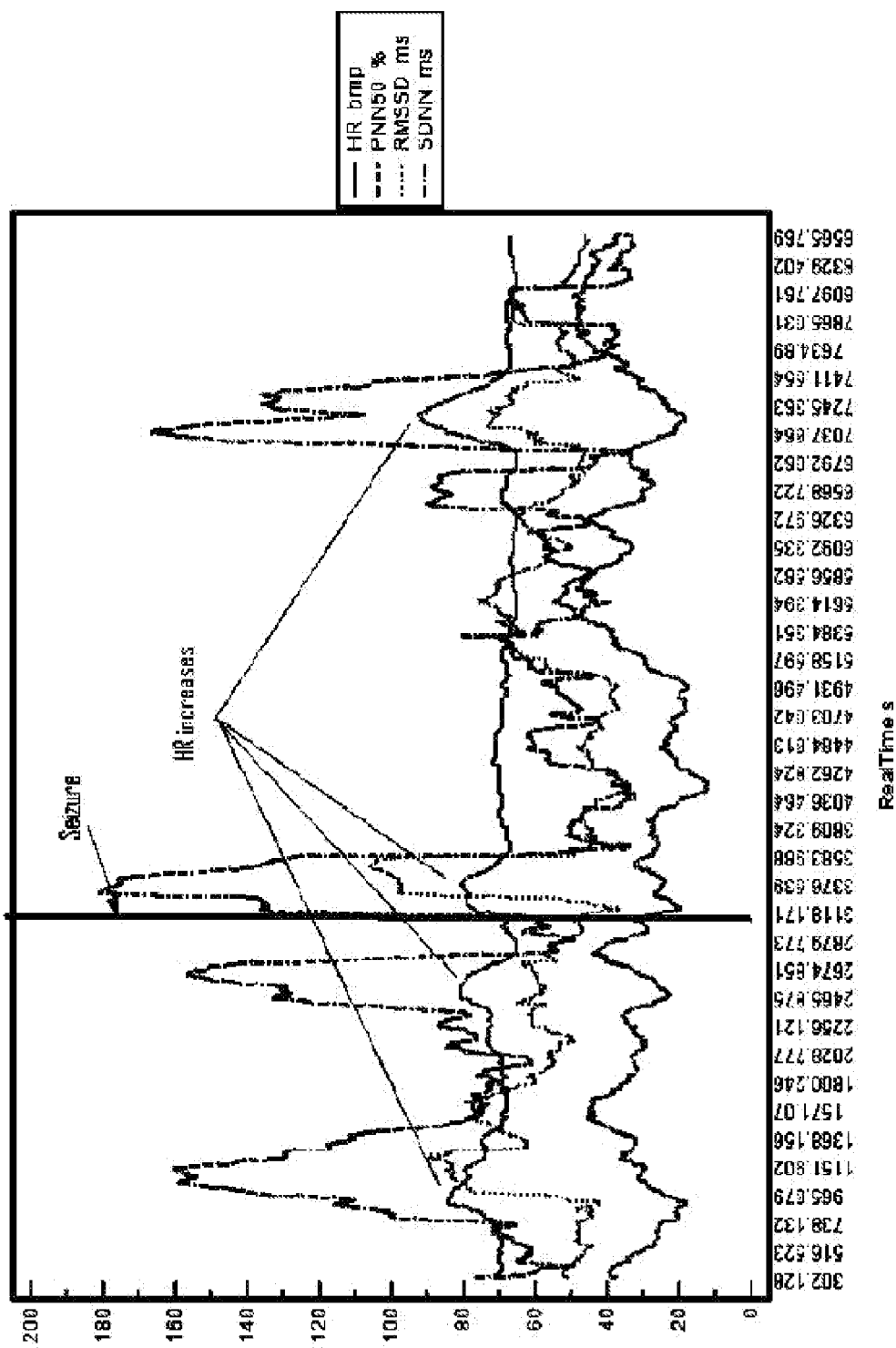
FIG. 12 illustrates a time series of observed values for statistical parameters related to heart rate variability (percentage of differences between adjacent normal R-R intervals that are >50 msec (pNN50), Standard Deviation Normal to Normal R-R intervals (SDNN), and Root Mean Square Successive Difference (RMSSD)) over two and half hours of monitoring with detected and marked seizure events, as well as heart rate increases not contemporaneous with any seizure event, in the same patient as FIG. 9.

The same results have been seen using other statistical Heart Rate Variability (HRV) parameters such as Standard Deviation Normal to Normal R-R intervals (SDNN), Root Mean Square Successive Difference (RMSSD), Coefficient of Variance (CV) and Percentage of differences between adjacent NN intervals that are >50 msec (pNN50) which have high negative or positive correlation coefficients with HR. FIG. 12 shows significant increase/decrease of all above parameters at a time near a seizure, indicating that the parameters may potentially be used as a sensitive indicator of seizure events. However, the same parameters also show significant increase/decrease at three other times without seizures, yielding 3 false detections or a false positive rate of 75%. In one case, the significant increases/decreases takes place up to roughly 240 sec (4 min) after seizure onset.

Figure 13:
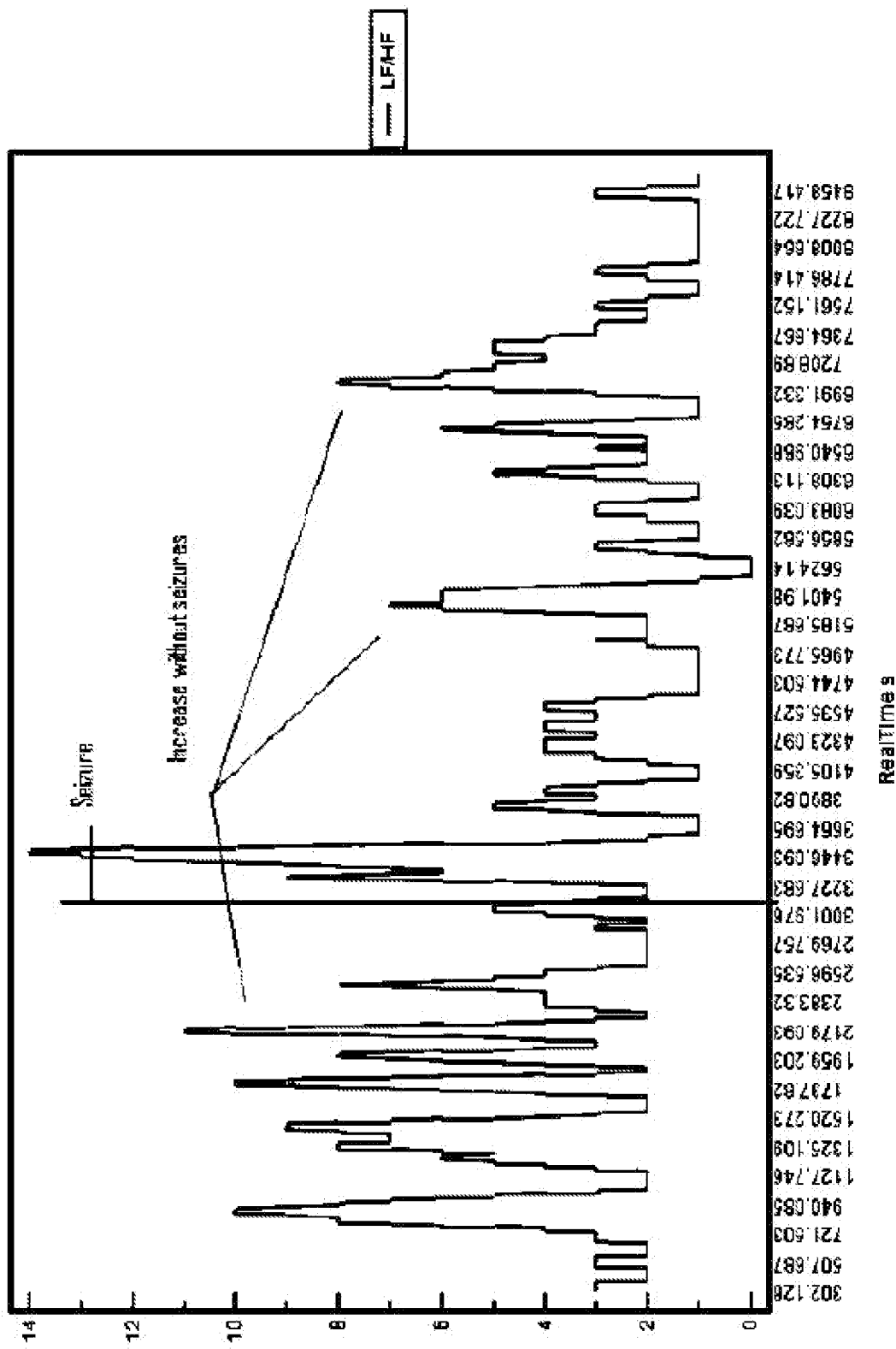
FIG. 13 illustrates a time series of observed values for a spectral parameter related to heart rate variability (low frequency (LF) to high frequency (HF) ratio) over two and half hours of monitoring with a detected and marked seizure event, as well as increases in the LF/HF ratio not contemporaneous with any seizure event, in the same patient as FIG. 9.

In addition to the foregoing limitations from statistical HRV parameters, many spectral analysis HRV parameters also lack specificity. As an example, FIG. 13 illustrates numerous large increases in the low frequency (LF) to high frequency (HF) ratio at times not from seizures (false positives). The only large increase taking place at any time near a seizure takes place roughly 300 sec (5 min) after seizure onset, thus indicating relatively poor sensitivity as well as the obviously poor specificity.

The lack of specificity of existing cardiac-based seizure detection algorithms highlights a fundamental difficulty: the nonstationarity of cardiac systems. The nonstationarity problem is characterized by differences in measured parameter values made at different times for the same patient state and environment. For example, SampEn may have different values for the same person, in the same state and environment, at times t1 and t2. Nonstationarity is addressed in some embodiments of the present invention by using multiple cardiac parameters having relatively low cross-correlation in parallel, instead of using a single parameter. This approach is based on the assumption that if multiple, poorly-correlated parameters exceed or are close to their respective seizure detection thresholds at the same time, the probability of a pathological (e.g., seizure) event is almost 100%. More effective algorithms are needed that consider the nonstationarity problem if the high false positive detection rates (i.e., the low specificity) of existing algorithms are to be overcome. See FIGS. 12-13.

In addition to nonstationarity problems, changes in patient state may also affect the specificity of a given cardiac parameter for determining a seizure event. Because human patients experience significant changes in the environment over unpredictable time horizons, and in addition have varying levels of physical, neural, emotional, and cognitive function and health, a cardiac parameter value (or more generally any body parameter value) that indicates a pathological condition at one patient state may not indicate a pathological condition at a second patient state and vice versa. Any given threshold indicating a pathological condition for the first state (e.g. resting or supine position) can indicate a normal condition for the second state, e.g. during mental or physical workload. This problem may be addressed by providing dynamic adjustment of parameter values that take into account patient state change effects such as rest and exercise, anxiety and calm, or other changes in physical, neural, emotional or cognitive state. By dynamically adjusting measured cardiac values, uniform threshold values for particular seizure detection parameters (e.g., SampEn, SOD, NNXX) can be maintained. In one embodiment, the parameter values are adjusted using HRV values with low correlation to the parameter being adjusted. In alternative embodiments, the thresholds may be dynamically adjusted as a function of patient state changes instead of the parameter values.

In contrast to most statistical and spectral analysis measures, the evaluation of nonlinear analysis parameters, and especially the measurement of regularity and predictability of non-periodic oscillations of R-R time series, can be suitable for prediction and/or detection of epilepsy events providing satisfactory level of both sensitivity and specificity in a timely manner, such as at the onset of the seizure event.

From the heart beat time series data, at least one nonlinear analysis parameter can be determined from the beat sequence of the patient's heart. A "nonlinear analysis parameter" is used herein to refer to a nonlinear dynamics parameter which classifies complex, non-periodic oscillations of a time series of R-R intervals. In certain embodiments, a nonlinear analysis parameter may be referred to as a "chaos parameter."

Exemplary nonlinear analysis parameters include a first group of parameters which measure the regularity (e.g., entropy) of a complex system. For example, approximate entropy (ApEn), fuzzy entropy (FuzzyEn), and sample entropy (SampEn). ApEn, FuzzyEn, and SampEn measure a statistical regularity of a nonlinear time series and reflect a complexity of non-periodic oscillations of HRV. Though not to be bound by theory, greater regularity means lesser complexity, and hence lesser adaptability and functionality.

Another group of nonlinear analysis parameters includes parameters measuring the predictability of a complex system. As an example, the similarity of distribution of math expectancy (SOD), a probability parameter which measures predictability of non-periodic oscillations of HRV may be used in some embodiments of the invention. Though not to be bound by theory, higher predictability of a system means lesser flexibility and functionality.

There are other versions of entropy (regularity) and predictability parameters adapted to specific needs, depending on what time-series signal is desired to be classified, the available duration of the time series, static versus dynamic evaluation, the minimal/maximal size of sliding windows for parameter calculation, and the sliding window step size, among others. For example, recently introduced FuzzyEn (Measuring complexity using FuzzyEn, ApEn, and SampEn. See, e.g., Weiting Chen, Jun Zhuang, Wangxin Yu, Zhizhong Wang Medical engineering & physics 1 Jan. 2009 (volume 31 issue 1 Pages 61-68 DOI: 10.1016/j.medengphy.2008.04.005).

In one embodiment, the regularity nonlinear analysis parameter is SampEn and the predictability nonlinear analysis parameter is SOD, for analysis of the non-periodic oscillations of R-R intervals time series for prediction and detection of seizure events.

Sample entropy (SampEn) is the negative natural logarithm of the conditional probability that two sequences similar for m points remain similar at the $(m+1)^{th}$ point, wherein self-matches are not included in calculating the probability. Sample entropy is defined in terms of m, r, and N, wherein m is the length of the sequences to be compared, r is the tolerance for accepting matches, and N is the length of the time series.

Specifically, in one embodiment, if $B_m(r)$ ($A_m(r)$) is an estimate of the probability that two sequences will match for m(m+1) points, with $A_i$ being an m+1 counterpart of $B_i$:

$$B^m(r) = \frac{1}{N-m} \cdot \sum_{i=1}^{N-m} \frac{B_i - 1}{N - m - 1},$$

$$A^m(r) = \frac{1}{N-m} \cdot \sum_{i=1}^{N-m} \frac{A_i - 1}{N - m - 1}$$

then sample entropy is estimated as:

$$SampEn(m, r, N) = -\ln\left(\frac{A^m(r)}{B^m(r)}\right)$$

T. Loncar-Turukalo, S. Milosavljevic, O Sarenac, N. Japundzic-Zigon, D. Bajic: "Entropy and Gaussianity—Measures of Deterministic Dynamics of Heart Rate and Blood Pressure Signals in Rats", Acta Polytechnica Hungarica, Vol. 5, No. 1, 2008, pp 121-133, ISSN 1785-8860.

Sample entropy can be considered a measure of the regularity of a system. Lower values of SampEn reflect higher levels of regularity. Since electrophysiological rhythms are irregular by nature, higher levels of regularity (i.e., lower values of SampEn) may be a manifestation of a pathological condition. Thus, non-pathological or healthy cardiovascular function is characterized by higher values of SampEn (i.e., higher complexity), and low values of SampEn are a potential indicator of epilepsy events such as seizures.

Similarity of distribution (SOD) is a measurement of the autocorrelation of a distribution of a time series of data points. SOD shows changes in the width of the distribution and the stability of the distribution over time. See, e.g., Zochowski M., Winkowska-Nowak K., Nowak A., Karpinski G., & Budaj A. (1997). Autocorrelations of R-R distributions as a measure of heart rate variability. *Physical Review E*, 56, 3725-2727.

Specifically, in one embodiment, the time series to be analyzed is divided into a sequence of time periods which are moved by s with respect to each other and a probability distribution for the data points (in one embodiment, R-R intervals) is determined. SOD (represented by the variable A(s)) is then:

$$A(s) = \sum_{i=1}^{h} p_i(t) p_i(t+s)$$

where h is the number of cells in the histogram of the probability distribution, t is the starting time point of the window, and $p_i(t)$ is the $i^{th}$ cell of the histogram. SOD will vary from 0 to 1. SOD values approaching 0 suggest that the probability distributions are very wide, or the data sets do not overlap. SOD values approaching 1 suggest that the probability distributions have a high degree of overlap, and that there is a high level of predictability in the next distribution at time s from the present time. In healthy cardiovascular systems, predictability is low. SOD can be considered a measure of the stability and predictability of the system at a given time. Though not to be bound by theory, the higher value reflects the higher stability and predictability of the system, which may indicate a pathological state. Thus, non-pathological cardiovascular function is characterized by lower values of SOD, and high values of SOD are a potential indicator of epilepsy events such as seizures.

One advantageous feature of SampEn and SOD over other measures of regularity and predictability, respectively, is that each can be calculated effectively from relatively short time windows (as few as 10 beats) and SOD is fairly tolerant of noise in the time series data signal.

In addition to the nonlinear analysis parameters described above, other nonlinear analysis parameters exist, for example chaos parameters such as largest Lyapunov exponent, Fractal Dimension by Dispersion Analysis (FDDA), and Detrended Fluctuation Analysis (DFA). However, these parameters are less suitable for applications provided by embodiments of the present invention because they require at least about 300 seconds of time series data for valid results. Moreover, some of these parameters lack sensitivity (e.g., the largest Lyapunov exponent) or specificity (e.g., FDDA and DFA).

One additional advantage of the use of SampEn and SOD to detect seizures is that these two nonlinear analysis parameters have no statistically significant correlation between each other. Further, SOD has no statistically significant correlation with HR, as shown in the following table:

|  |  | HR bmp | SampEn | SODmax |
|---|---|---|---|---|
| HR bmp | Correlation Coefficient |  | −0.827 | 0.068 |
|  | Significance Level P |  | 0.0000 | 0.03492 |
|  | n |  | 963 | 963 |
| SampEn | Correlation Coefficient | −0.827 |  | −0.109 |
|  | Significance Level P | 0.0000 |  | 0.0007244 |
|  | n | 963 |  | 963 |
| SODmax | Correlation Coefficient | 0.068 | −0.109 |  |
|  | Significance Level P | 0.03492 | 0.0007244 |  |
|  | n | 963 | 963 |  |

Pearson correlation coefficient

In some embodiments, the nonlinear analysis parameter(s) (e.g., SampEn, SOD) may be compared to one or more thresholds to determine whether or not an epilepsy event has occurred. The thresholds may be fixed or variable, and may be set manually (e.g., by a physician) or automatically (such as by an algorithm operating in the memory of the medical device). Variable thresholds may be varied periodically over relatively long periods of time (e.g., weeks, months or years), or may be varied by an algorithm operating over either short periods of time (e.g., varying thresholds over minutes or seconds), or over a fixed or variable number of heart beats (e.g., every heart beat, every 2 beats, 4 beats, 5 beats, 10 beats, etc.). Nonlinear analysis parameter thresholds can, for example, be established by a physician for one or more of the particular nonlinear analysis parameter under consideration, optionally as a function of patient-specific parameters such as the patient's age, the patient's sex, the condition of the patient's heart, the severity of the patient's epilepsy, and/or other parameters.

In a specific example, if the nonlinear analysis parameter is SampEn, the threshold may be a lower threshold set at 0.25, or another threshold that indicates that the regularity of the patient's cardiac system is falling below a non-pathological level and into a pathological status. For another example, if the nonlinear analysis parameter is SOD, the upper threshold may be 0.75, or another threshold indicating that the predictability of the patient's cardiac cycle is rising above a non-pathological level, and into a pathological status. For another example, the nonlinear analysis parameter may be SOD-SampEn (i.e., the difference between SOD and SampEn at a particular time point) and the threshold may be 0.5.

While a number of different thresholds and cardiac parameters may be established, the epilepsy event algorithm may determine that an epilepsy event has occurred based upon the crossing of one or more thresholds according to logic appropriate for achieving acceptable levels of specificity and sensitivity. The logic may, for example, declare a seizure when the SOD upper threshold is crossed, either instantaneously or for a specified time period; when the SampEn lower threshold is crossed instantaneously or for a required time limit; when both the SOD and SampEn thresholds are crossed, optionally within specified time constraints, etc.

Based on the comparison between the nonlinear analysis parameter(s) and the threshold(s), if an algorithm determines that an epilepsy event has occurred, one or more responsive actions may be taken selected from warning a patient, caregiver or physician, logging the time of a seizure, computing and storing one or more seizure event indices, and treating the epilepsy event.

A warning may be given as a warning sound (audio tone) or light implemented by a medical device or a signal may be transmitted (via one or more leads or wirelessly) to a separate device adapted to receive an indication of an epilepsy event. Other types of warnings include an automated email, text message, telephone call, or video message sent from a medical device or a unit in communication with a medical device to the patient's cellular telephone, PDA, computer, television, etc. Such a warning may allow the patient, a caregiver or physician to take measures protective of the patient's well-being and those of others, e.g., pulling out of traffic and turning off a car, when the patient is driving; stopping the use of machinery; contacting another adult if the patient is providing childcare; removing the patient from a swimming pool or bathtub; lying down or sitting if the patient is standing, etc.

The time of the event may also be logged by receiving an indication of the current time and associating the indication of the current time with an indication of the epilepsy event.

Seizure event indices may be calculated and stored by appropriate techniques and apparatus. In some instances, the event indices may include a seizure severity index such as the duration of heart rate elevation above a baseline rate, the duration of either (or both) SampEn and SOD above a threshold, etc.

The epilepsy event may be treated by appropriate techniques, such as those discussed below.

Returning to the comparison, for example, if the nonlinear analysis parameter is SOD-SampEn, i.e., the difference between SOD and SampEn at the same time point, a first threshold may be set at 0.2 and a second threshold at 0.6. If the SOD-SampEn value is at or below 0.2, the patient may be considered to be functioning normally. If SOD-SampEn is above 0.2 but below 0.6, a warning about an increased seizure risk may be given, the time to the expected seizure may be logged, one or more prediction indices may be calculated and stored, a treatment may be provided, or two or more thereof. If the SOD-SampEn value rises above the upper threshold of 0.6, an alarm may be given, the time of the event may be logged, one or more epilepsy event indices (e.g., a seizure severity score) may be calculated and stored, the epilepsy event may be treated, or two or more thereof. The term "treatment" may refer to intervening in an ongoing epilepsy event in an effort to reduce the impact or intensity of an actually occurring seizure, or it may refer to an attempt to reduce the impact or intensity of an imminent or predicted seizure, or abort it entirely. Reducing the intensity of an epilepsy event may include incrementally reducing the intensity, substantially reducing the intensity, or substantially eliminating the intensity of the epilepsy event.

The treatment may be one or more treatments known in the art. In one embodiment, the treatment comprises at least one of applying an electrical signal to a neural structure of a patient or delivering a drug to a patient. When the treatment comprises applying an electrical signal to a portion of a neural structure of a patient, the neural structure may be at least one of a portion of a brain structure of the patient, a portion of a cranial nerve of a patient, a portion of a spinal cord of a patient, a portion of a sympathetic nerve structure of the patient, a portion of a parasympathetic nerve structure of the patient, and/or a portion of a peripheral nerve of the patient.

A plurality of epilepsy event thresholds may be provided, referring to any combination of a plurality of nonlinear analysis parameters, a plurality of time periods, or a plurality of conditional events. For example, an algorithm may require both a SampEn value below 0.25 and a SOD value above 0.75 at the same time for the device to declare an epileptic event; or an SOD-SampEn value of 0.5 to be present continuously for a defined duration ranging from 1-10 seconds for the device to declare an epileptic event; or a SampEn value below about 0.25 for a defined duration of from 1-10 seconds after reaching a SOD value above about 0.75 for the device to declare an epileptic event, among others.

Though not intended to be bound by theory, in certain circumstances, one or more nonlinear analysis parameters may exceed or fall below a threshold before the onset of an epileptic event, such as a seizure, whose onset is determined by electroencephalography, observation by a physician or knowledgeable layman, or both. The time before onset may range from a few seconds up to 15-20 minutes. As such, certain embodiments of the method may be considered to yield a prediction of an epileptic event rather than an indication that the event is actually occurring. Stated another way, the epilepsy event may involve an elevation in the risk of a seizure rather than a seizure itself. It should be noted that an epilepsy event involving a prediction may sometimes be a false positive (e.g., an actual seizure may not occur within a specified time—for example 1 hr, 30 minutes, or 5 minutes, depending upon the type of warning desired—of the seizure prediction or indication of elevated risk. However, depending on a physician's judgment, his or her understanding of the devices in use, and the patient's condition, a certain amount of false positives may be tolerable.

The above methods can be performed in a closed-loop system to detect epilepsy events such as seizures. In another embodiment, the above methods can be performed in combination with a continuous or open-loop therapy for epilepsy. In one embodiment, the above method is performed to take action in response to the detection of an epilepsy event, and at all or most other times, a chronic open-loop therapy signal is applied to a target structure in the patient's body. In one embodiment, the target structure is a cranial nerve, such as the vagus nerve.

In addition to the foregoing methods to detect epilepsy events using nonlinear analysis parameter(s), the present invention involves a method of detecting an epilepsy event in a patient using a statistical heart beat parameter, NNXX, that provides an improved measure of parasympathetic neural activity in the epilepsy context.

In one embodiment, the invention relates to a method of detecting an epilepsy event comprising receiving data relating to a beat sequence of the patient's heart; determining at least one NNXX value from the beat sequence of the patient's heart; comparing the at least one NNXX value to an NNXX threshold; and providing an output indicative of the epilepsy event based on the comparing. The epilepsy event may be any of an unstable brain state, a brain state indicative of an elevated probability of a seizure, a brain state indicative of an impending seizure, an aura, or a seizure.

In this embodiment, the receiving step can be as described above.

In this embodiment, the determining step comprises determining at least one NNXX value from the beat sequence of the patient's heart.

The statistical parameter NNXX, in relation to the beat sequence of the patient's heart, is calculated as:

(number of normal interbeat intervals in a sample where (interbeat interval$_i$>interbeat interval$_{i-1}$+ $XX$ msec) or (interbeat interval$_i$<interbeat interval$_{i-1}$−$XX$ msec))/(total number of normal interbeat intervals in the sample), wherein interbeat interval$_{i-1}$ is the normal interbeat interval immediately preceding normal interbeat interval$_i$.

From the foregoing formula it can be seen that NNXX is the ratio of adjacent normal R-R intervals that differ by more than XX milliseconds to all normal R-R intervals in the sample. Stated another way, NNXX is the fraction of all adjacent normal R-R intervals in a sample that differ by more than XX milliseconds. In the foregoing discussion, "normal interbeat intervals" are those which are not due to a pathological condition, such as premature ventricular contractions (PVCs), as a nonlimiting example.

The NNXX parameter is a more general version of a statistical parameter developed in the 1980s for measuring HRV—the NN50 count. Consistent with the formula above, NN50 is the fraction of adjacent, normal RR-intervals in a sample that differ by more than 50 milliseconds. The NN50 count is a measure of parasympathetic (i.e., vagal) activity, with higher NN50 values (representing greater heart rate variability of adjacent normal beats) corresponding to higher vagal activity. In general, greater parasympathetic activity means greater NN50 counts, and also indicates a healthier cardiac cycle in normal patients.

Typically, NN50 counts are measured at rest, and in 5 minute or longer windows to provide better reliability of NN50 as an indicator of vagal activity. It is known that HRV measures, including NN50, decrease significantly as heart rate increases. During exercise in normal patients, the NN50 count approaches zero because of increased sympathetic and decreased parasympathetic regulation of HR. Since elevated HR from seizures would also tend to show a similar reduction in NN50 counts, NN50 counts provide little or no predictive power for epilepsy event detection, since it is usually incapable of distinguishing normal from pathological cardiac activity.

One limitation of NN50 that it measures a relatively high level of vagal activity. In healthy, waking subjects at rest, NN50 values below 0.10 (i.e., less than 10% of beats vary by more than 50 msec) are typical. In patients engaging in non-exercise but ambulatory activity, NN50 counts may be below 0.05, and in many subjects engaging in only moderate physical activity, NN50 counts may be zero. Because it measures a HR sample for relatively high levels of vagal activity, NN50 has poor discriminating power between pathological and non-pathological activity. In other words, NN50 counts determine if a patient's vagal activity is highly functional, but sheds little or no light in determining if a patient's vagal activity is pathologically poor.

It has been discovered by the present inventor that NNXX parameters, usually having XX values lower than 50, can be used to detect epileptic events. Since epileptic seizures are from significantly decreased vagal activity, using values of XX below 50 allows detection of—and ultimately discrimination among—much lower levels of parasympathetic activity than NN50 counts. By using appropriately low values of XX, embodiments of the present invention-provide much better discrimination between reduced vagal activity due to epilepsy and that due to normal physical activity.

Without being bound by theory, a hypothetical and non-limiting example illustrates this concept. A patient having a seizure may experience a slightly elevated HR, in which a baseline HR rises from 70 to 100, but simultaneously have such reduced vagal activity that only 5% of adjacent heart beats differ by more than 10 milliseconds, indicating an extremely low level of parasympathetic activity. In a healthy subject (and in the epilepsy patient when not experiencing a seizure), normal physiological activity (e.g., moderate walking) that likewise raises HR from 70 to 100 may result in more than 50% of adjacent heart beats differing by more than 10 milliseconds. Thus, in this hypothetical example, NN10 could potentially be used to distinguish between normal physical activity and an epileptic seizure. Stated more generally, appropriately low XX counts may be used to distinguish low but physiologically normal HRV from low and pathological HRV.

In the present invention, the value of XX can be either fixed programmatically before initiating operation of an epilepsy event detection algorithm, manually adjusted at periodic intervals after interrupting the algorithm operation, or dynamically adjusted during operation of the algorithm. For example, in one embodiment the value of XX can be manually established by a physician reviewing both a log of epilepsy events detected according to the present method and a log of epilepsy events detected by another technique, such as from an electroencephalogram (EEG) of the patient, and revising the value of XX to reduce the number of false positive and/or false negative event detections according to the present method. For example, if the present method detects more events than are detected from an EEG of the patient (i.e., false positive detections), the physician may increase XX; for another example, if the present method detects fewer events than are detected from an EEG of the patient, the physician may decrease XX. In one embodiment, XX is less than or equal to 40. In still other embodiments, XX may be selected as less than or equal to 35, 30, 25, 20, 15, 10, or even 5.

In another embodiment, the value of XX may be dynamically adjusted on an ongoing basis during operation of the algorithm. For example, the value of XX may be recalculated at a fixed or variable number of heart beats (e.g., every heart beat, every 2 beats, 4 beats, 5 beats, 10 beats, etc.). In one embodiment, XX is dynamically recalculated as a function of another HRV parameter. In a particular embodiment, XX is dynamically recalculated on an ongoing basis as a function of the standard deviation (SD) or root mean squared successive distances (RMSSD) of the patient's R-R interval stream. Suitable functions may include hyperbolic functions, exponential functions, parabolic functions, and other mathematical functions that incorporate the desired HRV function for adjusting XX.

The present inventor has discovered that adjusting the XX value based on another HRV parameter may address specificity issues from NNXX. This is because the discriminating power of NNXX is dependent upon existing sympathetic and parasympathetic activity levels, which in turn are strongly influenced by environmental factors and the patient's own cognitive, emotional, neurological and physiological status. Adjusting the value of XX may help ensure that the NNXX count provides maximal discrimination between epilepsy events (e.g., seizures or elevated seizure risk) and normal cardiac function in the presence of the patient's changing physical, neural, emotional, and cognitive states.

As a nonlimiting example, for some patients, XX values less than 20 may allow NNXX to distinguish between seizure (or elevated seizure risk) states and non-seizure states in resting, wakeful patients. Thus, an epileptic seizure may be preceded by a rapid decline in NN20 counts. On the other hand, the discriminatory power of NN20 in a variety of every-day conditions other than resting, wakeful states (e.g., working, commuting, sitting, walking, climbing stairs, in social contexts, etc) may vary significantly. For example, during intense exercise even persons without epilepsy may experience prolonged periods with no RR intervals varying by more than 5 milliseconds. In such cases, even XX values of 5 would be insufficient to distinguish between epileptic events and normal cardiac function on the basis of NN5 counts, because both epilepsy and non-epilepsy persons would have NN5 counts approaching zero. Similarly, for sleeping patients even NN50 counts may not be adequate to distinguish seizure events from non-seizure states, because elevated parasympathetic activity will produce many successive RR intervals exceeding 50 msec. Elevated NN50 counts for even epilepsy patients may occur during sleep, and thus during sleep, XX values even as high as 50 may be inadequate to distinguish epileptic events from normal physiological processes.

Adjusting the value of XX as a function of one or more HRV parameter(s) that vary with patient physical, neural, emotional, and/or cognitive states preserves or enhances the ability of NNXX to distinguish between epilepsy events and normal cardiac function. Using dynamic adjustment, epileptic seizures may be detected with XX values less than 5 or, for resting patients or patients with otherwise elevated parasympathetic activity, epileptic seizures may be detected with XX values exceeding 50 in some cases. Dynamic XX adjustment thus retains the predictive power of NNXX at widely varying levels of sympathetic and parasympathetic activity.

The mitigation of parameter specificity can be done by dynamic adjustment of coefficients in the equations for assessment of the various nonlinear and/or statistical parameters. For example, SampEn, SOD, and NNXX can be calculated as follows:

SampEn

A key parameter significantly affecting SampEn value is auto regression tolerance.

The dynamic adjustment of the tolerance for SampEn can be done as follows:

$$ToleranceSampEn = \sqrt{a+bx}$$

where:

ToleranceSampEn is a tolerance, r, in the SampEn equation:

$$SampEn(m, r, N) = -\ln\left(\frac{A^m(r)}{B^m(r)}\right)$$

x is RMSSD/SD continuously calculated for each window;
a is Tolerance Base value; and
b is Tolerance Coefficient value.

Values of a and b can be selected empirically. As an example, in one embodiment, a=64, b=1.

SOD

A key parameter affecting SOD is the value of the distribution Delta. Delta is the value of the jump, e.g. if Delta=10 then Similarity Of Distribution is calculated for sets of RR intervals, 1-10, 11-20, 21-30, etc.

Delta can be dynamically calculated as follows:

$$DeltaRR = \sqrt{a+bx}$$

where:

DeltaRR is the number is the number of cells in the histogram of the probability distribution, h in the SOD equation:

$$A(s) = \sum_{i=1}^{h} p_i(t)p_i(t+s)$$

x is RMSSD/SD;
a is DeltaRR Base; and
b is DeltaRR Coefficient.

Values of a and b can be selected empirically. As an example, in one embodiment, a=8, b=1.

NNXX

In one embodiment, the XX value can be dynamically adjusted using the equation as follows:

$$XX = \sqrt{a+bx}$$

where:

x is RMSSD (root mean squared successive distances) or SD (standard deviation);
a is XX Base; and
b is XX Coefficient.

Values of a and b can be selected empirically. As an example, in one embodiment, a=64, b=4.

The values of a and b can be selected by the person of ordinary skill in the art as a matter of routine experimentation with knowledge of the techniques described herein. In one embodiment, a is chosen so that $\sqrt{a}$ is less than the number of interbeat intervals in the sample. According to the foregoing discussion, the value of XX may be automatically adjusted either periodically or continually in a sliding or stepwise fashion to take into account the effects of non-pathological events or activities of the patient, and the effect of such events or activities on the patient's physical, neural, emotional, and/or cognitive states. By this method, the NNXX value used for epilepsy event detection may be automatically adjusted according to the current status of the patient's cardiac system.

As the value of XX is dynamically adjusted, the value of NNXX will be determined on an ongoing basis from the RR interval data stream using the above-noted formula for NNXX. Thus, using a 32 beat moving RR interval sample, the value of XX may vary from 10 to, for example 12 in moving from a first beat to the next beat, and NN10 may be calculated at the first beat and compared to the NNXX threshold, while NN12 is calculated at the next beat and compared to the NNXX threshold to detect whether or not an epilepsy event has occurred. It should be noted that, in some embodiments, the value of XX is maintained as a constant and the NNXX threshold for seizure detection is adjusted as a function of the second HRV parameter (instead of adjusting XX and NNXX).

As discussed above, the value of NNXX is calculated over a sample having a desired number of points within the sample. The size of the sample used will influence the burden of calculation on the medical device power source (such as a battery). In one embodiment, the at least one NNXX value is calculated over a first window comprising less than about 60 contiguous beats. In a particular embodiment, the at least one NNXX value is calculated over a first window comprising about 32 contiguous beats. In addition, the first window may comprise interpolated beats, if desired. In one embodiment, 32 contiguous beats, along with 7 interpolated beats between each actual beat, are used to calculate NNXX on a moving beat window basis. Smaller (e.g., 3) or larger (e.g., 15) numbers of interpolated beats may also be used between actual beats.

The NNXX value can be calculated after every beat, every second beat, every third beat, every fourth beat, every fifth beat, etc. A lower calculation frequency will reduce energy expenditure and heat production in the medical device, but will also give less frequent updates of NNXX. In one embodiment, the NNXX value is calculated after every fourth beat. In another embodiment, the NNXX value may be calculated on a time basis rather than on a heart beat basis, for example, the NNXX value may be calculated every second, every 2 seconds, every 5 seconds, etc.

For a given XX value (whether fixed or dynamically adjusted), the NNXX value is calculated. The NNXX value may then be compared to an NNXX threshold. "Threshold," as used herein, encompasses both a single value and a plurality of values. In one embodiment, for example, a single NNXX threshold 0.1 is used.

In another embodiment, a plurality of NNXX thresholds are used, for example 0.3, 0.25, 0.2, 0.15, and 0.1. The NNXX-to-threshold comparison may be used to determine a NNXX weighting factor (Weight$_{NNXX}$) for calculating a Weighted Risk Factor. In a particular embodiment, the comparison result is used to yield a weight value from 0 to 5, as follows:

| NNXX Value | Weight$_{NNXX}$ |
|---|---|
| NNXX > 0.3 | 0 |
| 0.25 < NNXX ≤ 0.3 | 1 |
| 0.2 < NNXX ≤ 0.25 | 2 |
| 0.15 < NNXX ≤ 0.2 | 3 |
| 0.1 < NNXX ≤ 0.15 | 4 |
| NNXX ≤ 0.1 | 5 |

Embodiments of the present invention also involve providing an output indicative of the occurrence of an epilepsy event based on the comparison of the NNXX value and the threshold(s). In one embodiment the output is provided based upon the NNXX-to-threshold comparison alone.

Although NNXX can be used alone in an epilepsy event detection algorithm, in one embodiment, the method further may comprise determining at least one regularity nonlinear analysis parameter and/or at least one predictability nonlinear analysis parameter based upon the beat sequence of the patient's heart and comparing the at least one regularity nonlinear analysis parameter to a first threshold and/or the at least one predictability nonlinear analysis parameter to a second threshold. Providing an output indicative of an epilepsy event may be based upon one, two or all three of the NNXX comparison, the regularity parameter comparison, and the predictability parameter comparison Determining the at least one regularity nonlinear analysis parameter and the at least one predictability nonlinear analysis parameter can be as previously described. Dynamic adjustment as a function of another HRV parameter, as previously described for XX values, may also be applied to one or both of the regularity and predictability parameters and/or thresholds.

As previously noted, the NNXX value may be compared to one or more thresholds to yield an NNXX weighting factor. Similarly, the regularity parameter and/or the predictability parameter may be compared to one or more regularity and predictability thresholds, respectively, to determine a regulatory parameter weighting factor (Weight$_{rp}$) and a predictability parameter weighting factor (Weight$_{pp}$). In one embodiment, comparing is to a plurality of first threshold values and second threshold values. For example, in one embodiment, where the at least one regularity nonlinear analysis parameter is sample entropy (SampEn) and the at least one predictability nonlinear analysis parameter is similarity of distribution (SOD), a regulatory parameter weight (Weight$_{SampEN}$) and a predictability parameter weight (Weight$_{SOD}$) may be determined as follows.

| SampEn Value | Weight$_{SampEN}$ |
|---|---|
| SampEn > 0.3 | 0 |
| 0.25 < SampEn ≤ 0.3 | 1 |
| 0.2 < SampEn ≤ 0.25 | 2 |
| 0.15 < SampEn ≤ 0.2 | 3 |
| 0.1 < SampEn ≤ 0.15 | 4 |
| SampEn ≤ 0.1 | 5 |

| SOD Value | Weight$_{SOD}$ |
|---|---|
| SOD ≤ 0.4 | 0 |
| 0.4 < SOD ≤ 0.5 | 1 |
| 0.5 < SOD ≤ 0.6 | 2 |
| 0.6 < SOD ≤ 0.7 | 3 |
| 0.7 < SOD ≤ 0.8 | 4 |
| SOD > 0.8 | 5 |

The weight factors determined in the tables above from NNXX, SampEn, and SOD can be used to determine a composite epilepsy Weighted Risk Factor that may be used to determine whether or not an epilepsy event (such as an unstable brain state, a brain state indicative of an elevated probability of a seizure, a brain state indicative of an impending seizure, an aura or a seizure) has been detected. In providing the detection output, the multiple weight factors can be considered in any desirable manner. In one embodiment, an epilepsy event Weighted Risk Factor (WRF) is calculated as the simple sum of the NNXX weighting factor, the regulatory parameter weighting factor, and the predictability parameter weighting factor:

$$WRF = Weight_{NNXX} + Weight_{SampEN} + Weight_{SOD}$$

and a WRF≥14 is an output indicative of at least one of an unstable brain state, a brain state indicative of an elevated probability of a seizure, a brain state indicative of an impending seizure, an aura or a seizure.

Other techniques for estimating the likelihood or occurrence of an epileptic event from one or more of NNXX, a regularity parameter, and a predictability parameter can be used. In another embodiment, an epilepsy event Risk Factor (RF) is calculated from individual Risk Factors from NNXX (RF$_{NNXX}$), the regularity parameter (e.g., RF$_{SampEN}$), and the predictability parameter (e.g., RF$_{SOD}$). The individual Risk Factors for NNXX, predictability and regularity may be calculated as non-linear functions of the values of the NNXX, regularity and predictability parameters. Nonlimiting examples of non-linear functions include, but are not limited to, exponential, parabolic or hyperbolic functions. Other nonlinear functions are known to the person of ordinary skill in the art In a particular embodiment, the individual risk factors may be calculated from the underlying parameters as follows:

$$RF_{NNXX} = (e^{x1*(1-NNXX)} - 1)/(e^{x2*(1-NNXX)} + 4) * k$$

wherein e is the base of the natural logarithm (about 2.718). In one embodiment, x1=4, x2=1.5, and k=22. Further, if RF$_{NNXX}$>100, RF$_{NNXX}$ is set to 100, and if RF$_{NNXX}$<0, RF$_{NNXX}$ is set to 0.

$$RF_{SOD} = (e^{x1*(1-SOD)} - 1)/(e^{x2*(1-SOD)} + 4) * k$$

In one embodiment, x1=2.2, x2=3, and k=320. Further, if RF$_{SOD}$>100, RF$_{SOD}$ is set to 100, and if RF$_{SOD}$<0, RF$_{SOD}$ is set to 0.

$$RF_{SampEN} = (e^{x1*(1-SampEn)} - 1)/(e^{x2*(1-SampEn)} + 4) * k$$

In one embodiment, x1=4, x2=1.5, and k=20. Further, if $RF_{SampEN}$>100, $RF_{SampEN}$ is set to 100, and if $RF_{SampEN}$<0 or SampEn>0.95, $RF_{SampEN}$ is set to 0.

From the individual risk factors, the epilepsy event Risk Factor (RF) may be determined from the formula:

$$RF=RF_{NNXX}+RF_{SOD}+RF_{SampEN}.$$

The RF can be taken directly (RFa, wherein RFa=$RF_{NNXX}$+$RF_{SOD}$+$RF_{SampEN}$) or further modified (RFc), such as by reference to a baseline risk factor based on a longer time window. In one embodiment, RFc=RFa/√(RFbaseline). RFbaseline can be calculated, in one embodiment, as a mean value of n RFa values preceding current RFa. In another embodiment, RFbaseline can be calculated as a median value of n RFa values preceding current RFa. More generally, the RFbaseline can be calculated as a statistical measure of central tendency (or location value) in a distribution of n values, including (in addition to the mean and median noted above, a first or third quartile, or a desired percentile value in a distribution function. In the foregoing instances, the mean and/or median values used to calculate RFbaseline can in addition be time weighted using, for example, exponential forgetting factors. The value of n, as well as appropriate values for x1, x2, and k for the individual risk factor formulas, can be selected by the person of ordinary skill in the art as a matter of routine experimentation in light of the present disclosure. In one embodiment, n is 16.

In addition to the steps set forth above, in one embodiment, the method further comprises taking a responsive action selected from warning, logging the time of the seizure, computing and storing one or more seizure event indices, and treating the epilepsy event based upon the comparing of one or more of the at least one regularity nonlinear analysis parameter to a first threshold, the at least one predictability nonlinear analysis parameter to a second threshold, and the at least one NNXX value to a third threshold. In a further embodiment, the responsive action is treating, and treating comprises at least one of applying an electrical signal to a neural structure of a patient and delivering a drug to a patient. In still a further embodiment, applying an electrical signal to the neural structure comprises applying the electrical signal to at least one of a brain structure of the patient, a cranial nerve of a patient, a spinal cord of a patient, a sympathetic nerve structure of the patient, or a peripheral nerve of the patient. These particular embodiments of taking a responsive action, treating, and applying an electrical signal to a neural structure are substantially the same as those discussed above.

Although not so limited, a system capable of implementing embodiments of the present invention is described below. FIG. 1A depicts a stylized implantable medical system (IMD) 100 for implementing one or more embodiments of the present invention. An electrical signal generator 110 is provided, having a main body 112 comprising a case or shell with a header 116 for connecting to an insulated, electrically conductive lead assembly 122. The generator 110 is implanted in the patient's chest in a pocket or cavity formed by the implanting surgeon just below the skin (indicated by a dotted line 145), similar to the implantation procedure for a pacemaker pulse generator.

A nerve electrode assembly 125, preferably comprising a plurality of electrodes having at least an electrode pair, is conductively connected to the distal end of the lead assembly 122, which preferably comprises a plurality of lead wires (one wire for each electrode). Each electrode in the electrode assembly 125 may operate independently or alternatively, may operate in conjunction with the other electrodes. In one embodiment, the electrode assembly 125 comprises at least a cathode and an anode. In another embodiment, the electrode assembly comprises one or more unipolar electrodes.

Lead assembly 122 is attached at its proximal end to connectors on the header 116 of generator 110. The electrode assembly 125 may be surgically coupled to the vagus nerve 127 in the patient's neck or at another location, e.g., near the patient's diaphragm or at the esophagus/stomach junction. Other (or additional) cranial nerves such as the trigeminal and/or glossopharyngeal nerves may also be used to deliver the electrical signal in particular alternative embodiments. In one embodiment, the electrode assembly 125 comprises a bipolar stimulating electrode pair 126, 128 (i.e., a cathode and an anode). Suitable electrode assemblies are available from Cyberonics, Inc., Houston, Tex., USA as the Model 302 electrode assembly. However, persons of skill in the art will appreciate that many electrode designs could be used in the present invention. In one embodiment, the two electrodes are wrapped about the vagus nerve, and the electrode assembly 125 may be secured to the vagus nerve 127 by a spiral anchoring tether 130 such as that disclosed in U.S. Pat. No. 4,979,511 issued Dec. 25, 1990 to Reese S. Terry, Jr. Lead assembly 122 may be secured, while retaining the ability to flex with movement of the chest and neck, by a suture connection to nearby tissue (not shown).

In alternative embodiments, the electrode assembly 125 may comprise temperature sensing elements and/or heart rate sensor elements. Other sensors for other body parameters may also be employed. Both passive and active stimulation may be combined or delivered by a single IMD according to the present invention. Either or both modes may be appropriate to treat a specific patient under observation.

Figure 1B:
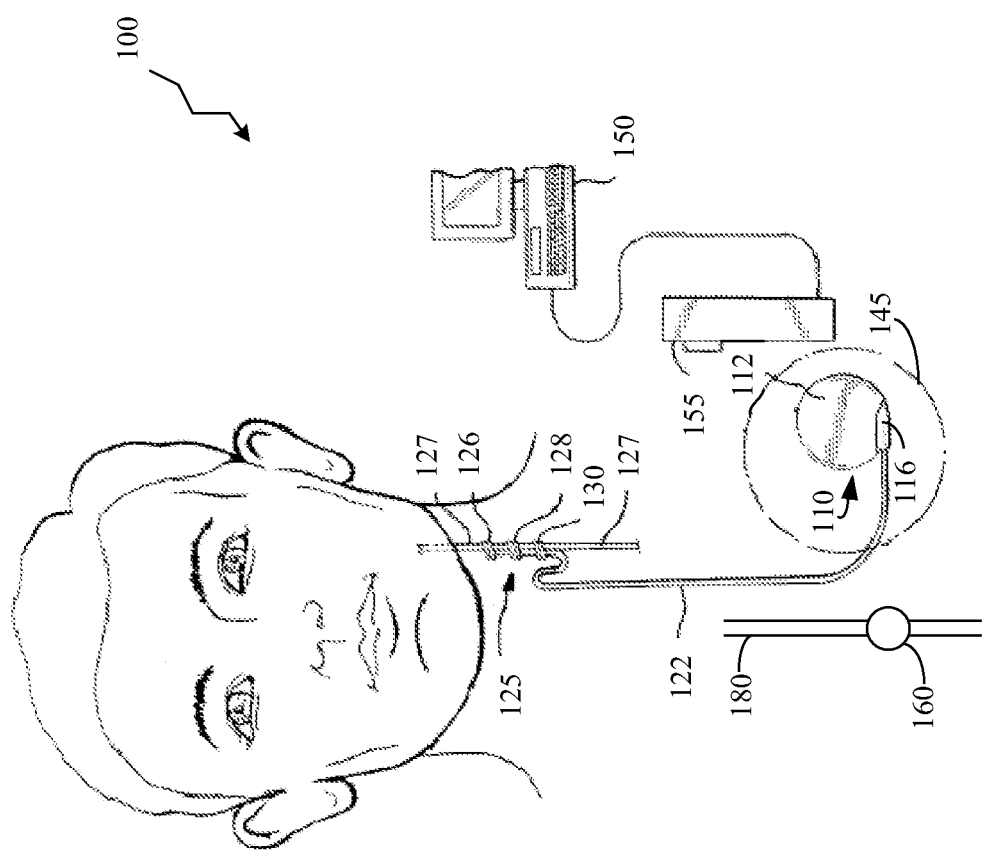
FIG. 1B provides a stylized diagram of an implantable medical device implanted into a patient's body for providing a therapeutic electrical signal to a neural structure of the patient's body, in accordance with one illustrative embodiment of the present invention.
Figure 1C:
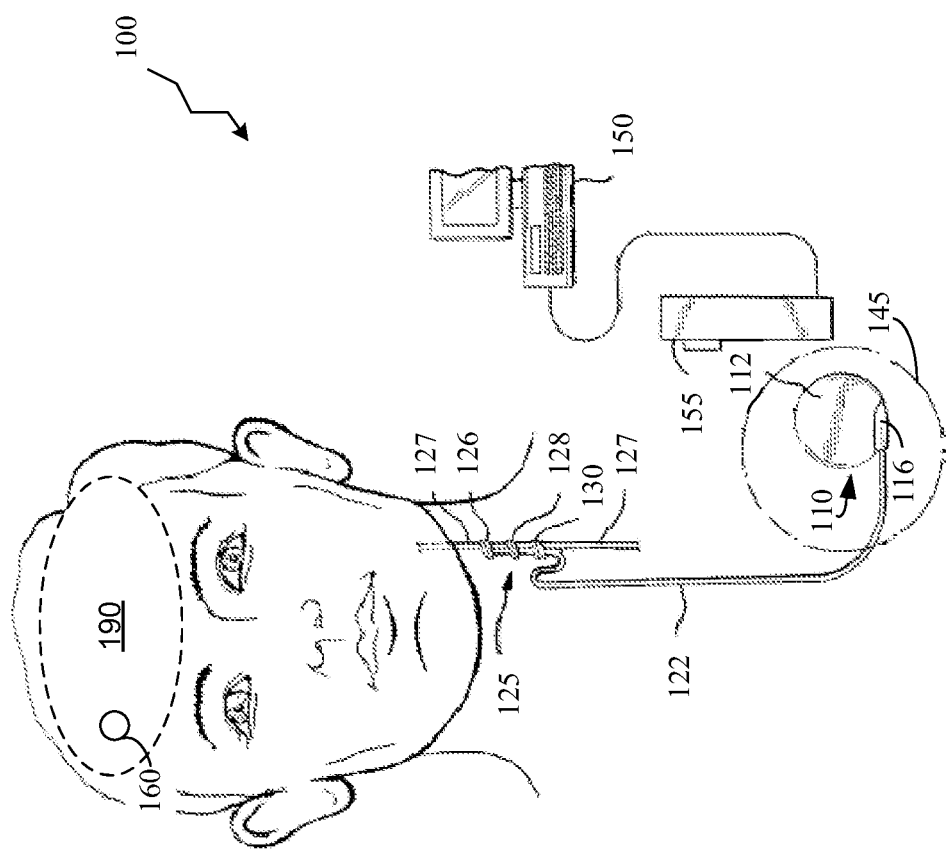
FIG. 1C provides a stylized diagram of an implantable medical device implanted into a patient's body for providing a therapeutic electrical signal to a neural structure of the patient's body, in accordance with one illustrative embodiment of the present invention.

In alternative embodiments, the implantable medical device system further comprises an electrical stimulator comprising an electrode 160 (not to scale) adapted to be coupled to the spinal cord 180 (FIG. 1B) or to a region of the brain 190 (FIG. 1C). The physician can select precise locations for coupling to the spinal cord 180 or brain 190 based on his or her observations of the patient's medical condition, among other values. In various embodiments, the implantable medical device system may comprise one, two, or three of the IMD 100, the spinal cord stimulator, and the brain stimulator.

The electrical pulse generator 110 may be programmed with an external device (ED) such as computer 150 using programming software known in the art. A programming wand 155 may be coupled to the computer 150 as part of the ED to facilitate radio frequency (RF) communication between the computer 150 and the pulse generator 110. The programming wand 155 and computer 150 permit non-invasive communication with the generator 110 after the latter is implanted. In systems where the computer 150 uses one or more channels in the Medical Implant Communications Service (MICS) bandwidths, the programming wand 155 may be omitted to permit more convenient communication directly between the computer 150 and the pulse generator 110.

Turning now to FIG. 2, a block diagram depiction of a medical device 200 is provided, in accordance with one illustrative embodiment of the present invention.

In some embodiments, the medical device 200 may be implantable (such as implantable electrical signal generator 110 from FIG. 1), while in other embodiments the medical device 200 may be completely external to the body of the patient.

Figure 2A:
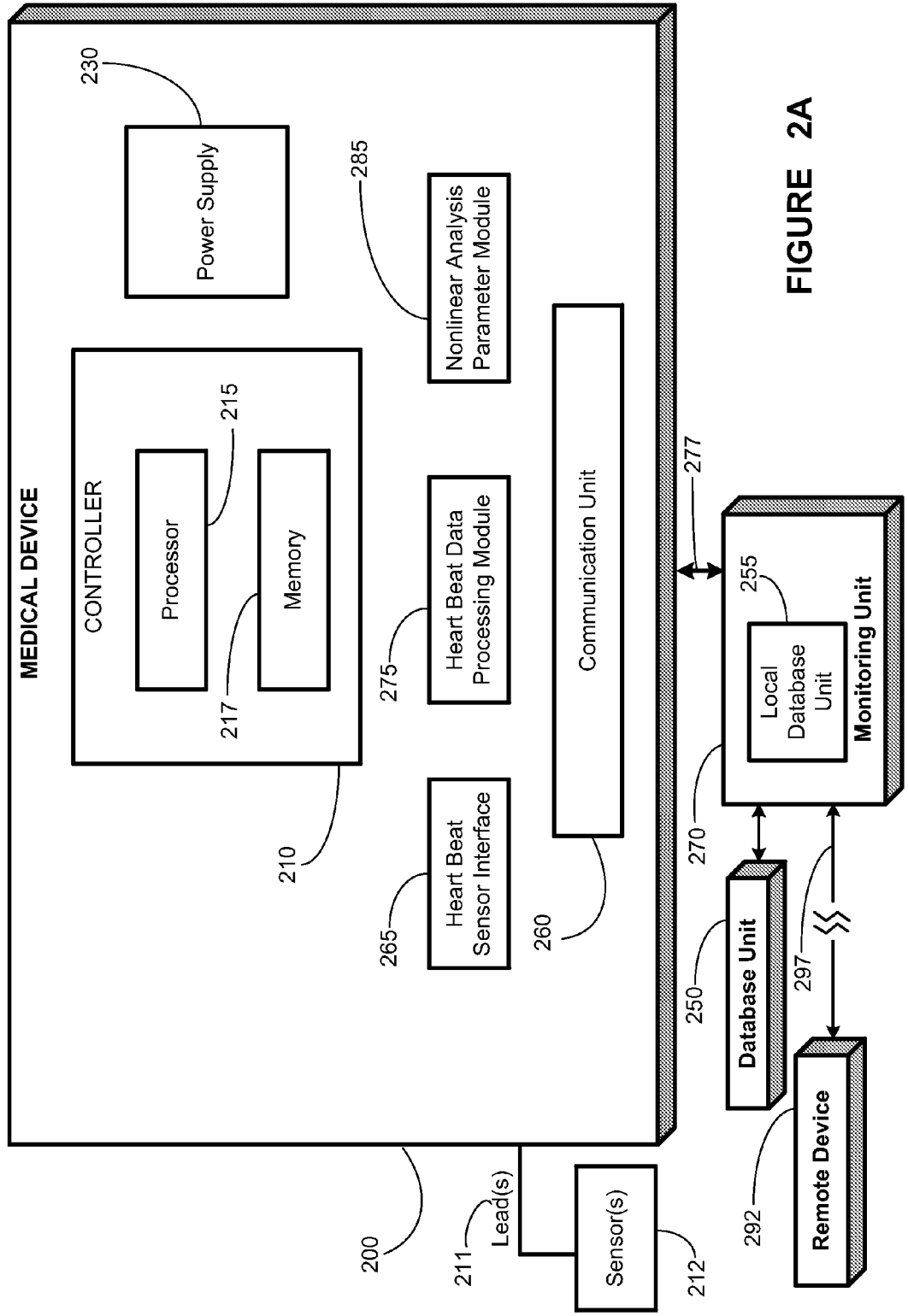
FIGS. 2A-2D are block diagrams of a medical device system that includes a medical device and an external device, in accordance with four illustrative embodiments of the present invention.

The medical device 200 (such as generator 110 from FIG. 1) may comprise a controller 210 capable of controlling various aspects of the operation of the medical device 200. The controller 210 is capable of receiving internal data or external data, and in one embodiment, is capable of causing a stimulation unit 220 (FIGS. 2B, 2D) to generate and deliver an electrical signal to target tissues of the patient's body for treating a medical condition. For example, the controller 210 may receive manual instructions from an operator externally, or may cause the electrical signal to be generated and delivered based on internal calculations and programming. In other embodiments, the medical device 200 does not comprise a stimulation unit 220 (FIGS. 2A, 2C). In either embodiment, the controller 210 is capable of affecting substantially all functions of the medical device 200.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise one or more of random access memory (RAM), dynamic random access memory (DRAM), electrically erasable programmable read-only memory (EEPROM), flash memory, etc.

Figure 2B:
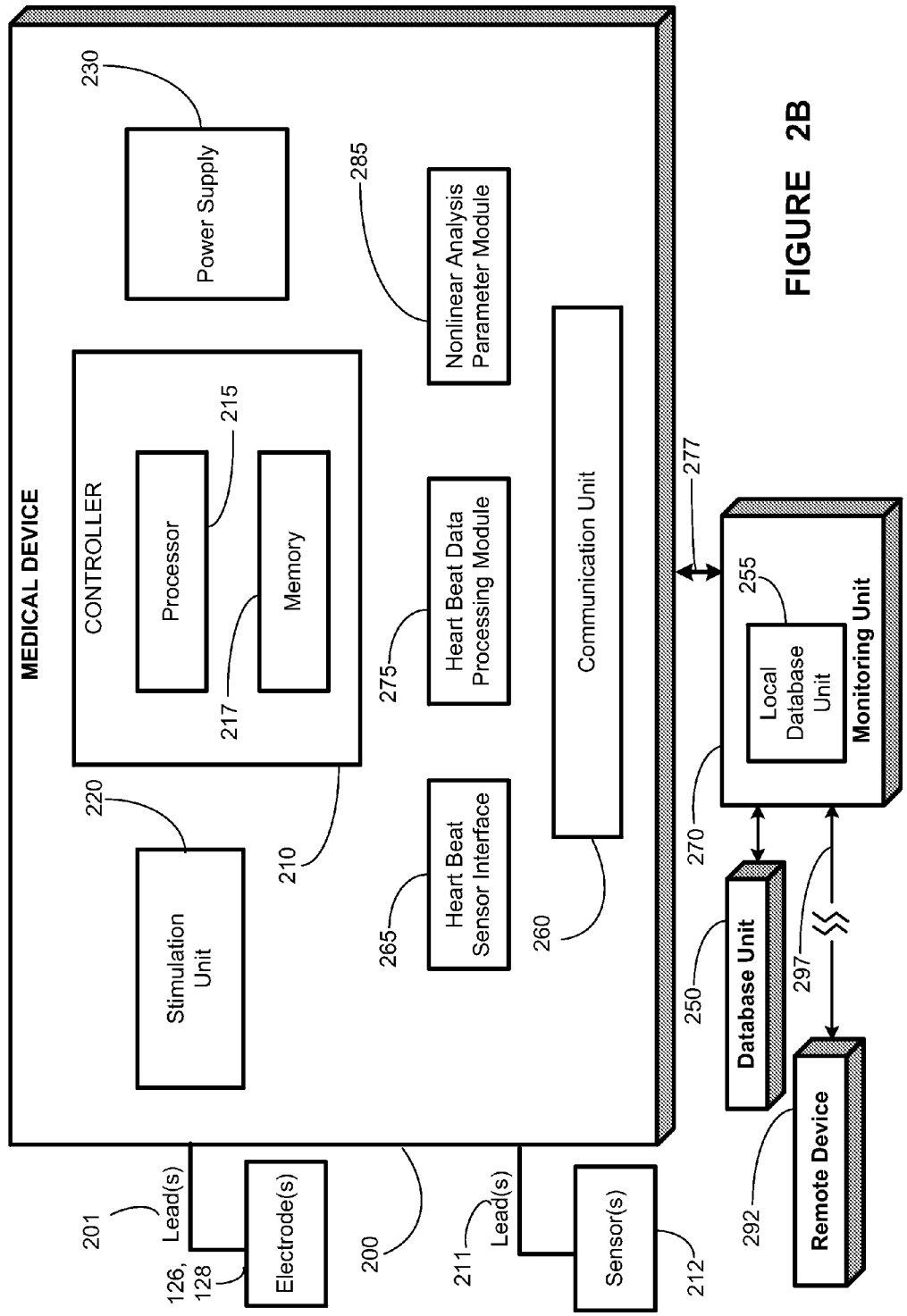
Figure 2C:
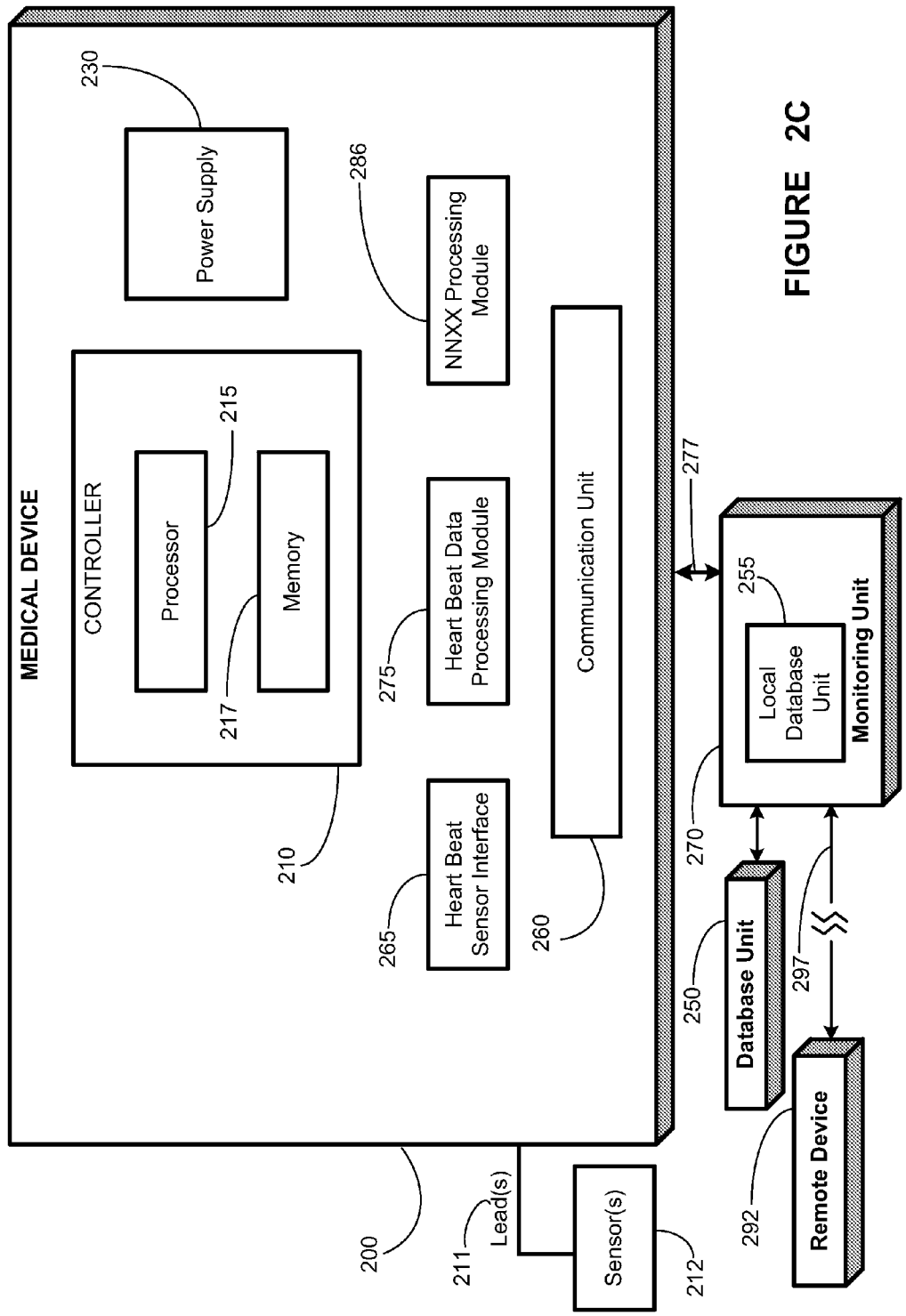
Figure 2D:
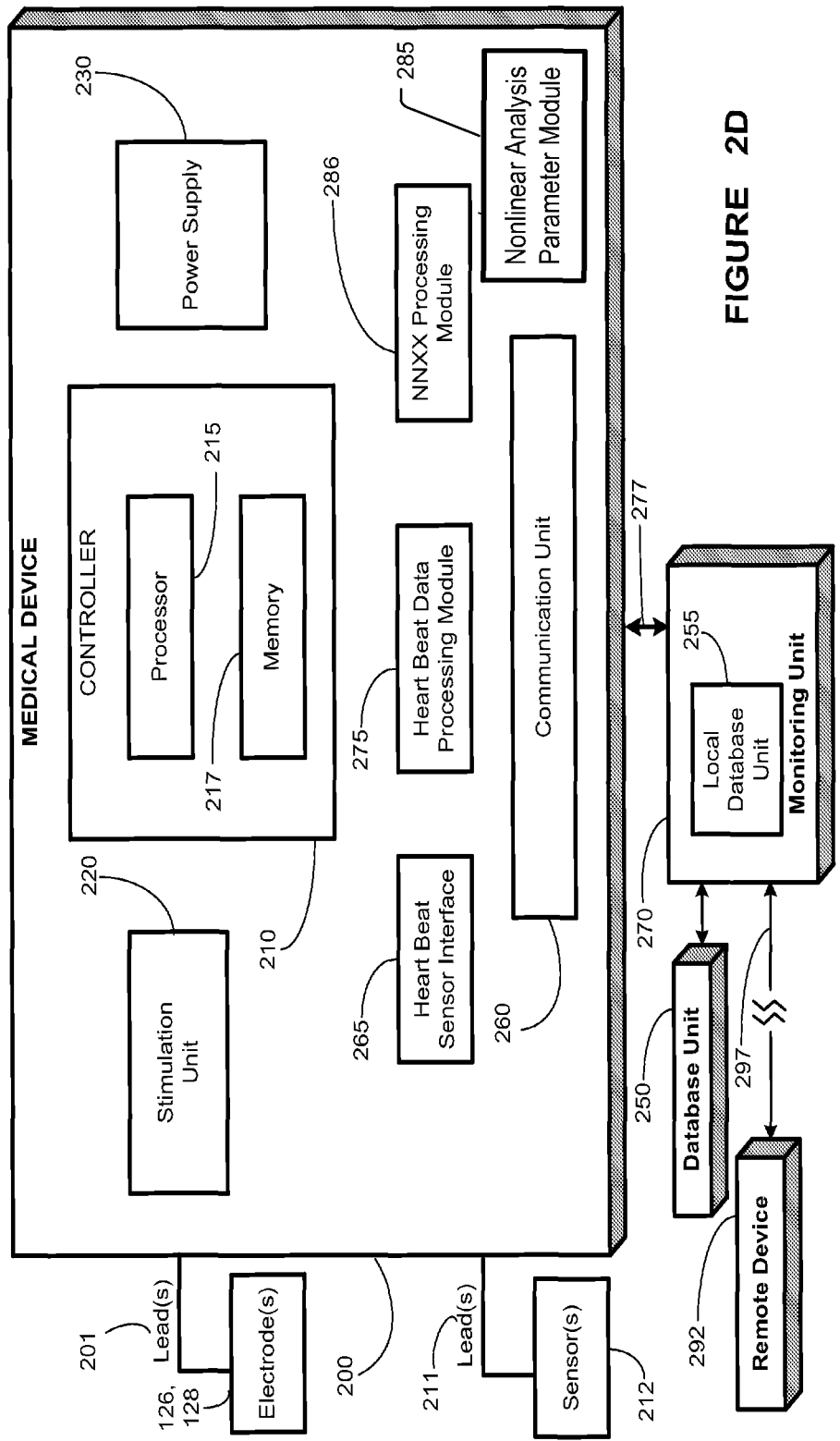

As stated above, in one embodiment, the medical device 200 may also comprise a stimulation unit 220 capable of generating and delivering electrical signals to one or more electrodes 126, 128 via leads 201 (FIGS. 2B, 2D). A lead assembly such as lead assembly 122 (FIG. 1) may be coupled to the medical device 200. Therapy may be delivered to the leads 201 comprising the lead assembly 122 by the stimulation unit 220 based upon instructions from the controller 210. The stimulation unit 220 may comprise various circuitry, such as electrical signal generators, impedance control circuitry to control the impedance "seen" by the leads, and other circuitry that receives instructions relating to the delivery of the electrical signal to tissue. The stimulation unit 220 is capable of delivering electrical signals over the leads 201 comprising the lead assembly 122. As should be apparent, in certain embodiments, the medical device 200 does not comprise a stimulation unit 220, lead assembly 122, or leads 201. In particular, although FIGS. 2B and 2D are illustrated with stimulation unit 220, leads 201 and electrodes 126, 128, in alternative embodiments, these structures and the stimulation function enabled thereby may be omitted.

In other embodiments, a lead 201 is operatively coupled to an electrode, wherein the electrode is adapted to couple to at least one of a portion of a brain structure of the patient, a cranial nerve of a patient, a spinal cord of a patient, a sympathetic nerve structure of the patient, or a peripheral nerve of the patient.

The medical device 200 may also comprise a power supply 230. The power supply 230 may comprise a battery, voltage regulators, capacitors, etc., to provide power for the operation of the medical device 200, including delivering the therapeutic electrical signal. The power supply 230 comprises a power source that in some embodiments may be rechargeable. In other embodiments, a non-rechargeable power source may be used. The power supply 230 provides power for the operation of the medical device 200, including electronic operations and the electrical signal generation and delivery functions. The power supply 230 may comprise a lithium/thionyl chloride cell or a lithium/carbon monofluoride (LiCFx) cell if the medical device 200 is implantable, or may comprise conventional watch or 9V batteries for external (i.e., non-implantable) embodiments. Other battery types known in the art of medical devices may also be used.

The medical device 200 may also comprise a communication unit 260 capable of facilitating communications between the medical device 200 and various devices. In particular, the communication unit 260 is capable of providing transmission and reception of electronic signals to and from a monitoring unit 270, such as a handheld computer or PDA that can communicate with the medical device 200 wirelessly or by cable. The communication unit 260 may include hardware, software, firmware, or any combination thereof.

The medical device 200 may also comprise one or more sensor(s) 212 coupled via sensor lead(s) 211 to the medical device 200. The sensor(s) 212 are capable of receiving signals related to a physiological parameter, such as the patient's heart beat, and delivering the signals to the medical device 200. In one embodiment, the sensor(s) 212 may be the same as implanted electrode(s) 126, 128 (FIG. 1). In other embodiments, the sensor(s) 212 are separate structures that may be placed on the patient's skin, such as over the patient's heart or elsewhere on the patient's torso. It will be appreciated by persons of skill in the art that in some embodiments, lead 211 may be omitted and the medical device 200 may communicate wirelessly with sensor 212.

In one embodiment, the medical device 200 may comprise a heart beat sensor interface 265 that is capable of receiving signals related to the patient's heart beat from the sensor(s) 212. The heart beat sensor interface 265 may be capable of performing any necessary or suitable amplifying, filtering, and performing analog-to-digital (A/D) conversions to prepare the signals for downstream processing. The heart beat sensor interface, in one embodiment, may comprise software module(s) that are capable of performing various interface functions, filtering functions, etc., to process heart rate signals. In another embodiment the heartbeat sensor interface 265 may comprise hardware circuitry that is capable of performing these functions. In yet another embodiment, the heartbeat sensor interface 265 may comprise hardware, firmware, software and/or any combination thereof. A more detailed illustration of the heartbeat sensor interface 265 is provided in FIG. 3A and accompanying description below.

The heartbeat sensor interface 265 is capable of receiving heartbeat signals and providing the signal to a heart beat data processing module 275. Based upon the signals processed by the heart beat sensor interface 265, a heart beat data processing module 275 may determine various properties of the patient's heart beat time series and store such properties or forward them on for further processing/analysis. In one embodiment, the heart beat data processing module 275 is capable of processing the heart beat into various components such that information relating to an epilepsy event is provided. For example, the heart beat data processing module 275 is capable of processing the heart beat signals into a form such that various nonlinear analysis parameters described herein, which are indicative of an acute physiological event, may be determined. For example, parameters such as SampEn and SOD that may be indicative of an increased risk of an epileptic seizure may be determined by the heart beat data processing module 275. Further description of the heart beat data processing module 275 is provided in FIG. 3B and accompanying description below.

Moreover, the medical device 200 may also comprise a nonlinear analysis module 285 (FIGS. 2A, 2B, 2D). The nonlinear analysis module 285 is capable of performing chaos analysis of the data derived from the heart beat signal. Further description of the nonlinear analysis module 285 is provided in FIG. 4 and accompanying description below.

For another example, a NNXX value that may be indicative of an increased risk of an epileptic seizure may be determined by a NNXX processing module 286 (FIGS. 2C, 2D). Further description of the NNXX processing module 286 is provided in FIG. 14 and accompanying description below.

In addition to components of the medical device 200 described above, an implantable medical system may comprise a storage unit to store an indication of at least one of epilepsy event (e.g., a seizure or an increased risk of a seizure). The storage unit may be the memory 217 of the medical device 200, another storage unit of the medical device 200, or an external database, such as the local database unit 255 or a remote database unit 250. The medical device 200 may communicate the indication via the communications unit 260. Alternatively or in addition to an external database, the medical device 200 may be adapted to communicate the indication to at least one of a patient, a caregiver, or a healthcare provider.

In various embodiments, one or more of the units or modules described above may be located in a monitoring unit 270 or a remote device 292, with communications between that unit or module and a unit or module located in the medical device 200 taking place via communication unit 260. For example, in one embodiment, the nonlinear analysis module 285 may be external to the medical device 200, e.g., in a monitoring unit 270. Locating the nonlinear analysis module 285 outside the medical device 200 may be advantageous if the nonlinear analysis parameter calculation is computationally intensive, in order to reduce energy expenditure and heat generation in the medical device 200 or to expedite calculation of the at least one nonlinear analysis parameter.

The monitoring unit 270 may be a device that is capable of transmitting and receiving data to and from the medical device 200. In one embodiment, the monitoring unit 270 is a computer system capable of executing a data-acquisition program. The monitoring unit 270 may be controlled by a healthcare provider, such as a physician, at a base station in, for example, a doctor's office. In alternative embodiments, the monitoring unit 270 may be controlled by a patient in a system providing less interactive communication with the medical device 200 than another monitoring unit 270 controlled by a healthcare provider. Whether controlled by the patient or by a healthcare provider, the monitoring unit 270 may be a computer, preferably a handheld computer or PDA, but may alternatively comprise any other device that is capable of electronic communications and programming, e.g., hand-held computer system, a PC computer system, a laptop computer system, a server, a personal digital assistant (PDA), an Apple-based computer system, a cellular telephone, etc. The monitoring unit 270 may download various parameters and program software into the medical device 200 for programming the operation of the medical device, and may also receive and upload various status conditions and other data from the medical device 200. Communications between the monitoring unit 270 and the communication unit 260 in the medical device 200 may occur via a wireless or other type of communication, represented generally by line 277 in FIGS. 2A-2D. This may occur using, e.g., wand 155 (FIG. 1) to communicate by RF energy with an implantable signal generator 110. Alternatively, the wand may be omitted in some systems, e.g., systems in which the MD 200 is non-implantable, or implantable systems in which monitoring unit 270 and MD 200 operate in the MICS bandwidths.

In one embodiment, the monitoring unit 270 may comprise a local database unit 255. Optionally or alternatively, the monitoring unit 270 may also be coupled to a database unit 250, which may be separate from monitoring unit 270 (e.g., a centralized database wirelessly linked to a handheld monitoring unit 270). The database unit 250 and/or the local database unit 255 are capable of storing various patient data. This data may comprise patient parameter data acquired from a patient's body and/or therapy parameter data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions (e.g., programming parameters for a responsive therapy and/or setting thresholds for one or more event detection parameters) using the monitoring unit 270, which may include obtaining and/or analyzing data from the medical device 200 and/or data from the database unit 250 and/or the local database unit 255. The database unit 250 and/or the local database unit 255 may store various patient data.

One or more of the blocks illustrated in the block diagram of the medical device 200 in FIGS. 2A-2D, may comprise hardware units, software units, firmware units, or any combination thereof. Additionally, one or more blocks illustrated in FIGS. 2A-2D may be combined with other blocks, which may represent circuit hardware units, software algorithms, etc. Additionally, any number of the circuitry or software units from the various blocks illustrated in FIGS. 2A-2D may be combined into a programmable device, such as a field programmable gate array, an ASIC device, etc.

The medical device system of one embodiment of the present invention provides for software module(s) that are capable of acquiring, storing, and processing various forms of data, such as patient data/parameters (e.g., physiological data, side-effects data, such as heart rate, breathing rate, brain-activity parameters, disease progression or regression data, quality of life data, etc.) and therapy parameter data. Therapy parameters may include, but are not limited to, electrical signal parameters that define therapeutic electrical signals delivered by the medical device in response to the detection of an epilepsy event, medication parameters and/or any other therapeutic treatment parameter. Therapy parameters for a therapeutic electrical signal may also include, but are not limited to, a current amplitude, a pulse width, a frequency, an on-time, an off-time, etc.

In one embodiment, the present invention may include coupling of at least one electrode to each of two or more cranial nerves. (In this context, two or more cranial nerves mean two or more nerves having different names or numerical designations, and do not refer to the left and right versions of a particular nerve). In one embodiment, at least one electrode may be coupled to either or both vagus nerves or a branch of either or both vagus nerves. The term "operatively" coupled may include directly or indirectly coupling. Each of the nerves in this embodiment or others involving two or more cranial nerves may be stimulated according to particular activation modalities that may be independent between the two nerves.

Returning to systems for providing cranial nerve stimulation, such as that shown in FIG. 1, and as stated above, alternatively or in addition to a responsive (i.e., closed-loop) treatment, if any, cranial nerve stimulation may be provided on a continuous or open-loop basis to alleviate chronic aspects of the patient's medical disorder. Where cranial nerve stimulation is provided based in an open-loop setting solely on programmed off-times and on-times, the stimulation may be referred to as passive, inactive, or non-feedback stimulation. In contrast, stimulation may be triggered by one or more feedback loops according to changes in the body or mind of the patient. This stimulation may be referred to as active or feedback-loop stimulation. In one embodiment, feedback-loop stimulation may be manually-triggered stimulation, in which the patient manually causes the activation of a pulse burst outside of the programmed on-time/off-time cycle. The patient may manually activate an implantable signal generator 110 to stimulate the cranial nerve, such as vagus nerve 127, to treat an acute episode of a medical condition, e.g., a seizure. The patient may also be permitted to alter the intensity of the signals applied to the cranial nerve within limits established by the physician.

Patient activation of an medical device 100 may involve use of an external control magnet for operating a reed switch in an implanted device, for example. Certain other techniques of manual and automatic activation of implantable medical devices are disclosed in U.S. Pat. No. 5,304,206 to Baker, Jr., et al. ("the '206 patent"), hereby incorporated by reference in its entirety. According to the '206 patent, means for manually activating or deactivating the electrical signal generator 110 may include a sensor such as piezoelectric element mounted to the inner surface of the generator case and adapted to detect light taps by the patient on the implant site. One or more taps applied in fast sequence to the skin above the location of the electrical signal generator 110 in the patient's body may be programmed into the implanted medical device 100 as a signal for intensification of the electrical signal. Two taps spaced apart by a slightly longer duration of time may be programmed into the medical device 100 to indicate a desire to de-intensify the electrical signal. The patient may be given limited control over operation of the device to an extent which may be determined by the program or entered by the attending physician. The patient may also activate the medical device 100 using other suitable techniques or apparatus.

In one embodiment, the medical device 200 may also be capable of detecting a manual input from the patient. The manual input may include a magnetic signal input, a tap input, a wireless data input to the medical device 200, etc.

Figure 3A:
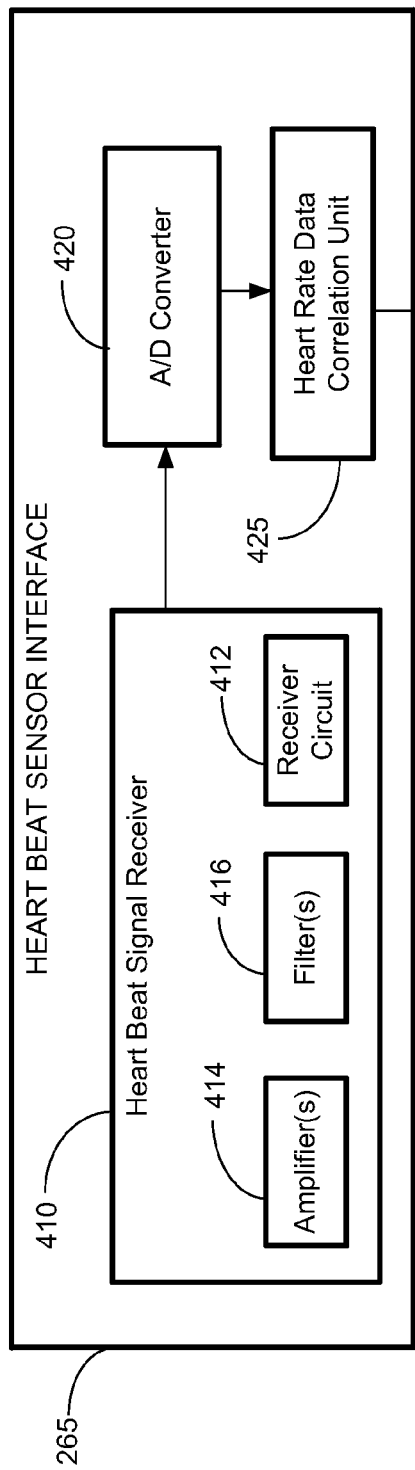
FIG. 3A is a stylized block diagram of a heart beat sensor interface of a medical device, in accordance with one illustrative embodiment of the present invention.

Turning now to FIG. 3A, a more detailed stylized depiction of the heart beat sensor interface 265 of FIGS. 2A-2D, in accordance with one illustrative embodiment of the present invention is depicted. In one embodiment, the heart beat sensor interface 265 comprises a heart rate signal receiver 410, an analog-to-digital converter (A/D Converter) 420, and a heart beat data correlation unit 425. The heart rate signal receiver 410 is capable of receiving the signals from the sensor(s) 212 via receiver circuit 412. The signal that is received by the receiver circuit 412 is processed and filtered to enable the data to be further analyzed and/or processed for detection of an epilepsy event.

The heart rate signal receiver 410 may comprise amplifier(s) 414 and filter(s) 416. The amplifiers 414 are capable of buffering and amplifying the input signals received by the receiver circuit 412. In many cases, the heart beat signal may be attenuated and may be characterized by significantly low amplitude responses and signal noise. The amplifier(s) 414 are capable of buffering (amplification by unity) and amplifying the signals for further processing. In one embodiment, the amplifier 414 may comprise op amp circuit(s), digital amplifier(s), buffer amplifiers, and/or the like.

The heart beat signal receiver 410 may also comprise one or more filters 416. The filters 416 may comprise analog filter(s), digital filter(s), filters implemented by digital signal processing (DSP) means or methods, etc. The amplified and buffered heart beat signal may be filtered to remove various noise signals residing on the heart beat signal. The filter 416, for example, is capable of filtering out various noise signals caused by external magnetic fields, electrical fields, noise resulting from physiological activity, etc. Filtering, signal noise due to breathing or other signals produced by the patient's body may be filtered.

The heart beat signal receiver 410 provides amplified, filtered signals to the A/D converter 420. The A/D converter 420 performs an analog-to-digital conversion for further processing of the heart beat signal. The A/D converter 420 may be one type of a plurality of converter types with various accuracies, such as an 8-bit converter, a 12-bit converter, a 24-bit converter, a 32-bit converter, a 64-bit converter, a 128-bit converter, a 256-bit converter, etc. The converted digital signal is then provided to a heart beat data correlation unit 425. In an alternative embodiment, the A/D conversion may be performed prior to filtering or signal processing of the heart beat signal. The converted digital signal is then provided to a heart beat data correlation unit 425.

The heart beat data correlation unit 425 is capable of organizing, correlating, stacking, and otherwise processing the digitized, buffered, and filtered heart rate data. The heart beat correlation unit 425 is capable of correlating and organizing the digitized heart beat signal. The correlation unit 425 may correlate various time stamps with the heart beat signal to provide a time of beat sequence of the patient's heart. Further, the heart beat data correlation unit 425 is capable of correlating various physiological events to the heart beat data. The digital signals issuing from the heart beat data correlation unit 425 may then be forwarded to the heart beat data processing module 275 depicted in FIGS. 2A-2D.

Figure 3B:
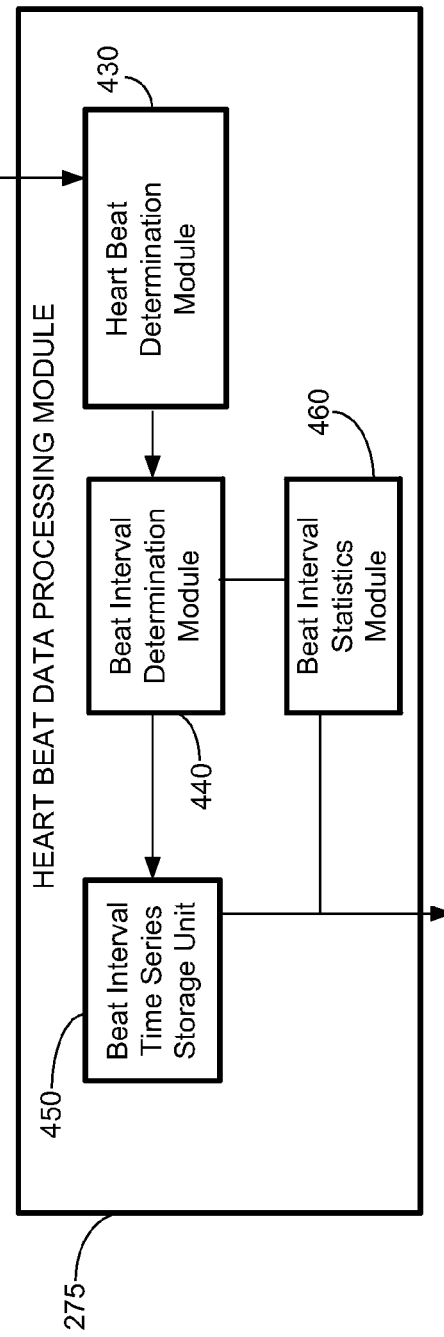
FIG. 3B is a stylized block diagram of a heart beat data processing module of a medical device, in accordance with one illustrative embodiment of the present invention.

Turning now to FIG. 3B, a more detailed stylized depiction of the heart beat data processing module 275 of FIGS. 2A-2D, in accordance with one illustrative embodiment of the present invention is depicted. The heart beat data processing module 275 may comprise a heart beat determination module 430, a beat interval determination module 440, a beat interval time series storage unit 450, and a beat interval statistics module 460. The heart beat data processing module 275 may determine heart beats as they appear in the time series of signals via the heart beat determination module 430. For example, heart beat determination module 430 may characterize certain data points in the time series of signals as corresponding to the start, the peak, or the end of an R-wave of a patient's cardiac cycle.

Once heart beats are determined from the time series of signals, the beat interval determination module 440 may determine the interval between consecutive beats ("beat interval") and forward this information to beat interval time series storage 450. From the determined beat interval and/or the time series thereof, the beat interval statistics module 460 can determine various statistical (non-chaos) values of the beat interval time series, e.g., mean, median, or standard deviation, among others, for various timescales (e.g., 5 minutes, 1 hour, 24 hours). The beat interval time series, the statistical values thereof, or both may be used for further processing.

Figure 4:
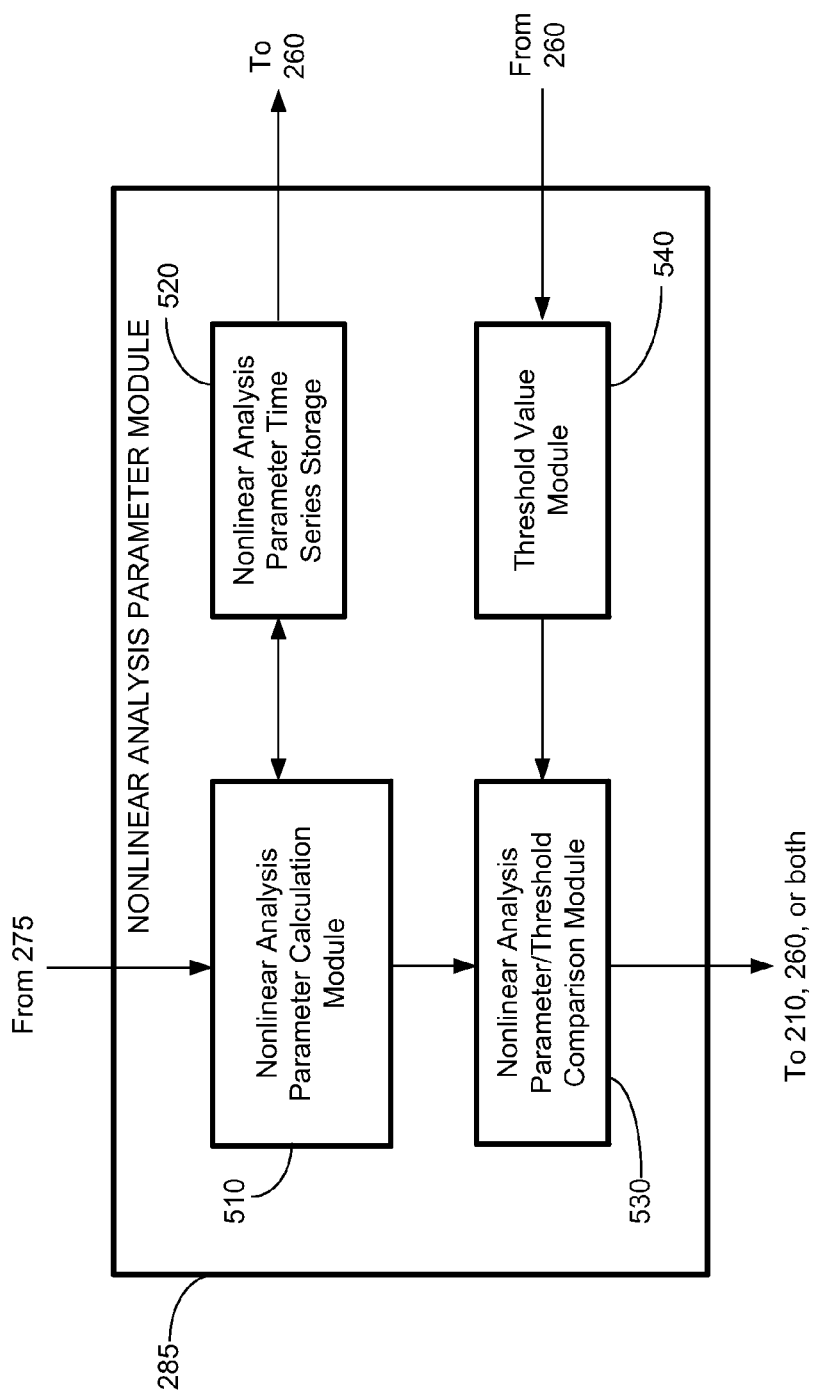
FIG. 4 is a block diagram of a nonlinear analysis module of a medical device, in accordance with one illustrative embodiment of the present invention.

Turning now to FIG. 4, a more detailed stylized depiction of the nonlinear analysis module 285 of FIG. 2, in accordance with one illustrative embodiment of the present invention is depicted. The nonlinear analysis module 285 may receive various data from the heart beat data processing module 275. Based upon data from the heart beat data processing module 275, the nonlinear analysis module 285 is capable of determining at least one nonlinear analysis parameter, such as one or more regularity and/or probability parameters as described above, and performing further calculations in light of the nonlinear analysis parameter(s), which may lead it to provide information to the controller 210. In one embodiment, the nonlinear analysis module 285 is capable of determining one or more nonlinear analysis parameters that indicate an actual or impending epileptic event, such as a seizure or a period of elevated risk of such a seizure. Based upon this determination, the nonlinear analysis module 285 may initiate one or more of several responsive actions, including generating an indication of at least one of an epileptic event or an impending epileptic event. This indication may be stored internally and/or externally, e.g., in the memory 217 (FIG. 2). This indication may also be transmitted to an external entity, e.g., to the monitoring unit 270 or an external device 610 (FIG. 5), and stored, e.g., into the local database unit 255 and/or the database unit 250 (FIG. 2). Nonlinear analysis module 285 may initiate other responsive actions such as providing an audible, visible, or tactile alert to the patient or a caregiver; logging a timestamp of the epileptic event; initiation of an seizure event parameter determination routine based upon data from the heart beat data processing module 275 and/or the nonlinear analysis module 285; communicating with one or more of database unit 250 or remote device 292, or notifying emergency services via email or autophone communications. It may be appreciated that, based upon the output of the nonlinear analysis module, responsive action(s) may be performed by either the MD 200, monitoring unit 270, or other devices such as remote device 292.

In another embodiment, a preventive therapy or an interventive therapy may be performed as a responsive action. The therapy may comprise, for example, an electrical stimulation of the vagus nerve 127.

Returning to FIG. 4, the beat interval time series, its statistical values, or both are analyzed by a nonlinear analysis parameter calculation module 510, which determines the value of the at least one nonlinear analysis parameter of interest. The nonlinear analysis parameter calculation module 510 may store results in nonlinear analysis parameter time series storage 520, which may be a portion of the memory 217 or a separate memory unit. The nonlinear analysis parameter calculation module 510 may also access information from nonlinear analysis parameter time series storage 520 to assess the dynamic of nonlinear analysis parameters or calculate derivative parameters. The nonlinear analysis parameter time series storage 520 may communicate nonlinear analysis parameter time series information to a monitoring unit 270 via communications unit 260.

After calculation module 510 calculates the at least one nonlinear analysis parameter of interest, nonlinear analysis parameter/threshold comparison module 530 may compare the calculated value to a threshold value. The threshold value used by the module 530 may be stored in threshold value module 540 after being placed there by a physician via communications unit 260 or after being calculated dynamically by the medical device 200. The threshold value used by the module 530 may be a portion of the memory 217 or a separate memory unit. In one embodiment, the threshold value module 540 may calculate a threshold value to provide an adaptive threshold rather than a fixed threshold. For example, thresholds may be calculated from a baseline chaos value for a particular patient that is determined from data stored in nonlinear analysis parameter time series storage 520, or other algorithms for determining a threshold may be implemented. In another embodiment, a nonlinear analysis parameter threshold may be modified based upon circadian rhythms of the patient.

Depending on the results of the comparison, the nonlinear analysis module 285 may provide information to controller 210 (if therapy is desired and the medical device 200 contains a stimulation unit 220 and associated hardware; if an indication of an epilepsy event is to be stored in memory 217, or both), to the communications unit 260 (if reporting of an indication of an epilepsy event via monitoring unit 270 to a physician, a database, etc. is desired), and/or to both.

Figure 5:
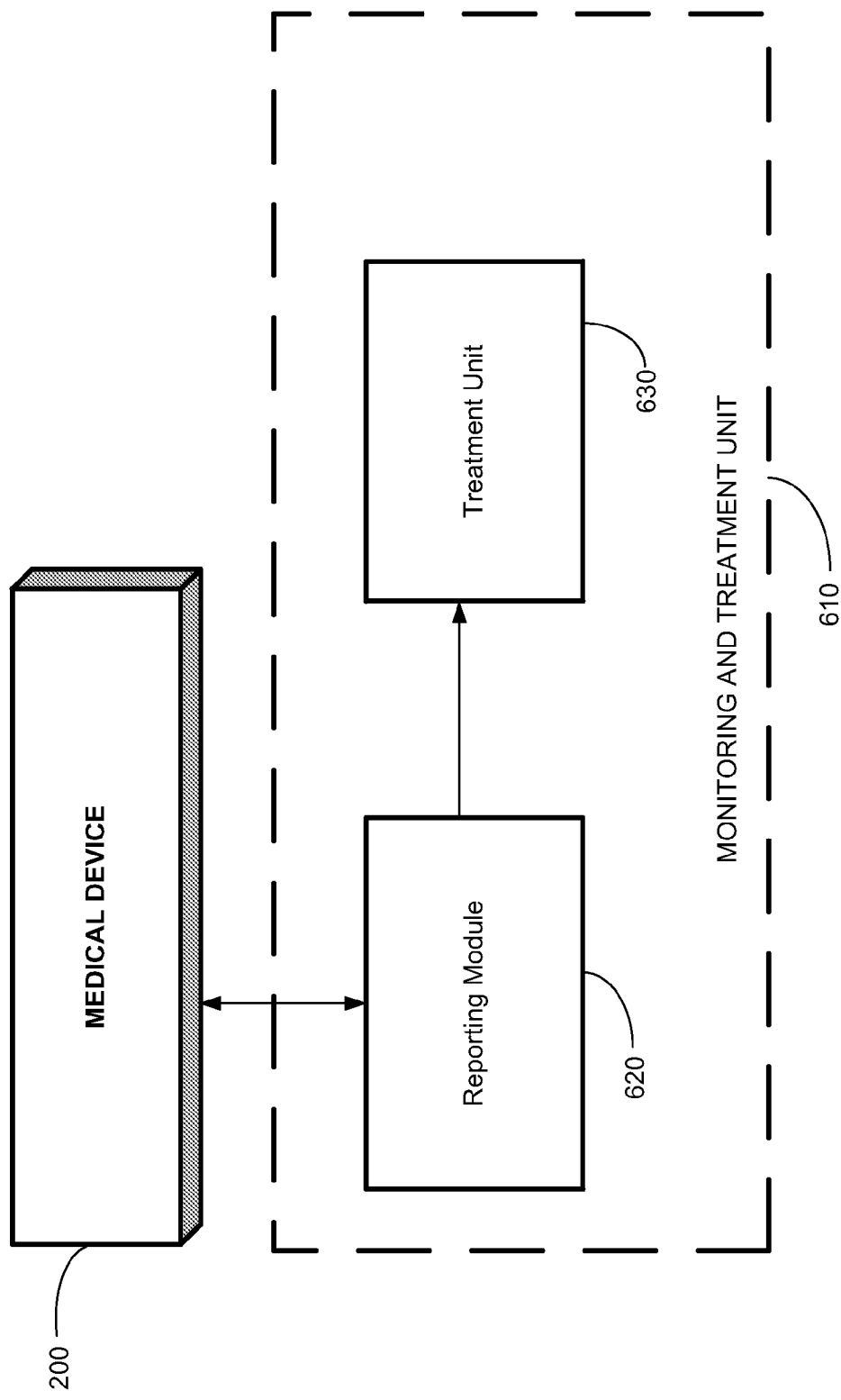
FIG. 5 is a block diagram of a medical device system external device, in accordance with one illustrative embodiment of the present invention.

Alternatively or in addition, according to one embodiment of the present invention as shown in FIG. 5, a monitoring and treatment unit 610, which may be a monitoring unit 270 or a unit other than medical device 200 implanted in or on the patient's body. The monitoring and treatment unit 610 may comprise a reporting module 620 to receive an indication of an occurring or impending epileptic event from the medical device 200 and a treatment unit 630 that can provide a therapy, such as an electrical signal to a neural structure of a patient, a drug delivery device, or another therapy device. In one embodiment, the medical device 200 may be external to the patient's body and the monitoring and treatment unit 610 may comprise a wholly or partially implanted system wirelessly coupled to medical device 200. More specifically, treatment unit 630 may be an implanted unit with programmed electrical parameters (e.g., amplitude, pulse width, frequency, on-time, off-time, etc.) that define a therapeutic stimulation signal provided by a stimulation unit 220 (FIGS. 2B, 2D) to the electrodes 128 via the leads 201 (FIGS. 2B, 2D). Reporting module 620 may be implanted or external to the patient's body.

Figure 6:
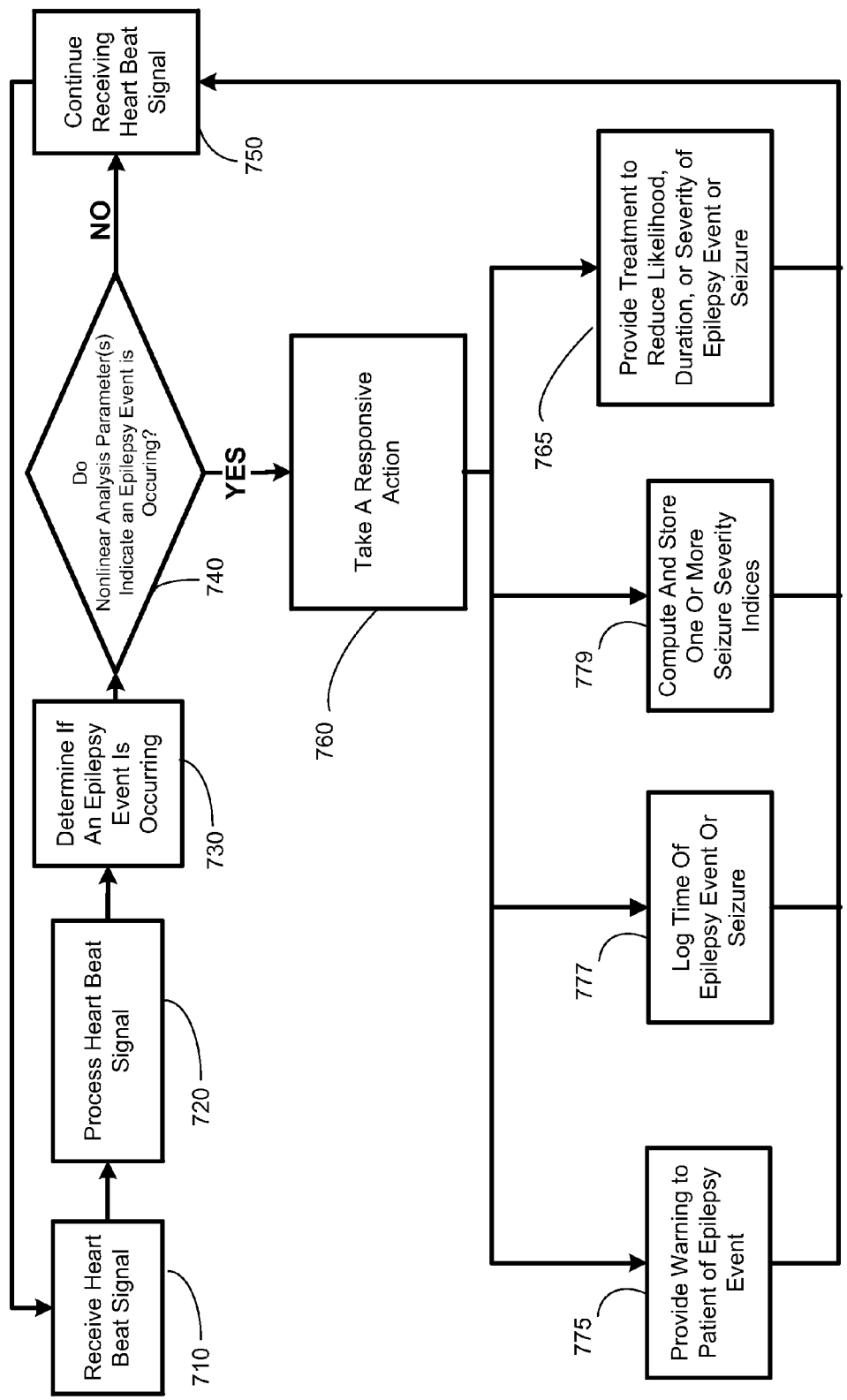
FIG. 6 illustrates a flowchart depiction of a method for detecting an epilepsy event, in accordance with an illustrative embodiment of the present invention.

Turning now to FIG. 6, a stylized flowchart depiction of detecting an epilepsy event, in accordance with one illustrative embodiment of the present invention, is provided. The medical device 200 receives a heart beat signal (block 710). Typically, the heart beat sensor interface 265 (FIGS. 2A-2D and 3A) of the medical device 200 receives the heart beat signal. After performing buffering, amplification, filtering, and A/D conversion of the heart beat signal, the heart rate data processing module 275 processes the heart rate data for performing analysis of heart beat data (block 720). From the processing of the heart beat data, it is determined if an epilepsy event, such as an unstable brain state, an increased risk of a seizure, or a seizure is occurring (block 740). This determination may be performed by a nonlinear analysis module 285 and/or NNXX processing module 286 (FIG. 2D). A more detailed description of the step of determining if an epilepsy event is occurring is provided in FIG. 7 and the accompanying description below.

The medical device 200 decides whether the an epilepsy event is occurring based on at least one of a nonlinear analysis parameter or an NNXX parameter (block 740). If no epilepsy event is occurring, the medical device 200 continues to receive the heart beat signal (block 750, returning flow to block 710).

However, if the medical device 200 determines that an epilepsy event is occurring in block 740, the medical device 200 or an external treatment unit 630 may take a responsive action selected from warning, logging the time of the seizure, computing and storing one or more seizure event indices, and treating the epilepsy event (block 760). If treating is performed, it may reduce the duration, reduce the severity, or reduce the likelihood of a seizure. A "reduced duration" should be apparent to the person of ordinary skill in the art having benefit of the present disclosure. A "reduced severity" may be defined as a moderation of seizure-induced changes in heart rate (i.e., at least a partial reduction in tachycardia or bradycardia), a reduction in muscle activity, a reduction of one or more physiological impacts caused by the seizure, a subjective determination by the patient that the seizure is milder, or a shorter or milder post-ictal period, among others, wherein the reduced severity is relative to the patient's typical seizure in the absence of treatment. A more detailed description of the step of providing a treatment is provided in FIG. 8 and the accompanying description below. A reduced likelihood of a seizure may be observed as a reduction in the frequency of seizures suffered by the patient in comparison to the frequency suffered prior to performance of the method.

Alternatively or in addition, the medical device 200 may provide a warning to the patient or his or her caregivers, physician, etc. (block 775); log a time of seizure (block 777); or compute and store one or more seizure event indices (block 779). The warning may manifest as a warning sound/tone or light implement by a nearby object adapted to receive indications of an impending epileptic event from the medical device 200; an automated email, text message, telephone call, or video message sent from the medical device 200, either directly or via a monitoring unit 270, to the patient's cellular telephone, PDA, computer, television, etc. Such a warning may allow the patient or his or her caregivers to take measures protective of the patient's well-being and those of others, e.g., pulling out of traffic and turning off a car, when the patient is driving; stopping the use of machinery, contacting another adult if the patient is providing childcare, removing the patient from a swimming pool or bathtub, lying down or sitting if the patient is standing, etc.

Figure 7:
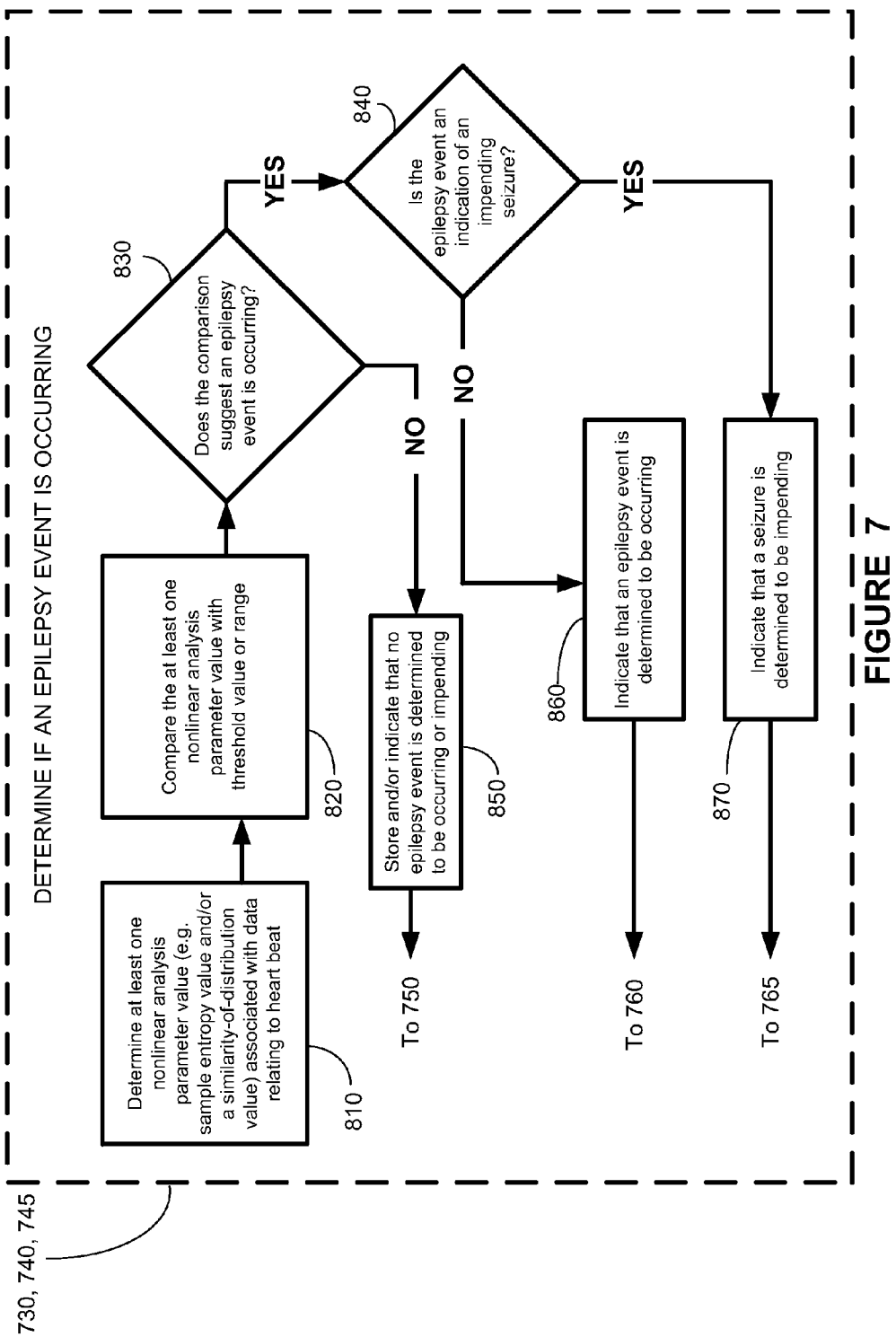
FIG. 7 illustrates a flowchart depiction of a determining step of the method depicted in FIG. 6, in accordance with an illustrative embodiment of the present invention.

Turning now to FIG. 7 a stylized flowchart depiction of determining whether nonlinear analysis parameters and/or an NNXX parameter indicate an epilepsy event is occurring (block 740 of FIG. 6), according to one embodiment of the invention, is provided. At least one nonlinear analysis parameter value or an NNXX parameter is determined from the heart beat data (block 810). The nonlinear analysis parameter may be one of those described above; another found to be correlated with one of those described above; or another found after empirical observation to be useful. The at least one nonlinear analysis or NNXX parameter value is then compared with at least one threshold value or range (block 820). As noted above, the threshold value may be a value that is predetermined by a user (e.g., a healthcare provider, the patient, etc.) a value that is changed periodically, or a value that is dynamically adjusted based upon various factors, such as the current physical, neural, emotional, and/or cognitive state of the patient, the environment surrounding the patient, circadian rhythms; etc.

The comparison may suggest that an epilepsy event is occurring, and if so, it may also suggest the epilepsy event is an indication of an actual or impending seizure (blocks 830 and 840). The three possibilities (no epilepsy event, occurring epilepsy event (which may be an actual or impending seizure) yield corresponding indications (blocks 850, 860, and 870), which are then passed to downstream elements (e.g., block 740 of FIG. 6). That is, if the comparison of one or more nonlinear analysis parameter or NNXX parameter (adjusted or otherwise) indicates that no epilepsy event is occurring, then an indication of such is stored and/or reported (block 850). If the comparison indicates that an epilepsy event is occurring, an indication of such is reported and/stored (block 860). If the comparison indicates that a seizure is impending, an indication of such is reported and/stored (block 880).

Figure 14:
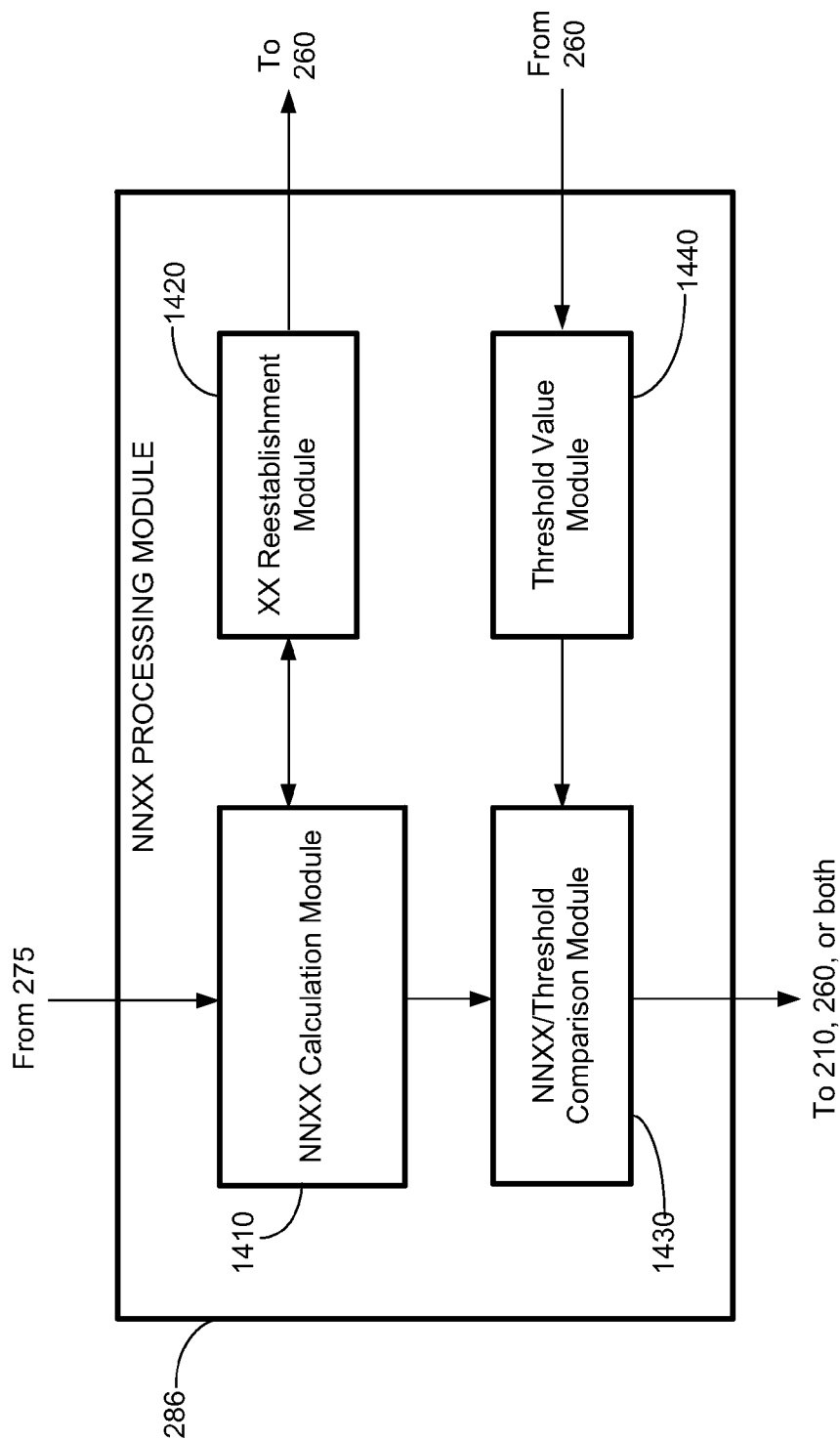
FIG. 14 is a block diagram of a NNXX processing module of a medical device, in accordance with one illustrative embodiment of the present invention.

Turning now to FIG. 14, a more detailed stylized depiction of the NNXX processing module 286 of FIGS. 2C and 2D, in accordance with one illustrative embodiment of the present invention is depicted. The NNXX processing module 286 may receive various data from the heart beat data processing module 275. Based upon data from the heart beat data processing module 275, the NNXX processing module 286 is capable of determining at least one NNXX value, and performing further calculations in light of the NNXX value, which may lead it to provide information to the controller 210. In one embodiment, the NNXX processing module 286 is capable of determining one or more NNXX values that indicate an actual or impending epileptic seizure, or a period of elevated risk of such a seizure. Based upon this determination, the NNXX processing module 286 may initiate one or more of several responsive actions, including generating an indication of at least one of an epileptic event or an impending epileptic event. This indication may be stored internally and/or externally, e.g., in the memory 217 (FIG. 2). This indication may also be transmitted to an external entity, e.g., to the monitoring unit 270 or an external device 610 (FIG. 5), and stored, e.g., into the local database unit 255 and/or the database unit 250 (FIG. 2). NNXX processing module 286 may initiate other responsive actions such as providing an audible, visible, or tactile alert to the patient or a caregiver; logging a timestamp of the epileptic seizure; initiation of a seizure event determination routine based upon data from the heart beat data processing module 275 and/or the NNXX processing module 286; communicating with one or more of database unit 250 or remote device 292, or notifying emergency services via email or autophone communications. It may be appreciated that, based upon the output of the nonlinear analysis module, responsive action(s) may be performed by either the MD 200, monitoring unit 270, or other devices such as remote device 292.

Returning to FIG. 14, the beat interval time series, its statistical values, or both are analyzed by a NNXX calculation module 1410, which determines the at least one NNXX value of interest. The NNXX calculation module 1410 may receive instruction as to which value of XX to use from XX determination module 1420, which may be programmed with a value of XX or may dynamically calculate values of XX on an ongoing basis. The XX determination module 1420 may communicate information to and/or from a monitoring unit 270 via communications unit 260.

After NNXX calculation module 1410 calculates the at least one NNXX value of interest, NNXX Threshold comparison module 1430 may compare the calculated NNXX value to a threshold value. The threshold value used by the module 1430 may be stored in threshold value module 1440 after being programmed by a physician via communications unit 260 or after being calculated by the medical device 200. The threshold value used by the module 1430 may be stored in a portion of the memory 217 or a separate memory unit. In one embodiment, the threshold value module 1440 may calculate a threshold value to provide an adaptive threshold rather than a fixed threshold. For example, thresholds may be calculated from a baseline value for a particular patient that is determined from data stored in memory 217 or another storage location described above, or other algorithms for determining a threshold may be implemented.

Depending on the results of the comparison, the NNXX processing module 286 may provide information to controller 210 (if therapy is desired and the medical device 200 contains a stimulation unit 220 and associated hardware; if an indication of an epilepsy event is to be stored in memory 217, or both), to the communications unit 260 (if reporting of an indication of an epilepsy event via monitoring unit 270 to a physician, a database, etc. is desired), and/or to both.

Figure 15:
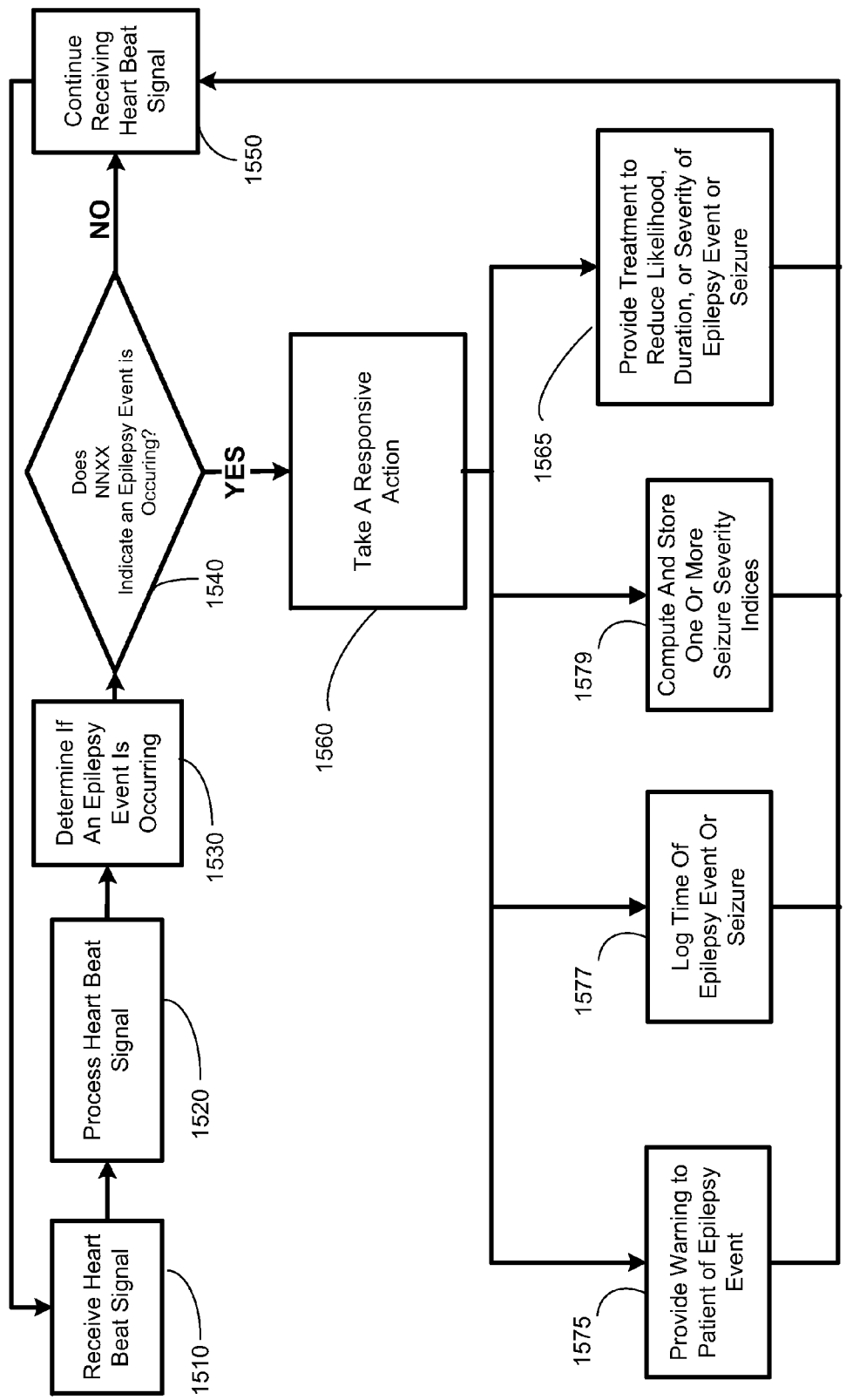
FIG. 15 illustrates a flowchart depiction of a method for detecting an epilepsy event, in accordance with an illustrative embodiment of the present invention.

Turning now to FIG. 15, a stylized flowchart depiction of detecting an epilepsy event, in accordance with one illustrative embodiment of the present invention, is provided. The medical device 200 receives a heart beat signal (block 1510). Typically, the heart beat sensor interface 265 (FIGS. 2 and 3A) of the medical device 200 receives the heart beat signal. After performing buffering, amplification, filtering, and A/D conversion of the heart beat signal, the heart beat data processing module 275 processes the heart beat data for performing analysis of heart beat data (block 1520). From the processing of the heart beat data, it is determined if an epilepsy event, such as an unstable brain state, an increased risk of a seizure, or a seizure is occurring (block 1540). This determination may be performed by a NNXX processing module 286. A more detailed description of the step of determining if an epilepsy event is occurring is provided in FIG. 16 and the accompanying description below.

The medical device 200 decides whether an epilepsy event is occurring based on the at least one NNXX value (block 1540). If no epilepsy event is occurring, the medical device 200 continues to receive the heart beat signal (block 1550, returning flow to block 1510).

However, if the medical device 200 determines that an epilepsy event is occurring in block 1540, the medical device 200 or an external treatment unit 630 may take a responsive action selected from warning, logging the time of the seizure, computing and storing one or more seizure severity indices, and treating the epilepsy event (block 1560). If treating is performed, it may reduce the duration, reduce the severity, or reduce the likelihood of a seizure. A "reduced duration" should be apparent to the person of ordinary skill in the art having benefit of the present disclosure. A "reduced severity" may be defined as a moderation of seizure-induced changes in heart rate (i.e., at least a partial reduction in tachycardia or bradycardia), a reduction in muscle activity, a reduction of one or more physiological impacts caused by the seizure, a subjective determination by the patient that the seizure is milder, or a shorter or milder post-ictal period, among others, wherein the reduced severity is relative to the patient's typical seizure in the absence of treatment. A more detailed description of step of providing a treatment is provided in FIG. 8 and accompanying description below. A reduced likelihood may be observed as a reduction in the frequency of seizures suffered by the patient in comparison to the frequency suffered prior to performance of the method.

Alternatively or in addition, the medical device 200 may provide a warning to the patient or his or her caregivers, physician, etc. (block 1575); log a time of seizure (block 1577); or compute and store one or more seizure severity indices (block 1579). The warning may manifest as a warning tone or light implement by a nearby object adapted to receive indications of an impending epileptic event from the medical device 200; an automated email, text message, telephone call, or video message sent from the medical device 200, either directly or via an monitoring unit 270, to the patient's cellular telephone, PDA, computer, television, etc. Such a warning may allow the patient or his or her caregivers to take measures protective of patient's well-being and those of others, e.g., pulling out of traffic and turning off a car, when the patient is driving; stopping the use of machinery, contacting another adult if the patient is providing childcare, removing the patient from a swimming pool or bathtub, lying down or sitting if the patient is standing, etc.

Figure 16:
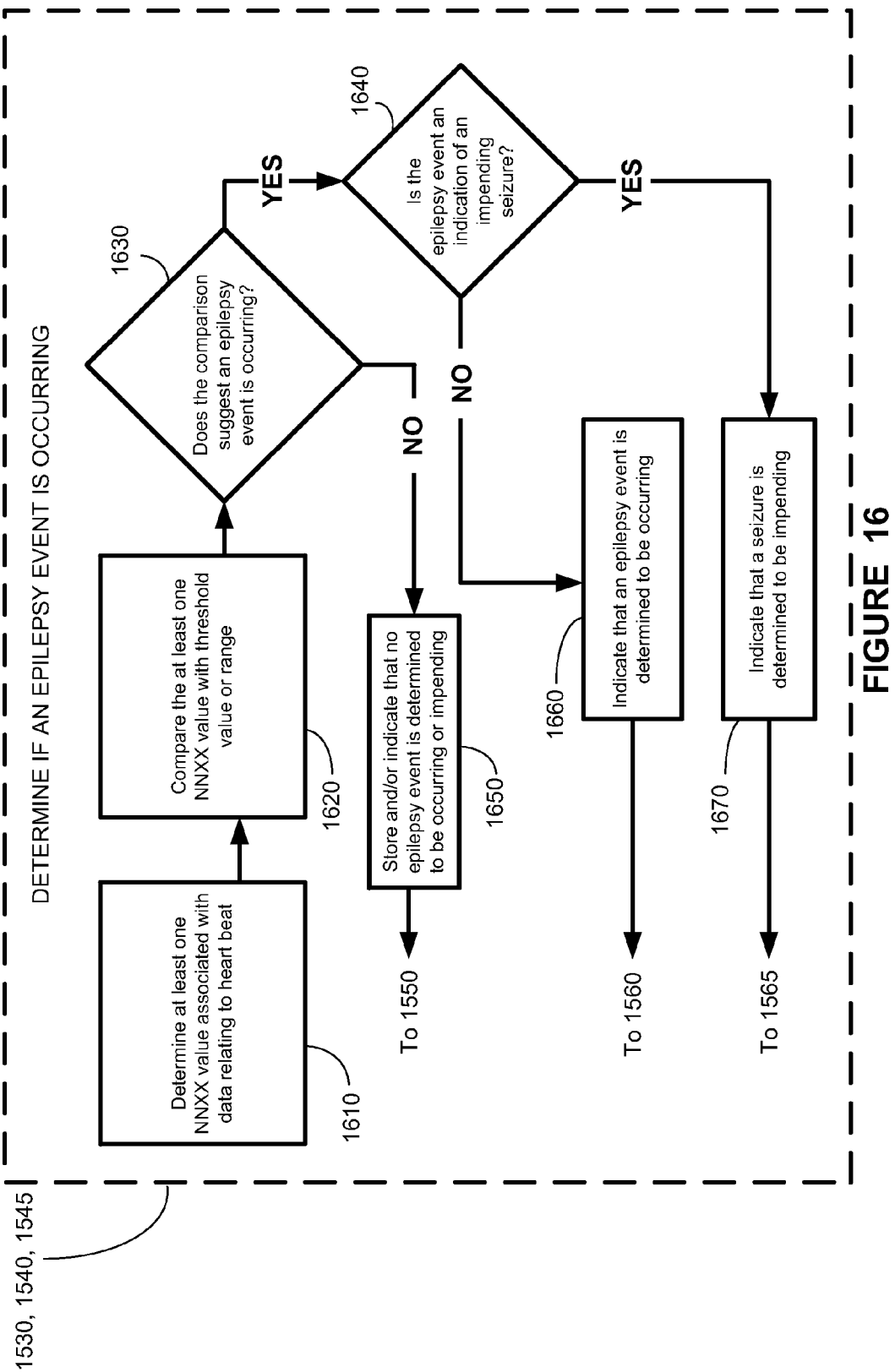
FIG. 16 illustrates a flowchart depiction of a determining step of the method depicted in FIG. 15, in accordance with an illustrative embodiment of the present invention.

Turning now to FIG. 16 a stylized flowchart depiction of determining whether at least one NNXX value indicates an epilepsy event is occurring (block 1540 of FIG. 6), according to one embodiment of the invention, is provided. At least one NNXX value is determined from heart beat data (block 1610). The at least one NNXX value is then compared with a threshold value or range (block 1620). As noted above, the threshold value may be a value that is predetermined by a user (e.g., a healthcare provider, the patient, etc.) based upon several factors. The threshold may be changed periodically or may be dynamically adjusted based upon various factors, such as the current physiological condition of the patient, the environment surrounding the patient, circadian rhythms; etc.

The comparison may suggest that an epilepsy event is occurring, and if so, it may also suggest the epilepsy event is an indication of an actual or impending seizure (blocks 1630 and 1640). The three possibilities (no epilepsy event, occurring epilepsy event [which may be an actual or impending event]) yield corresponding indications (blocks 1650, 1660, and 1670), which are then passed to downstream elements (e.g., blocks 1550, 1560, or 1565 of FIG. 15). That is, if the comparison of one or more NNXX values indicates that no epilepsy event is occurring, then an indication of such is stored and/or reported (block 1550). If the comparison indicates that an epilepsy event is occurring, an indication of such is reported and/stored (block 1560). If the comparison indicates that a seizure is impending, an indication of such is reported and/stored (block 1565).

Figure 8:
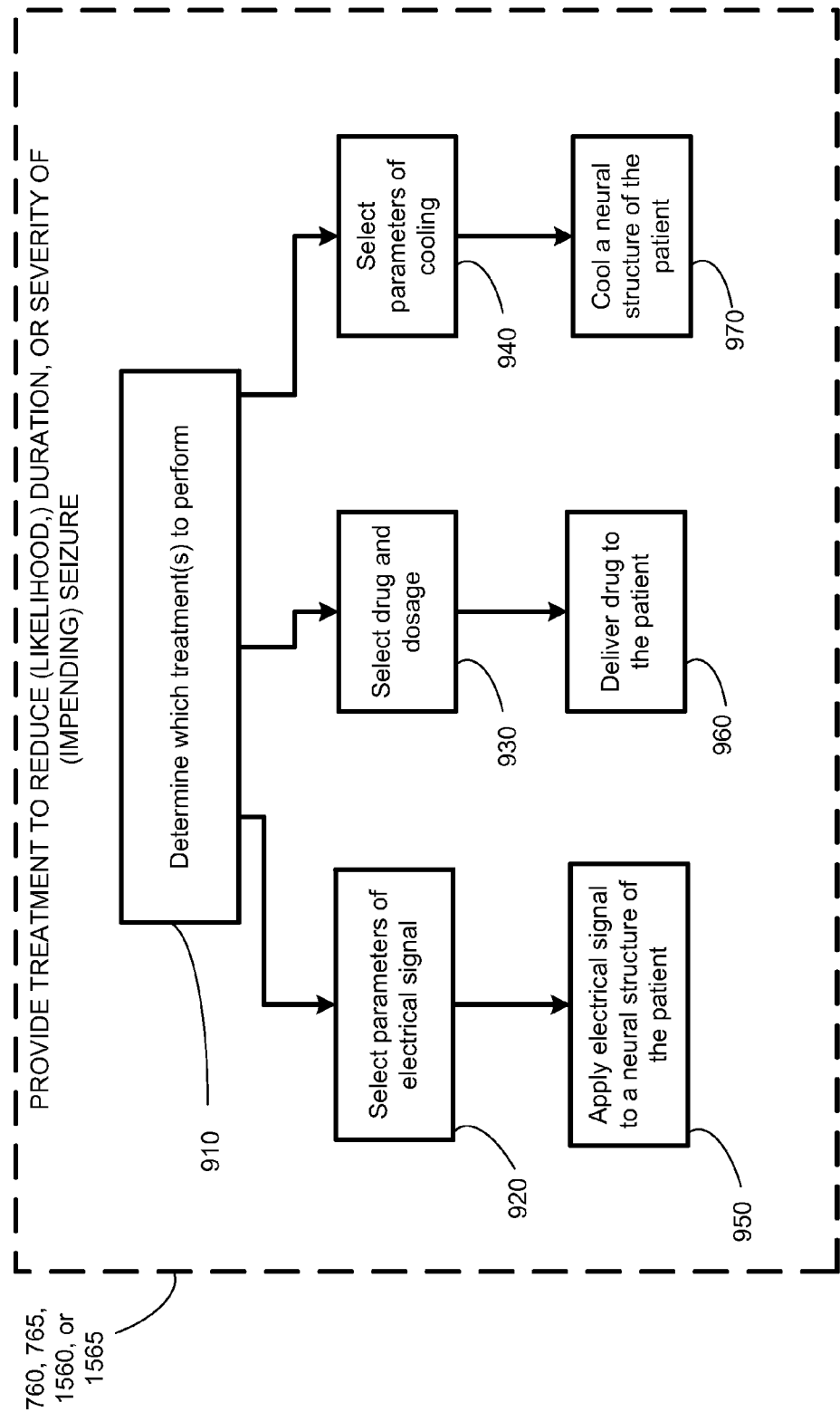
FIG. 8 illustrates a flowchart depiction of a providing step of the method depicted in FIG. 6 or FIG. 15, in accordance with an illustrative embodiment of the present invention.

Turning now to FIG. 8 a stylized flowchart depiction of providing a treatment based upon a determination that a seizure is occurring or impending (block 740 of FIG. 6 or 1540 of FIG. 15), according to one embodiment of the invention, is provided. Upon determining that a seizure is occurring or impending, the medical device 200 determines which treatment(s) to perform (block 910). This determination is made based upon predetermined rules set up by a healthcare professional. For example, one result of a nonlinear analysis parameter threshold comparison described above may lead to a determination that only electrical signal treatment is required. However, during a more intense seizure, the threshold comparison may indicate that another type of treatment or a combination of treatments may be required. The treatments may be electrical signal therapy, drug therapy, and/or another therapy.

With regard to an electrical stimulation treatment, the parameters of electrical signal therapy (including an "on time" of zero milliseconds, i.e., the application of no electrical signals) are selected (block 920). Similarly, the drug and dosage of drug therapy (including a dosage of zero milligrams, i.e., the application of no drugs) are selected (block 930) and the parameters of another therapy are selected (block 940). Thereafter, the electrical signal, drug, or other therapy are applied, delivered, or performed (blocks 950, 960, and 970). The combination of treatment, if any, may be determined based upon the results of the comparison of the calculated nonlinear analysis parameter(s) to threshold values.

Particular embodiments may combine or eliminate one or more of the treatment therapies available. Thus, a given device may comprisd only electrical signal therapy, only drug delivery therapy, or combinations of any of the foregoing therapies.

The above methods may be performed by a computer readable program storage device encoded with instructions that, when executed by a computer, perform the method described herein.

Figure 9:
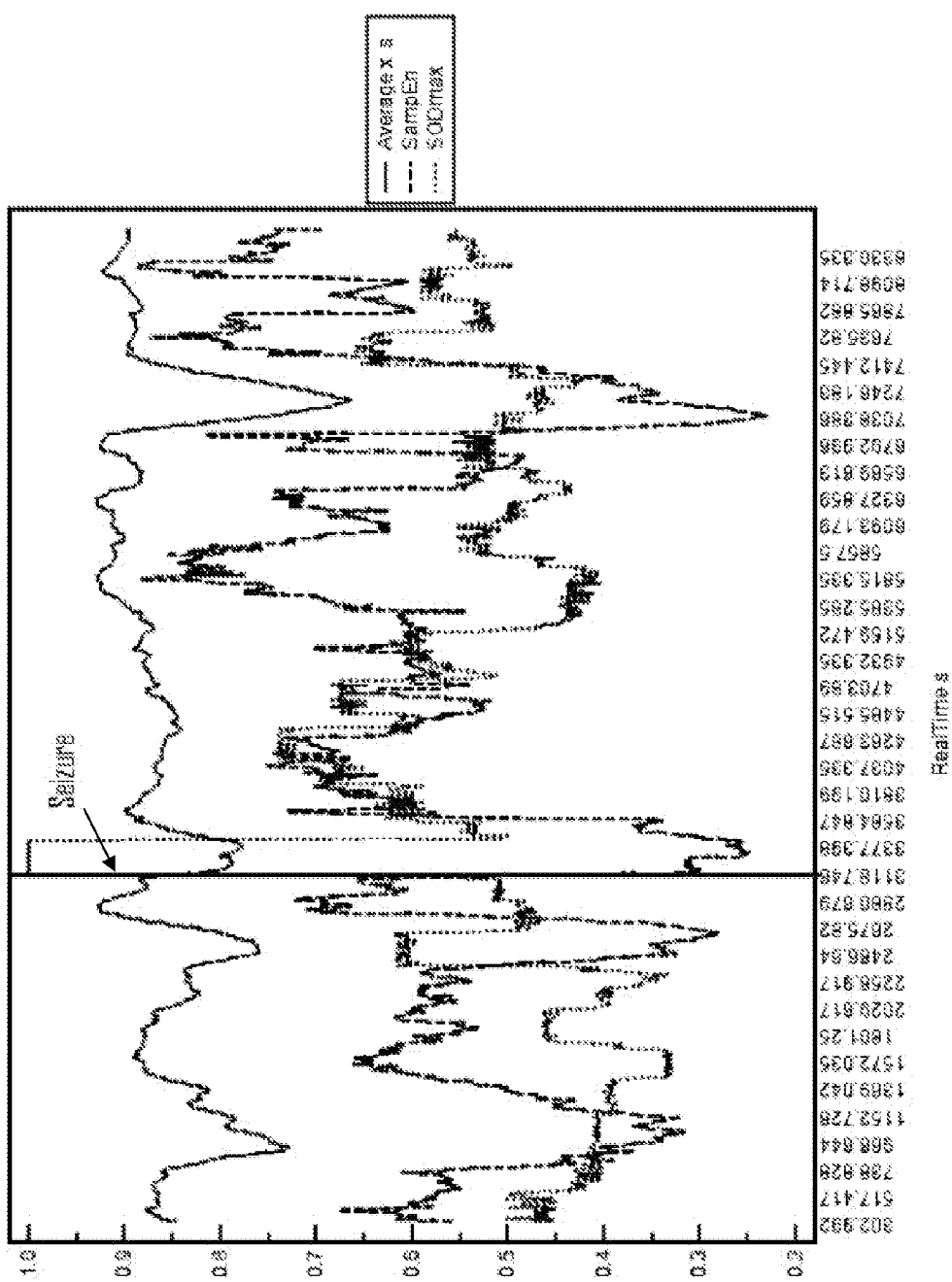
FIG. 9 illustrates a time series of observed values for sample entropy, similarity of distribution, and average interbeat interval in a patient with diagnosed epilepsy.

FIG. 9 shows an example from a patient whose seizure was monitored in the clinic by an EEG machine. One channel of the EEG machine was used for collecting heart beat data (ECG). The SampEn (dashed line) and SOD (dotted line) were calculated retrospectively, but could have been calculated in real time with appropriate programming of appropriate devices.

As can be seen, the patient's SampEn value significantly decreased and SOD value simultaneously sharply rose at t=3109 second, just 28 sec after the electrographic onset of the seizure which was marked by a neurologist on the EEG.

Figure 10:
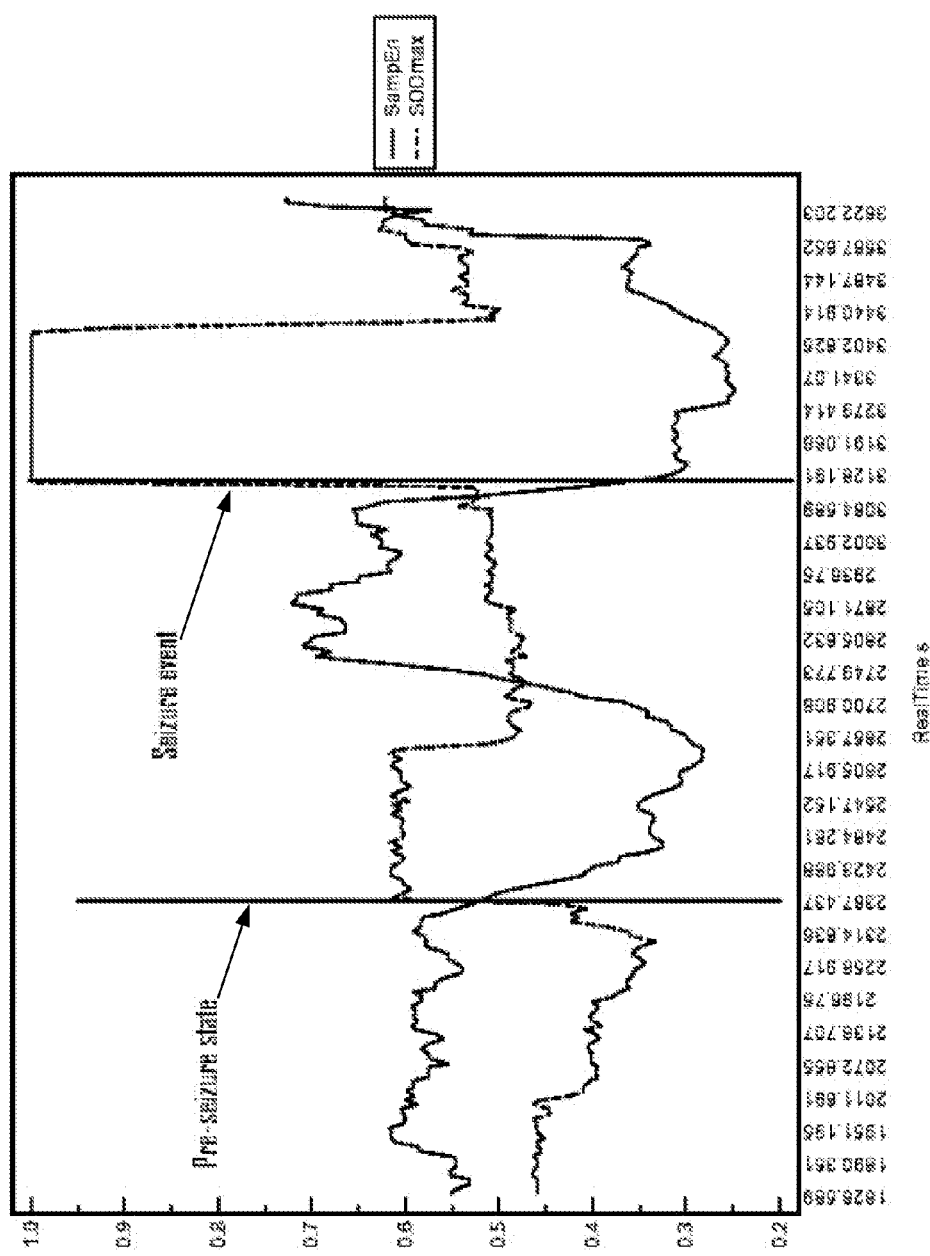
FIG. 10 illustrates a time series of observed values for sample entropy and similarity of distribution in the same patient as FIG. 9.

FIG. 10 shows a 30-second excerpt with pre-seizure and seizure events marked by the simultaneous decrease of SampEn and increase of SOD.

Figure 11:
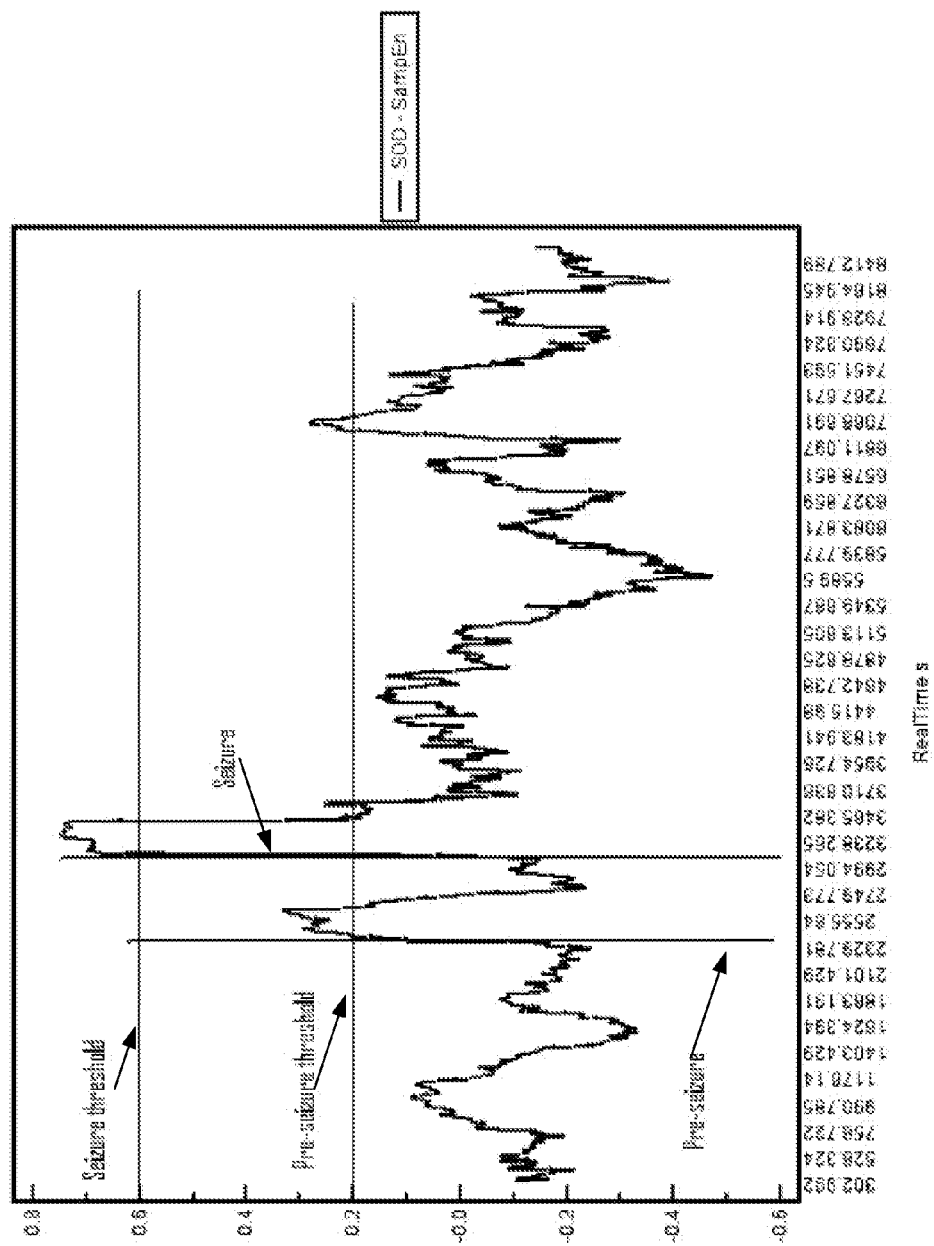
FIG. 11 illustrates a time series of observed values for similarity of distribution minus sample entropy of two and half hours of monitoring with detected and marked pre-seizure and seizure events based on threshold values in the same patient as FIG. 9.

FIG. 11 shows the same record as FIG. 9, but pre-seizure and seizure events are marked by the difference of SOD and SampEn values (SOD−SampEn). The detection is based on threshold values as 0.2 for pre-seizure event and 0.6 for seizure event. The pre-seizure event was detected 11 minutes before the seizure.

FIGS. 12-13 show the same record as FIG. 9, and show that statistical and spectral parameters derived from heart rate data provide poor specificity and poor sensitivity at detecting epilepsy events or seizures.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps, or in the sequence of steps, of the method described herein without departing from the concept, spirit, and scope of the invention, as defined by the appended claims. It should be especially apparent that the principles of the invention may be applied to selected cranial nerves other than, or in addition to, the vagus nerve, as well as to other neural structures such as the brain and spinal cord to achieve particular results in treating patients having epilepsy, depression, or other medical conditions.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. A non-transitory computer readable storage device storing instructions that, when executed by a processor, cause the processor to perform operations comprising:
   receiving data related to a beat sequence of a patient's heart;
   dynamically recalculating an XX value used to determine at least one NNXX value, wherein the at least one NNXX value corresponds to a number of adjacent normal R-R intervals in a sample that differ by more than XX milliseconds;
   determining the at least one NNXX value based on the beat sequence of the patient's heart;
   performing a first comparison of the at least one NNXX value to an NNXX threshold; and
   providing an output indicative of an unstable brain state, a brain state indicative of an elevated probability of a seizure event, a brain state indicative of an impending seizure, an aura, a seizure, or a combination thereof, wherein the output is determined based on the first comparison.

2. The non-transitory computer readable storage device of claim 1, wherein the operations further comprise performing a responsive action, the responsive action including providing a warning, logging a time of the output, determining one or more seizure severity indices based on the seizure event, treating the seizure event based upon the first comparison of the at least one NNXX value to the NNXX threshold, or any combination thereof.

3. The non-transitory computer readable storage device of claim 1, wherein the XX value is dynamically recalculated based on an equation:

$$XX = (a + b * x),$$

wherein x is a standard deviation (SD) value or a root mean squared successive distances (RMSSD) value, wherein the SD and the RMSSD are based on each interval between beats of the beat sequence of the patient's heart;
wherein a is a first constant; and
wherein b is a second constant.

4. The non-transitory computer readable storage device of claim 1, wherein the at least one NNXX value is determined during a time period that is less than 60 contiguous beats of the beat sequence of the patient's heart.

5. The non-transitory computer readable storage device of claim 1, wherein the operations further comprise:
   determining at least one regularity nonlinear analysis parameter based on the beat sequence of the patient's heart;
   determining at least one predictability nonlinear analysis parameter based on the beat sequence of the patient's heart; and
   performing a second comparison of the at least one regularity nonlinear analysis parameter to a regularity nonlinear analysis threshold, performing a third comparison of the at least one predictability nonlinear analysis parameter to a predictability nonlinear analysis threshold, or performing both the second comparison and the third comparison; and
   wherein the output is further determined based on the second comparison, the third comparison, or both.

6. The non-transitory computer readable storage device of claim 5, wherein the at least one regularity nonlinear analysis parameter is a sample entropy (SampEN) value and the at least one predictability nonlinear analysis parameter is a similarity of distribution (SOD) value.

7. The non-transitory computer readable storage device of claim 1, wherein receiving the data related to the beat sequence of the patient's heart includes sensing a time of the beat sequence of the patient's heart and generating a time series data stream from the time of the beat sequence.

8. The non-transitory computer readable storage device of claim 7, wherein generating the time series data stream includes sensing a plurality of R peaks from the R-R intervals and determining a time stamp based on the plurality of R peaks to generate the time series data stream.

9. The non-transitory computer readable storage device of claim 2, wherein the responsive action further includes applying an electrical signal to a neural structure of the patient, delivering a drug to the patient, or both.

10. The non-transitory computer readable storage device of claim 9, wherein the electrical signal is provided to the neural structure of the patient via an electrode.

11. A non-transitory computer readable storage device storing instructions that, when executed by a processor, cause the processor to perform operations comprising:
   receiving data related to a beat sequence of a patient's heart;
   determining, based on the beat sequence, a first cardiac parameter and a second cardiac parameter;
   adjusting the first cardiac parameter based on the second cardiac parameter to generate an adjusted first cardiac parameter;
   performing a comparison of the adjusted first cardiac parameter to a first cardiac parameter threshold;

providing an output indicative of an occurrence of a seizure event of the patient based on the comparison, wherein the first cardiac parameter is adjusted based on a nonlinear mathematical function, wherein the first cardiac parameter corresponds to an XX parameter for determining an NNXX value according to a number of adjacent normal R-R intervals in a sample that differ by more than XX milliseconds, wherein the XX parameter is dynamically adjusted based on an equation:

$$XX=(a+b*x),$$

wherein x is a standard deviation (SD) value or a root mean squared successive distances (RMSSD) value, wherein the SD value and the RMSSD value are based on each interval between beats of the beat sequence of the patient's heart, wherein a is a first constant, and wherein b is a second constant.

12. The non-transitory computer readable storage device of claim 11, wherein the seizure event includes an unstable brain state, a brain state indicative of an elevated probability of a seizure event, a brain state indicative of an impending seizure, an aura, a seizure, or a combination thereof.

13. A non-transitory computer readable storage device storing instructions that, when executed by a processor, cause the processor to perform operations comprising:

receiving data related to a beat sequence of a patient's heart;

dynamically recalculating an XX value used to determine at least one NNXX value corresponding to a number of adjacent normal R-R intervals in a sample that differ by more than XX milliseconds, wherein the XX value is dynamically recalculated based on an equation: XX=(a+b*x), wherein x is a standard deviation (SD) value or a root mean squared successive distances (RMSSD) value, wherein the SD value and the RMSSD value are based on each interval between beats of the beat sequence of the patient's heart, wherein a is a first constant, and wherein b is a second constant;

determining the at least one NNXX value based on the beat sequence of the patient's heart and the XX value;

performing a first comparison of the at least one NNXX value to an NNXX threshold; and providing an output indicative of an unstable brain state, a brain state indicative of an elevated probability of a seizure event, a brain state indicative of an impending seizure, an aura, a seizure, or a combination thereof, wherein the output is determined based on the first comparison.

14. The non-transitory computer readable storage device of claim 13, wherein the at least one NNXX value is determined during a time period that is less than 60 contiguous beats of the beat sequence of the patient's heart.

15. The non-transitory computer readable storage device of claim 13, wherein the operations further comprise:

determining at least one regularity nonlinear analysis parameter based on the beat sequence of the patient's heart;

determining at least one predictability nonlinear analysis parameter based on the beat sequence of the patient's heart; and performing a second comparison of the at least one regularity nonlinear analysis parameter to a regularity nonlinear analysis threshold, performing a third comparison of the at least one predictability nonlinear analysis parameter to a predictability nonlinear analysis threshold, or performing both the second comparison and the third comparison;

wherein the output is further determined based on the second comparison, the third comparison, or both.

16. The non-transitory computer readable storage device of claim 15, wherein the at least one regularity nonlinear analysis parameter is a sample entropy (SampEN) value and the at least one predictability nonlinear analysis parameter is a similarity of distribution (SOD) value.

17. The non-transitory computer readable storage device of claim 13, wherein receiving the data related to the beat sequence of the patient's heart includes sensing a time of the beat sequence of the patient's heart and generating a time series data stream from the time of the beat sequence.

18. The non-transitory computer readable storage device of claim 17, wherein receiving the data related to the beat sequence of the patient's heart includes receiving a series of R-R intervals, and wherein generating the time series data stream includes sensing a plurality of R peaks from the R-R intervals and determining a time stamp based on the plurality of R peaks to generate the time series data stream.

19. The non-transitory computer readable storage device of claim 13, wherein the operations further comprise performing a responsive action, the responsive action including providing a warning, logging a time of the output, determining one or more seizure severity indices based on the seizure event, treating the seizure event based upon the first comparison of the at least one NNXX value to the NNXX threshold, or any combination thereof.

20. The non-transitory computer readable storage device of claim 19, wherein the responsive action further includes applying an electrical signal to a neural structure of the patient, delivering a drug to the patient, or both.

21. The non-transitory computer readable storage device of claim 20, wherein the electrical signal is provided to the neural structure of the patient via an electrode.

* * * * *